(12) United States Patent
Semple et al.

(10) Patent No.: US 8,772,502 B2
(45) Date of Patent: Jul. 8, 2014

(54) ALKYLSULFINYL-SUBSTITUTED THIAZOLIDE COMPOUNDS

(75) Inventors: J. Edward Semple, Tampa, FL (US); Jean-Francois Rossignol, St. Petersburg, FL (US)

(73) Assignee: Romark Laboratories, L.C., Tampa, FL (US)

( * ) Notice: Subject to any disclaimer, the term of this patent is extended or adjusted under 35 U.S.C. 154(b) by 0 days.

(21) Appl. No.: 13/284,242

(22) Filed: Oct. 28, 2011

(65) Prior Publication Data

US 2012/0108591 A1 May 3, 2012

Related U.S. Application Data

(60) Provisional application No. 61/408,938, filed on Nov. 1, 2010.

(51) Int. Cl.
*C07D 277/34* (2006.01)
*C07D 277/36* (2006.01)

(52) U.S. Cl.
USPC .......................................................... 548/185

(58) Field of Classification Search
USPC ................................................ 548/202, 185
See application file for complete search history.

(56) References Cited

U.S. PATENT DOCUMENTS

| 5,169,846 | A | 12/1992 | Crooks |
| 5,578,621 | A | 11/1996 | Rossignol |
| 2009/0036467 | A1 | 2/2009 | Rossignol et al. |

OTHER PUBLICATIONS

U.S. Appl. No. 13/353,686, filed 2012, Rossignol et al.*
STN display: Veterinary Parasitology (2009) 162(3-4), 230-235, Gargala et al.*
STN display: Journal of Biological Chemistry (2009), 284(43), 29798-29808, Rossignol et al.*
STN display: Experimental Parasitology (2008), 118(1), 80-88, Muller et al.*
STN result, Rossignol et al., U.S. Patent Application Publication 20100330173 (2010).*
U.S. Appl. No. 12/821,571 Rossignol et al. filed 2010.*
Amadi et al., "Effect of nitazoxanide on morbidity and mortality in Zambian children with cryptosporidiosis: a randomized controlled trial," The Lancet, Nov. 2, 2002, 360:1375-1380.
Blight et al., "Efficient Initiation of HCV RNA Replication in Cell Culture," Science, Dec. 8, 2000, 290:1972-1974.
Blight et al., "Efficient Replication of Hepatitis C Virus Genotype 1a RNAs in Cell Culture," Journal of Virology, Mar. 2003, 77(5):3181-3190.
Broekhuysen et al., "Nitazoxanide: pharmacokinetics and metabolism in man," International Journal of Clinical Pharmacology and Therapeutics, 2000, 38(8):387-394.
Chen et al., "The Natural History of Hepatitis C Virus (HCV) Infection," Int. J. Med. Sci., 2006, 3:47-52.

Elazar et al., "The Anti-Hepatitis C Agent Nitazoxanide Induces Phosphorylation of Eukaryotic Initiation Factor 2α Via Protein Kinase Activated by Double-Stranded RNA Activation," Gastroenterology, 2009, 137:1827-1835.
Fox et al., "Nitazoxanide: A New Thiazolide Antiparasitic Agent," Review of Anti-Infective Agents, Apr. 15, 2005, 40:1173-1180.
Hoffman et al., "Antiparasitic Drug Nitazoxanide Inhibits the Pyruvate Oxidoreductases of *Helicobacter pylori*, Selected Anaerobic Bacterial and Parasites, and *Campylobacter jejuni*," Antimicrobial Agents and Chemotherapy, Mar. 2007, 51(3):868-876.
Korba et al., "Nitazoxanide, tizoxanide and other thiazolides are potent inhibitors of hepatitis B virus and hepatitis C virus replication," Antiviral Res., 2008, 77:56-63.
Lavanchy, D., "Hepatitis B virus epidemiology, disease burden, treatment, and current and emerging prevention and control measures," Journal of Viral Hepatitis, 2004, 11:97-107.
Lindenbach et al., "Complete Replication of Hepatitis C Virus in Cell Culture," Science, Jul. 22, 2005, 309:623-626.
Musher et al., "Nitazoxanide for the Treatment of *Clostridium difficile* Colitis," CID, Aug. 15, 2006, 43:421-427.
Okuse et al., "Enhancement of antiviral activity against hepatitis C virus in vitro by interferon combination therapy," Antiviral Research, 2005, 65:23-34.
Ortiz et al., "Randomized clinical study of nitazoxanide compared to metronidazole in the treatment of symptomatic giardiasis in children from Northern Peru," Ailment Pharmacol. Ther., 2001, 15:1409-1415.
Pankuch et al., "Activities of Tizoxanide and Nitazoxanide Compared to Those of Five Other Thiazoles and Three Other Agents against Anaerobic Species," Antimicrobial Agents and Chemotherapy, Mar. 2006, 50(3):1112-1117.
Rao et al., "Design, Synthesis, and Biological Evaluation of 6-Substituted-3-(4-methanesulfonylphenyl)-4-phenylpyran-2-ones: A Novel Class of Diarylheterocyclic Selective Cyclooxygenase-2 Inhibitors," J. Med. Chem., 2003, 46:4872-4882.
Rossignol et al., "Nitazoxanide in the treatment of viral gastroenteritis: a randomized double-blind placebo-controlled clinical trial," Aliment. Pharacol. Ther., 2006, 24:1423-1430.
Rossignol et al., "Treatment of Diarrhea Caused by *Giardia intestinalis* and *Entamoeba histolytica* or *E. dispar*: A Randomized, Double-Blind, Placebo-Controlled Study of Nitazoxanide," J. Infect. Diseases, 2001, 184:381-384.
Rossignol et al., "Effect of Nitazoxanide in Persistent Diarrhea and Enteritis Associated with *Blastocystis hominis*," Clinical Gastroenterology and Hepatology, 2005, 3:987-991.
Rossignol et al., "Effect of nitazoxanide for treatment of severe rotavirus diarrhea: randomized double-blind placebo-controlled trial," The Lancet, Jun. 13, 2006 online, 1-6.
Rossignol et al., "Effect of Nitazoxanide in Diarrhea and Enteritis Caused by *Cryptosporidium* Species," Clinical Gastoenterology and Hepatology, 2006, 4:320-324.
Rossignol et al., "Thiazolides, a New Class of Anti-influenza Molecules Targeting Viral Hemagglutinin at the Post-translational Level," J. Biol. Chem., Oct. 23, 2009, 284:29798-29808.

(Continued)

*Primary Examiner* — Yong Chu
*Assistant Examiner* — Sonya Wright
(74) *Attorney, Agent, or Firm* — Foley & Lardner LLP

(57) ABSTRACT

A new class of alkylsulfinyl thiazolides is described. These compounds show strong activity against hepatitis viruses.

17 Claims, No Drawings

(56) References Cited

OTHER PUBLICATIONS

Schiavi et al., "Preparation of *N-Tert*-butoxycarbonylthiourea opens the way to protected 2-aminothiazoles," Synthetic Communications, 2002, 32(11):1671-1674.

Tomei et al., "HCV antiviral resistance: the impact of in vitro studies on the development of antiviral agents targeting the viral NS5B polymerase," Antiviral Chemistry & Chemotherapy, 2005, 16:225-245.

Tong et al., "Identification and analysis of fitness of resistance mutations against the HCV protease inhibitor SCH 503034," Antiviral Research, 2006, 70:26-38.

Wong et al., "Update of viral hepatitis: 2005," Current Opinion in Gastroenterology, 2006, 22:241-247.

Yim et al., "Evolution of Multi-Drug Resistant Hepatitis B Virus During Sequential Therapy," Hepatology, Sep. 2006, 44(3):703-712.

* cited by examiner

ALKYLSULFINYL-SUBSTITUTED THIAZOLIDE COMPOUNDS

CROSS-REFERENCE TO RELATED APPLICATIONS

This application claims priority from U.S. Provisional Application 61/408,938, filed Nov. 1, 2010.

STATEMENT REGARDING FEDERALLY SPONSORED RESEARCH OR DEVELOPMENT

The invention disclosed herein was made with Government support under NIAID contract NO1-AI-30046 to Georgetown University Medical Center. Accordingly, the U.S. Government may have certain rights in this invention.

FIELD OF THE INVENTION

The present invention is directed to new alkylsulfinyl thiazolide compounds and pharmaceutical compositions thereof and their methods of use for the treatment of disease. Methods of inhibition of viral pathogen activity in a human or animal subject are also provided for the treatment of diseases, such as hepatitis C virus (HCV), hepatitis B virus (HBV) and related viral pathogens.

BACKGROUND

Hepatitis B Virus (HBV) and Hepatitis C Virus (HCV) are major public health problems, causing more than an estimated 500 million chronic infections worldwide. Both viruses are a source of progressive liver disease, and are the major risk factors for nearly all cases of primary hepatocellular carcinoma [Chen, S. L., Morgan, T. R., Int. J. Med. Sci. 3, 47-52 (2006); Lavanchy, D., J. Viral. Hepat. 11, 97-107 (2004); Wong, S. N., Lok, A. S., Curr. Opin. Gastroenterol. 22, 241-247 (2006)]. Licensed standards of care for both viral infections, while effective in many cases, are sub-optimal and do not result in virologic or clinical 'cures' in most individuals [Wong and Lok (2006)]. The development of drug-resistance in HBV, including strains carrying resistance to multiple licensed agents is an emerging clinical problem, and drug-resistance for future HCV therapies is predicted to be a significant clinical issue [Tomei, L. et al., Antivir. Chem. Chemother. 16, 225-245 (2005); Tong et al., Antivir. Res. 70, 28-38 (2006); Yim et al., Hepatology 44, 703-712 (2006)]. Thiazolide compounds such as nitazoxanide (NTZ) are anti-infective and possess activity against anaerobic bacteria, protozoa and viruses [Rossignol, J. F. Santoro, M. G. et al., J. Biol. Chem., 284, 29798-29808 (2009); Korba, B. E. et al. Antiviral Res. 77, 56-63 (2008); Fox, L. M., Saravolatz, L. D., Clin. Infect. Dis. 40, 1173-1180 (2005); Pankuch, G. A., Appelbaum, P. C., Antimicrob. Agents Chemother. 50, 112-117 (2006); Rossignol, J. F. et al., Lancet 368, 124-129 (2006); Rossignol and El-Gohary, Aliment. Pharmacol. Ther. 24, 1423-1430 (2006)]. Originally developed as a treatment of intestinal protozoan infections, the antiviral properties of NTZ were discovered during the course of its development for treating cryptosporidiosis in patients with acquired immune deficiency syndrome (AIDS).

NTZ is marketed in the United States for treating diarrhea and enteritis caused by *Cryptosporidium* spp or *Giardia lamblia* in adults and children down to 12 months of age (Alinia®, Romark Laboratories, Tampa, Fla. USA). Clinical trials have demonstrated effectiveness of NTZ in treating diarrhea and enteritis associated with enteric protozoan infections caused by *Cryptosporidium* spp, *G. lamblia*, *Entamoeba histolytica* and *Blastocystis hominis* [Amadi et al., Lancet 360, 1375-1380. (2002); Oritz et al., Aliment. Pharmacol. Ther. 15, 1409-1415. (2001); Rossignol. J. F. et al., J. Infect. Dis. 184, 381-384 (2001); Clin. Gastroenterol. Hepatol. 3, 987-991. (2005), Clin. Gastroenterol. Hepatol. 4, 320-324. (2006)]. Recent randomized double-blind clinical trials have demonstrated effectiveness of NTZ in treating *Clostridium difficile* colitis in adults, rotavirus gastroenteritis in young children, and rotavirus and norovirus gastroenteritis in adults [Musher et al., Clin. Infect. Dis. 43, 421-427 (2006); Rossignol et al, Lancet 368, 124-129 (2006); Rossignol and El Gohary, Aliment. Pharmacol. Ther. 24, 1423-1430 (2006)].

The mechanism of action of NTZ against anaerobic organisms is attributed to interference with pyruvate:ferredoxin oxidoreductase (PFOR) enzyme-dependent electron transfer reactions, which are essential for anaerobic energy metabolism [Hoffman et al., Antimicrob. Agents Chemother. 51, 868-876 (2006)]. The mechanism of antiviral activity of NTZ against hepatitis B and C has not been fully elucidated, although recent studies suggest host cell-related protein modulation. In the RNA viruses such as influenza A [Rossignol J. F. and Santoro M. G. (2009)] and HCV [Elazar M., et al. Gastroenterology, 137, 1827-1835 (2009)], NTZ selectively leads to inhibition of viral glycoproteins at the post-translational level, preventing final assembly of the virus before exiting the cell to infect another cell. Also in HCV, NTZ and other thiazolide analogs cause an increase in eIF2α phosphorylation induced by PKR activation, which are key mediators of intracellular host antiviral activity [Elazar M. (2009].

Following oral administration of a 500 mg tablet, NTZ is partially absorbed from the gastrointestinal tract and rapidly hydrolyzed in plasma to form its active circulating metabolite, tizoxanide (TIZ). NTZ is not detected in plasma. Maximum serum concentrations of TIZ, reach approximately 10 µg/mL (37 µM) [Stockis et al., Int. J. Clin. Pharmacol. Ther. 40, 221-227 (2002)] following oral administration of one 500 mg NTZ tablet (Alinia®) with food. TIZ is glucurono-conjugated in the liver and excreted in urine and bile. Approximately two-thirds of an oral dose pass through the intestinal tract and is excreted in feces as TIZ [Broekhuysen, J. et al., Int. J. Clin. Pharmacol. Ther. 38, 387-394 (2000)]. The elimination half-life of TIZ from plasma is approximately 1.5 hours. TIZ does not inhibit cytochrome P450 enzymes, and therefore, no drug-drug interactions are expected [Broekhuysen et al., 2000; Stockis et al. (2002)]. The most commonly reported side-effects in clinical trials include mild abdominal pain, headache, diarrhea and nausea, which occur at rates similar to those reported for patients receiving placebo. While most of the clinical experience with NTZ has involved a 3 to 14 day treatment regimen, continued use of the drug for periods as long as 4 years has been evaluated in patients with AIDS-related cryptosporidiosis without any significant drug-related adverse events [Fox, L. M., Saravolatz, L. D. (2005); Rossignol and El-Gohary (2006)].

The present application relates generally to the field of alkylsulfinyl thiazolide compounds. In particular, the antiviral activity of certain alkylsulfinyl thiazolide compounds is demonstrated against HCV compared to the antiviral activity of structurally related thiazolides Nitazoxanide (NTZ), Tizoxanide (TIZ) respectively.

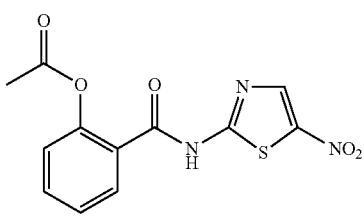

Nitazoxanide (NTZ)

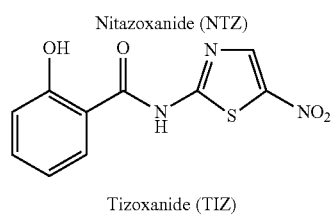

Tizoxanide (TIZ)

We disclosed a novel class of alkylsulfonyl-substituted thiazolides, e.g., RM4863, RM5015, their analogs and prodrugs, in US 2009/0036467 A1, which is hereby incorporated by reference in its entirety. The inventive compounds have demonstrated utility against inhibitor of HCV replication in cell culture.

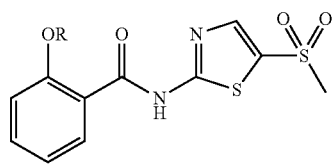

RM4863, R = H
RM4864 R = CH₃CO

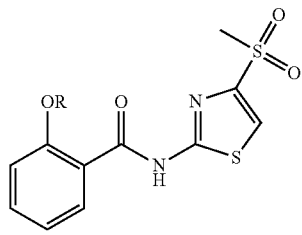

RM5015, R = H
RM5014 R = CH₃CO

As opposed to the 5-nitrothiazolide series of compounds exemplified by NTZ and TIZ, acetate and related prodrugs of several other thiazolides including the alkylsulfonyl-substituted analogs are essentially inactive in HCV cell culture assays. The simple acetate prodrugs RM4864 and RM5014 are metabolically stable under the cell assay conditions and are not being hydrolyzed by cellular esterases to the parent phenolic drugs RM4863 and RM 5015, respectively in any appreciable amount.

SUMMARY OF THE INVENTION

Herein, results of studies characterizing the activities of certain alkylsulfinyl thiazolides, which may be regarded as chimeric structural isosteres of both the nitro and alkylsulfonyl thiazolide classes, are presented. In particular, the antiviral activity of alkylsulfinyl thiazolides against HCV is demonstrated.

Compounds, their pharmaceutical compositions and methods of use for the treatment of viral pathogens are described together with methods of synthesizing and using the compounds including methods for inhibiting viruses in a patient by administering the compounds.

As stated above, the present invention discloses novel alkylsulfinyl-substituted thiazolides and salts thereof, their pharmaceutical compositions, and methods of use in treating disorders and conditions caused by viral pathogens, defined by structural Formula I:

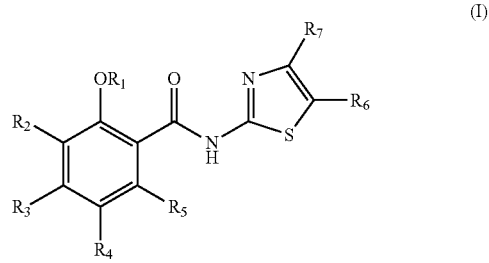

(I)

wherein:

$R_1$ is selected from the group consisting of hydrogen and Q-C(=O)—, any of which may be optionally substituted.

$R_2$ to $R_5$ are each independently selected from the group consisting of hydrogen, duterium, hydroxy, F, Cl, Br, CN, $NO_2$, $(C_1-C_6)$-alkyl, $(C_3-C_8)$-cycloalkyl, $(C_1-C_6)$-alkoxy, carboxy, $(C_1-C_6)$-alkoxycarbonyl, amino, $(C_1-C_6)$-acylamino, amido, $(C_1-C_6)$-alkylamido, $(C_1-C_6)$-dialkylamido, $(C_1-C_6)$-alkylsulfonylamino, $(C_1-C_6)$-haloalkyl, $(C_1-C_6)$-perhaloalkyl, $(C_1-C_6)$-perhaloalkoxy, $(C_1-C_6)$-alkylthio, $(C_1-C_6)$-alkylthioalkyl, $(C_1-C_6)$-alkylsulfonyl, $(C_3-C_8)$-cycloalkylsulfonyl, arylsulfonyl, arylalkylsulfonyl, heteroarylsulfonyl, heteroarylalkylsulfonyl, $(C_1-C_6)$-alkylsulfonamido, N,N'—$(C_1-C_6)$-dialkylsulfonamido, aryl, aryloxy, arylthio, arylalkylthio, heteroaryl, heteroaryloxy, heteroarylalkoxy, heteroarylthio, heteroarylalkylthio, heterocycloalkyl, heterocycloalkoxy, and Q-C(=O)—, any of which may be optionally substituted; or any two contiguous $R_1$, $R_2$ or $R_3$ moieties may be combined together with the atoms to which they are attached and joined to form an optionally substituted 5- to 8-membered heterocycloalkyl ring.

In one embodiment, when one of $R_6$ or $R_7$ is hydrogen, the other is independently selected from the group consisting of $(C_1-C_6)$-alkylsulfinyl, $(C_1-C_6)$-alkylsulfinylalkyl, $(C_2-C_6)$-alkenylsulfinyl, $(C_2-C_6)$-alkynylsulfinyl, $(C_3-C_8)$-cycloalkylsulfinyl, $(C_5-C_8)$-cycloalkenylsulfinyl, arylsulfinyl, arylalkylsulfinyl, arylalkenylsulfinyl, heteroarylsulfinyl, heteroarylalkylsulfinyl, heteroarylalkenylsulfinyl, and heterocycloalkylsulfinyl, any of which may be optionally substituted; or the $R_6$ and $R_7$ moieties may be combined together with the atoms to which they are attached and joined to form an optionally substituted 5- to 8-membered ring that incorporates a sulfinyl (—S[O]—) moiety.

Substituent Q is $R_8$, $OR_8$, $NHR_8$, or $NR_8R_9$; $R_8$ and $R_9$ are independently selected from the group consisting of hydrogen, $(C_1-C_{12})$-alkyl, $(C_2-C_{12})$-alkenyl, $(C_2-C_{12})$-alkynyl, $(C_3-C_8)$-cycloalkyl, aryl, arylalkyl, arylalkenyl, heterocycloalkyl, heteroaryl, heteroarylalkyl, and heteroarylalkenyl, any of which may be optionally substituted; or $R_8$ and $R_9$, together with the atoms to which they are attached, may be joined to form an optionally substituted 5- to 8-membered heterocycloalkyl ring; any of which may be optionally substituted.

Compounds according to the present invention possess useful virus inhibiting or modulating activity, and may be used in the treatment or prophylaxis of a disease or condition in which a viral pathogen plays an active role. Thus, in a broad aspect, the present invention also provides pharmaceutical compositions comprising one or more compounds of the present invention together with a pharmaceutically acceptable carrier (e.g., a diluent or excipient), as well as methods of making and using the compounds and compositions. The pharmaceutical composition may comprise an effective amount of the compound for treating HCV, HBV, and other viral infections.

In certain embodiments, the present invention provides methods for inhibiting or modulating a viral pathogen. In other embodiments, the present invention provides methods for treating a viral-mediated disorder in a patient in need of such treatment comprising administering to said patient a therapeutically effective amount of a compound or composition according to the present invention. Also disclosed are methods for treating HCV, HBV and other viral infections comprising administering the disclosed pharmaceutical compositions to a patient in need thereof. For example, the patient may have a chronic HCV infection. The present invention also contemplates the use of compounds disclosed herein for use in the manufacture of a medicament for the treatment of a disease or condition ameliorated by the inhibition or modulation of viral activity.

DETAILED DESCRIPTION OF THE PREFERRED EMBODIMENTS

Unless otherwise specified, "a" or "an" means "one or more."

In certain embodiments, the compounds of the present invention conform to Formula I:

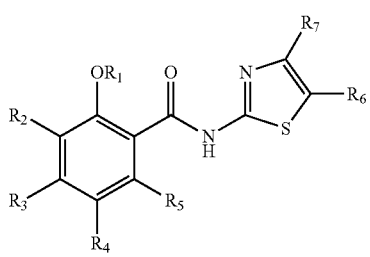

(I)

For the inventive compounds, therefore, $R_1$ is selected from the group consisting of hydrogen and Q-C(=O)—, any of which may be optionally substituted.

$R_2$ to $R_5$ are independently selected from the group consisting of hydrogen, D, hydroxy, F, Cl, Br, CN, $NO_2$, $(C_1-C_6)$-alkyl, $(C_3-C_6)$-cycloalkyl, $(C_1-C_6)$-alkoxy, $(C_1-C_6)$-alkoxycarbonyl, $(C_1-C_6)$-dialkylamido, $(C_1-C_3)$-haloalkyl, $(C_1-C_4)$-perhaloalkyl, $(C_1-C_4)$-perhaloalkoxy, $(C_1-C_6)$-alkylthio, $(C_1-C_6)$-alkylsulfonyl, $(C_3-C_6)$-cycloalkylsulfonyl, arylsulfonyl, arylalkylsulfonyl, heteroarylsulfonyl, heteroarylalkylsulfonyl, aryl, aryloxy, arylthio, heteroaryl, heteroaryloxy, heterocycloalkyl, and heterocycloalkoxy, any of which may be optionally substituted.

For Formula I compounds, when one of $R_6$ or $R_7$ is hydrogen, the other is independently selected from the group consisting of $(C_1-C_6)$-alkylsulfinyl, $(C_1-C_6)$-alkylsulfinylalkyl, $(C_3-C_8)$-cycloalkylsulfinyl, $(C_5-C_8)$-cycloalkenylsulfinyl, arylsulfinyl, arylalkylsulfinyl, heteroarylsulfinyl, heteroarylalkylsulfinyl, and heterocycloalkylsulfinyl, any of which may be optionally substituted; or the $R_6$ and $R_7$ moieties may be combined together with the atoms to which they are attached and joined to form an optionally substituted 5- to 7-membered ring that incorporates a sulfinyl (—S[O]—) moiety.

In certain embodiments, Q is $R_8$, $OR_8$, $NHR_8$, or $NR_8R_9$; $R_8$ and $R_9$ are independently selected from the group consisting of hydrogen, $(C_1-C_{12})$-alkyl, $(C_2-C_{12})$-alkenyl, $(C_3-C_8)$-cycloalkyl, aryl, arylalkyl, arylalkenyl, heterocycloalkyl, heteroaryl, heteroarylalkyl, and heteroarylalkenyl, any of which may be optionally substituted; or $R_8$ and $R_9$, together with the atoms to which they are attached, may be joined to form an optionally substituted 5- to 7-membered heterocycloalkyl ring; any of which may be optionally substituted.

In other embodiments, the compounds of the present invention have structural Formula I, wherein $R_1$ is selected from the group consisting of hydrogen and Q-C(=O)—, any of which may be optionally substituted.

$R_2$ to $R_5$ are independently selected from the group consisting of hydrogen, D, F, Cl, Br, CN, $(C_1-C_6)$-alkyl, $(C_3-C_6)$-cycloalkyl, $(C_1-C_6)$-alkoxy, $(C_1-C_3)$-haloalkyl, $(C_1-C_4)$-perhaloalkyl, $(C_1-C_4)$-perhaloalkoxy, $(C_1-C_6)$-alkylthio, aryl, aryloxy, heteroaryl, heteroaryloxy, heterocycloalkyl, and heterocycloalkoxy, any of which may be optionally substituted.

In one embodiment, $R_7$ is hydrogen and $R_6$ is independently selected from the group consisting of $(C_1-C_6)$-alkylsulfinyl, $(C_1-C_6)$-alkylsulfinylalkyl, $(C_3-C_6)$-cycloalkylsulfinyl, arylsulfinyl, arylalkylsulfinyl, heteroarylsulfinyl, heteroarylalkylsulfinyl, and heterocycloalkylsulfinyl, any of which may be optionally substituted; or the $R_6$ and $R_7$ moieties may be combined together with the atoms to which they are attached and joined to form an optionally substituted 5- to 7-membered ring that incorporates a sulfinyl (—S[O]—) moiety.

Q is $R_8$, $OR_8$, $NHR_8$, or $NR_8R_9$; $R_8$ and $R_9$ are independently selected from the group consisting of hydrogen, $(C_1-C_{12})$-alkyl, $(C_2-C_{12})$-alkenyl, $(C_3-C_8)$-cycloalkyl, aryl, arylalkyl, arylalkenyl, heterocycloalkyl, heteroaryl, heteroarylalkyl, and heteroarylalkenyl, any of which may be optionally substituted; or $R_8$ and $R_9$, together with the atoms to which they are attached, may be joined to form an optionally substituted 5- to 7-membered heterocycloalkyl ring; any of which may be optionally substituted.

For certain aspects of the present invention, Formula I compounds are described in which $R_1$ is selected from the group consisting of hydrogen and Q-C(=O)—, any of which may be optionally substituted.

$R_2$ to $R_5$ are independently selected from the group consisting of hydrogen, D, F, Cl, Br, CN, $(C_1-C_6)$-alkyl, $(C_3-C_6)$-cycloalkyl, $(C_1-C_6)$-alkoxy, $(C_1-C_3)$-haloalkyl, $(C_1-C_4)$-perhaloalkyl, $(C_1-C_4)$-perhaloalkoxy, and $(C_1-C_6)$-alkylthio, any of which may be optionally substituted.

Substituent $R_7$ is hydrogen and $R_6$ is independently selected from the group consisting of $(C_1-C_6)$-alkylsulfinyl, $(C_1-C_6)$-alkylsulfinylalkyl, $(C_3-C_6)$-cycloalkylsulfinyl, arylsulfinyl, arylalkylsulfinyl, heteroarylsulfinyl, heteroarylalkylsulfinyl, and heterocycloalkylsulfinyl, any of which may be optionally substituted; or the $R_6$ and $R_7$ moieties may be combined together with the atoms to which they are attached and joined to form an optionally substituted 5- to 7-membered ring that incorporates a sulfinyl (—S[O]—) moiety.

Q is $R_8$, $OR_8$, $NHR_8$, or $NR_8R_9$; $R_8$ and $R_9$ are independently selected from the group consisting of hydrogen, $(C_1-C_{12})$-alkyl, $(C_2-C_{12})$-alkenyl, $(C_3-C_8)$-cycloalkyl, aryl, arylalkyl, arylalkenyl, heterocycloalkyl, heteroaryl, heteroarylalkyl, and heteroarylalkenyl, any of which may be optionally substituted; or $R_8$ and $R_9$, together with the atoms to which they are attached, may be joined to form an optionally substituted 5- to 7-membered heterocycloalkyl ring; any of which may be optionally substituted.

In further embodiments, the compounds of the present invention have structural Formula I, wherein $R_1$ is selected from the group consisting of hydrogen, and Q is selected from hydrogen, methyl, ethyl, n-propyl, isopropyl, n-butyl, 2-methyl-1-propyl, sec-butyl, tert-butyl, 2,3-dimethylbutan-2-yl, cyclohexyl, 2,6-dimethylcyclohexyl, 1-methylcyclohexyl, phenyl, 4-pyridyl, benzyl, 4-pyridylmethyl, phenylethyl, (S)-1-hydroxy-(phenylethyl), 2-pyrazinyl, phenylethenyl, (E)-2-(4-pyridazinyl)-1-ethenyl, (E)-4-(2-)-1H-imidazolyl-1-ethenyl, 3-acetoxyl-1-propyl, ethoxycarbonylethyl, methoxylcarbonylpropyl, N-methylaminocarbonylethyl, N-ethylaminocarbonylpropyl, 3-(N-ethylaminocarbonyl)-2,2-dimethyl-1-propyl, N-(morpholinoethyl)aminocarbonylethyl, 3-pyridylmethylaminocarbonylethyl, 4-pyridylmethylaminocarbonylethyl, 4-pyridylmethylaminocarbonylpropyl, carboxyethyl, carboxypropyl, 2-piperidinyl, 3-piperidinyl, 4-piperidinyl, 2-piperazinyl, (S)-1-aminoethyl, (R)-1-aminoethyl, (S)-1-aminoisobutyl, 1-aminocyclopropyl, methoxy, ethoxy, isopropoxy, isobutoxy, neopentyloxy, cyclohexyloxy, 4-piperidinyloxy, 3-acetoxy-2-methyl-1-propoxy, tert-pentyloxy, 4-acetoxybenzyloxy, 3-(4-acetoxyphenyl)-2-propenyloxy, (E)-2-methyl-4-(2-oxo-2,3-dihydrobenzofuran-5-yl)but-3-en-2-yloxy, pivaloyloxymethoxy, pivaloyloxy-1-ethoxy, isopropoxycarbonyloxymethoxy, isopropoxycarbonyloxy-1-ethoxy, amino, N-methylamino, N-ethylamino, N,N-dimethylamino, N-propylamino, N-isopropylamino, N-butylamino, N-piperidinyl, N-piperazinyl, N-4-methylpiperazinyl, N-cyclohexylamino, N-benzylamino, N-(2,4-dimethoxy)benzylamino, 2-(N-methylcarboxamido)phenylamino, N-methyl-2-hydroxyethylamino, $N^1,N^2$-dimethyl-1,2-ethanediamin-1-yl, $N^1,N^2$-diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl.

$R_2$ to $R_5$ are independently selected from the group consisting of hydrogen, duterium, F, Cl, Br, CN, $(C_1$-$C_6)$-alkyl, $(C_3$-$C_6)$-cycloalkyl, $(C_1$-$C_6)$-alkoxy, $(C_1$-$C_3)$-haloalkyl, $(C_1$-$C_4)$-perhaloalkyl, $(C_1$-$C_4)$-perhaloalkoxy, and $(C_1$-$C_6)$-alkylthio, any of which may be optionally substituted.

$R_7$ is hydrogen and $R_6$ is independently selected from the group consisting of $(C_1$-$C_6)$-alkylsulfinyl, $(C_1$-$C_6)$-alkylsulfinylalkyl, $(C_3$-$C_6)$-cycloalkylsulfinyl, arylsulfinyl, arylalkylsulfinyl, heteroarylsulfinyl, heteroarylalkylsulfinyl, and heterocycloalkylsulfinyl, any of which may be optionally substituted.

Alternatively, $R_6$ and $R_7$ moieties may be combined together with the atoms to which they are attached and joined to form an optionally substituted 5- to 7-membered ring that incorporates a sulfinyl (—S[O]—) moiety.

In further embodiments, the compounds of the present invention have structural Formula I, $R_1$ is selected from the group consisting of hydrogen, and Q is selected from hydrogen, methyl, ethyl, n-propyl, isopropyl, n-butyl, 2-methyl-1-propyl, sec-butyl, tert-butyl, 2,3-dimethylbutan-2-yl, cyclohexyl, 2,6-dimethylcyclohexyl, 1-methylcyclohexyl, phenyl, 4-pyridyl, benzyl, 4-pyridylmethyl, phenylethyl, (S)-1-hydroxy-(phenylethyl), 2-pyrazinyl, phenylethenyl, (E)-2-(4-pyridazinyl)-1-ethenyl, (E)-4-(2-)-1H-imidazolyl-1-ethenyl, 3-acetoxyl-1-propyl, ethoxycarbonylethyl, methoxylcarbonylpropyl, N-methylaminocarbonylethyl, N-ethylaminocarbonylpropyl, 3-(N-ethylaminocarbonyl)-2,2-dimethyl-1-propyl, N-(morpholinoethyl)aminocarbonylethyl, 3-pyridylmethylaminocarbonylethyl, 4-pyridylmethyl aminocarbonylethyl, 4-pyridylmethylaminocarbonylpropyl, carboxyethyl, carboxypropyl, 2-piperidinyl, 3-piperidinyl, 4-piperidinyl, 2-piperazinyl, (S)-1-aminoethyl, (R)-1-aminoethyl, (S)-1-aminoisobutyl, 1-aminocyclopropyl, methoxy, ethoxy, isopropoxy, isobutoxy, neopentyloxy, cyclohexyloxy, 4-piperidinyloxy, 3-acetoxy-2-methyl-1-propoxy, tert-pentyloxy, 4-acetoxybenzyloxy, 3-(4-acetoxyphenyl)-2-propenyloxy, (E)-2-methyl-4-(2-oxo-2,3-dihydrobenzofuran-5-yl)but-3-en-2-yloxy, pivaloyloxymethoxy, pivaloyloxy-1-ethoxy, isopropoxycarbonyloxymethoxy, isopropoxycarbonyloxy-1-ethoxy, amino, N-methylamino, N-ethylamino, N,N-dimethylamino, N-propylamino, N-isopropylamino, N-butylamino, N-piperidinyl, N-piperazinyl, N-4-methylpiperazinyl, N-cyclohexylamino, N-benzylamino, N-(2,4-dimethoxy)benzylamino, 2-(N-methylcarboxamido)phenylamino, N-methyl-2-hydroxyethylamino, $N^1,N^2$-dimethyl-1,2-ethanediamin-1-yl, $N^1,N^2$-diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl.

$R_2$ to $R_5$ are independently selected from the group consisting of hydrogen, duterium, F, Cl, CN, methyl, ethyl, n-propyl, isopropyl, n-hexyl, cyclopropyl, methoxy, ethoxy, isopropoxy, trifluoromethyl, tetrafluoroethoxy, methylthio, and t-butylthio, any of which may be optionally substituted.

According to an aspect of this invention, $R_6$ is selected from the group consisting of methylsulfinyl, ethylsulfinyl, isopropylsulfinyl, methylsulfinylmethyl, 2-(ethylsulfinyl)ethyl, t-butylsulfinylmethyl, cyclopropylsulfinyl, cyclopentylsulfinyl, phenylsulfinyl, benzylsulfinyl, phenethylsulfinyl, 2-pyridylsulfinyl, 2-pyrazinylsulfinyl, 4-thiazolylsulfinyl, 4-pyridylmethylsulfinyl, 3-thienylmethylsulfinyl, 4-piperidinylsulfinyl, tetrahydro-2H-pyranylsulfinyl, any of which may be optionally substituted and $R_7$ is hydrogen.

In yet another embodiment, the compounds of the present invention have structural Formula I. Accordingly, $R_1$ is selected from the group consisting of hydrogen and $R_8$ and $R_9$ in Q-C(=O)— is selected from the group consisting of methyl, ethyl, ethoxy, isopropoxy, isobutoxy, phenyl, phenylethenyl, 4-piperidinyl, N-piperazinyl, N-(2,4-dimethoxy)benzylamino, 2-(N-methylcarboxamido)-phenylamino, $N^1,N^2$-dimethyl-1,2-ethanediamin-1-yl, $N^1,N^2$-diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl.

$R_2$ to $R_5$ are independently selected from the group consisting of hydrogen, F, Cl, methyl, ethyl, cyclopropyl, methoxy, ethoxy, trifluoromethyl and methylthio, any of which may be optionally substituted.

$R_6$ is selected from the group consisting of methylsulfinyl, ethylsulfinyl, isopropylsulfinyl, methylsulfinylmethyl, t-butylsulfinylmethyl, cyclopropylsulfinyl, and benzylsulfinyl and $R_7$ is hydrogen.

In certain embodiments, the compounds of the present invention have structural Formula I, wherein $R_1$ is selected from the group consisting of hydrogen and Q-C(=O)—, and $R_8$ is methyl. $R_2$ through $R_5$ are each hydrogen. Substituent $R_6$ is methylsulfinyl and $R_7$ is hydrogen.

In other embodiments, the compounds of the present invention have structural Formula I, wherein $R_1$ is selected from the group consisting of hydrogen and Q-C(=O)—, any of which may be optionally substituted.

$R_2$ to $R_5$ are independently selected from the group consisting of hydrogen, D, F, Cl, Br, CN, $(C_1$-$C_6)$-alkyl, $(C_3$-$C_6)$-cycloalkyl, $(C_1$-$C_6)$-alkoxy, $(C_1$-$C_3)$-haloalkyl, $(C_1$-$C_4)$-perhaloalkyl, $(C_1$-$C_4)$-perhaloalkoxy, and $(C_1$-$C_6)$-alkylthio, any of which may be optionally substituted.

$R_6$ is hydrogen and $R_7$ is independently selected from the group consisting of $(C_1-C_6)$-alkylsulfinyl, $(C_1-C_6)$-alkylsulfinylalkyl, $(C_3-C_6)$-cycloalkylsulfinyl, arylsulfinyl, arylalkylsulfinyl, heteroarylsulfinyl, heteroarylalkylsulfinyl, and heterocycloalkylsulfinyl, any of which may be optionally substituted; or the $R_6$ and $R_7$ moieties may be combined together with the atoms to which they are attached and joined to form an optionally substituted 5- to 7-membered ring that incorporates a sulfinyl (—S[O]—) moiety.

Q is $R_8$, $OR_8$, $NHR_8$, or $NR_8R_9$; $R_8$ and $R_9$ are independently selected from the group consisting of hydrogen, $(C_1-C_{12})$-alkyl, $(C_2-C_{12})$-alkenyl, $(C_3-C_8)$-cycloalkyl, aryl, arylalkyl, arylalkenyl, heterocycloalkyl, heteroaryl, heteroarylalkyl, and heteroarylalkenyl, any of which may be optionally substituted; or $R_8$ and $R_9$, together with the atoms to which they are attached, may be joined to form an optionally substituted 5- to 7-membered heterocycloalkyl ring; any of which may be optionally substituted.

In further embodiments, the inventive compounds conform to Formula I, with substituent $R_1$ selected from the group consisting of hydrogen, and Q is selected from hydrogen, methyl, ethyl, n-propyl, isopropyl, n-butyl, 2-methyl-1-propyl, sec-butyl, tert-butyl, 2,3-dimethylbutan-2-yl, cyclohexyl, 2,6-dimethylcyclohexyl, 1-methylcyclohexyl, phenyl, 4-pyridyl, benzyl, 4-pyridylmethyl, phenylethyl, (S)-1-hydroxy-(phenylethyl), 2-pyrazinyl, phenylethenyl, (E)-2-(4-pyridazinyl)-1-ethenyl, (E)-4-(2-)-1H-imidazolyl-1-ethenyl, 3-acetoxyl-1-propyl, ethoxycarbonylethyl, methoxylcarbonylpropyl, N-methylaminocarbonylethyl, N-ethylaminocarbonylpropyl, 3-(N-ethylaminocarbonyl)-2,2-dimethyl-1-propyl, N-(morpholinoethyl)aminocarbonylethyl, 3-pyridylmethylaminocarbonylethyl, 4-pyridylmethylaminocarbonylethyl, 4-pyridylmethylaminocarbonylpropyl, carboxyethyl, carboxypropyl, 2-piperidinyl, 3-piperidinyl, 4-piperidinyl, 2-piperazinyl, (S)-1-aminoethyl, (R)-1-aminoethyl, (S)-1-aminoisobutyl, 1-aminocyclopropyl, methoxy, ethoxy, isopropoxy, isobutoxy, neopentyloxy, cyclohexyloxy, 4-piperidinyloxy, 3-acetoxy-2-methyl-1-propoxy, tert-pentyloxy, 4-acetoxybenzyloxy, 3-(4-acetoxyphenyl)-2-propenyloxy, (E)-2-methyl-4-(2-oxo-2,3-dihydrobenzofuran-5-yl)but-3-en-2-yloxy, pivaloyloxymethoxy, pivaloyloxy-1-ethoxy, isopropoxycarbonyloxymethoxy, isopropoxycarbonyloxy-1-ethoxy, amino, N-methylamino, N-ethylamino, N,N-dimethylamino, N-propylamino, N-isopropylamino, N-butylamino, N-piperidinyl, N-piperazinyl, N-4-methylpiperazinyl, N-cyclohexylamino, N-benzylamino, N-(2,4-dimethoxy)benzylamino, 2-(N-methylcarboxamido)phenylamino, N-methyl-2-hydroxyethylamino, $N^1,N^2$-dimethyl-1,2-ethanediamin-1-yl, $N^1,N^2$-diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl.

$R_2$ to $R_5$ are independently selected from the group consisting of hydrogen, D, F, Cl, Br, CN, $(C_1-C_6)$-alkyl, $(C_3-C_6)$-cycloalkyl, $(C_1-C_6)$-alkoxy, $(C_1-C_3)$-haloalkyl, $(C_1-C_4)$-perhaloalkyl, $(C_1-C_4)$-perhaloalkoxy, and $(C_1-C_6)$-alkylthio, any of which may be optionally substituted.

$R_6$ is hydrogen and $R_7$ is independently selected from the group consisting of $(C_1-C_6)$-alkylsulfinyl, $(C_1-C_6)$-alkylsulfinylalkyl, $(C_3-C_6)$-cycloalkylsulfinyl, arylsulfinyl, arylalkylsulfinyl, heteroarylsulfinyl, heteroarylalkylsulfinyl, and heterocycloalkylsulfinyl, any of which may be optionally substituted.

Alternatively, $R_6$ and $R_7$ moieties may be combined together with the atoms to which they are attached and joined to form an optionally substituted 5- to 7-membered ring that incorporates a sulfinyl (—S[O]—) moiety.

In further embodiments, for Formula I compounds $R_1$ is selected from the group consisting of hydrogen, and Q is selected from hydrogen, methyl, ethyl, n-propyl, isopropyl, n-butyl, 2-methyl-1-propyl, sec-butyl, tert-butyl, 2,3-dimethylbutan-2-yl, cyclohexyl, 2,6-dimethylcyclohexyl, 1-methylcyclohexyl, phenyl, 4-pyridyl, benzyl, 4-pyridylmethyl, phenylethyl, (S)-1-hydroxy-(phenylethyl), 2-pyrazinyl, phenylethenyl, (E)-2-(4-pyridazinyl)-1-ethenyl, (E)-4-(2-)-1H-imidazolyl-1-ethenyl, 3-acetoxyl-1-propyl, ethoxycarbonylethyl, methoxylcarbonylpropyl, N-methylaminocarbonylethyl, N-ethylaminocarbonylpropyl, 3-(N-ethylaminocarbonyl)-2,2-dimethyl-1-propyl, N-(morpholinoethyl)aminocarbonylethyl, 3-pyridylmethylaminocarbonylethyl, 4-pyridylmethylaminocarbonylethyl, 4-pyridylmethylaminocarbonylpropyl, carboxyethyl, carboxypropyl, 2-piperidinyl, 3-piperidinyl, 4-piperidinyl, 2-piperazinyl, (S)-1-aminoethyl, (R)-1-aminoethyl, (S)-1-aminoisobutyl, 1-aminocyclopropyl, methoxy, ethoxy, isopropoxy, isobutoxy, neopentyloxy, cyclohexyloxy, 4-piperidinyloxy, 3-acetoxy-2-methyl-1-propoxy, tert-pentyloxy, 4-acetoxybenzyloxy, 3-(4-acetoxyphenyl)-2-propenyloxy, (E)-2-methyl-4-(2-oxo-2,3-dihydrobenzofuran-5-yl)but-3-en-2-yloxy, pivaloyloxymethoxy, pivaloyloxy-1-ethoxy, isopropoxycarbonyloxymethoxy, isopropoxycarbonyloxy-1-ethoxy, amino, N-methylamino, N-ethylamino, N,N-dimethylamino, N-propylamino, N-isopropylamino, N-butylamino, N-piperidinyl, N-piperazinyl, N-4-methylpiperazinyl, N-cyclohexylamino, N-benzylamino, N-(2,4-dimethoxy)benzylamino, 2-(N-methylcarboxamido)phenylamino, N-methyl-2-hydroxyethylamino, $N^1,N^2$-dimethyl-1,2-ethanediamin-1-yl, $N^1,N^2$-diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl;

$R_2$ to $R_5$ are independently selected from the group consisting of hydrogen, D, F, Cl, CN, methyl, ethyl, n-propyl, isopropyl, n-hexyl, cyclopropyl, methoxy, ethoxy, isopropoxy, trifluoromethyl, tetrafluoroethoxy, methylthio, and t-butylthio, any of which may be optionally substituted.

$R_7$ is selected from the group consisting of methylsulfinyl, ethylsulfinyl, isopropylsulfinyl, methylsulfinylmethyl, 2-(ethylsulfinyl)ethyl, t-butylsulfinylmethyl, cyclopropylsulfinyl, cyclopentylsulfinyl, phenylsulfinyl, benzylsulfinyl, phenethylsulfinyl, 2-pyridylsulfinyl, 2-pyrazinylsulfinyl, 4-thiazolylsulfinyl, 4-pyridylmethylsulfinyl, 3-thienylmethylsulfinyl, 4-piperidinylsulfinyl, tetrahydro-2H-pyranylsulfinyl, any of which may be optionally substituted and $R_6$ is hydrogen.

In further embodiments, the compounds of the present invention have structural Formula I, wherein $R_1$ is selected from the group consisting of hydrogen and $R_8$ and $R_9$ in Q-C(=O)— is selected from the group consisting of methyl, ethyl, ethoxy, isopropoxy, isobutoxy, phenyl, phenylethenyl, 4-piperidinyl, N-piperazinyl, N-(2,4-dimethoxy)benzylamino, 2-(N-methylcarboxamido)-phenylamino, $N^1,N^2$-dimethyl-1,2-ethanediamin-1-yl, $N^1,N^2$-diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl.

$R_2$ to $R_5$ are independently selected from the group consisting of hydrogen, F, Cl, methyl, ethyl, cyclopropyl, methoxy, ethoxy, trifluoromethyl and methylthio, any of which may be optionally substituted.

$R_7$ is selected from the group consisting of methylsulfinyl, ethylsulfinyl, isopropylsulfinyl, methylsulfinylmethyl, t-butylsulfinylmethyl, cyclopropylsulfinyl, and benzylsulfinyl and $R_6$ is hydrogen.

Compounds in accordance with the present invention include the following without limitation:
2-(5-(methylsulfinyl)thiazol-2-ylcarbamoyl)phenyl acetate
2-hydroxy-N-(5-(methylsulfinyl)thiazol-2-yl)benzamide
sodium 2-(5-(methylsulfinyl)thiazol-2-ylcarbamoyl)phenolate
3-(5-(methylsulfinyl)thiazol-2-ylcarbamoyl)phenyl acetate
3-hydroxy-N-(5-(methylsulfinyl)thiazol-2-yl)benzamide
4-(5-(methylsulfinyl)thiazol-2-ylcarbamoyl)phenyl acetate
4-hydroxy-N-(5-(methylsulfinyl)thiazol-2-yl)benzamide
2-(5-(ethylsulfinyl)thiazol-2-ylcarbamoyl)phenyl acetate
N-(5-(ethylsulfinyl)thiazol-2-yl)-2-hydroxy benzamide
2-(5-(isopropylsulfinyl)thiazol-2-ylcarbamoyl)phenyl acetate
2-hydroxy-N-(5-(isopropylsulfinyl)thiazol-2-yl)benzamide
2-(5-(butylsulfinyl)thiazol-2-ylcarbamoyl)phenyl acetate
2-hydroxy-N-(5-(butylsulfinyl)thiazol-2-yl)benzamide
2-(5-(cyclohexylsulfinyl)thiazol-2-ylcarbamoyl)phenyl acetate
N-(5-(cyclohexylsulfinyl)thiazol-2-yl)-2-hydroxybenzamide
2-(5-(phenylsulfinyl)thiazol-2-ylcarbamoyl)phenyl acetate
2-hydroxy-N-(5-(phenylsulfinyl)thiazol-2-yl)benzamide
2-(5-(benzylsulfinyl)thiazol-2-ylcarbamoyl)phenyl acetate
N-(5-(benzylsulfinyl)thiazol-2-yl)-2-hydroxybenzamide
4-methyl-2-(5-(methylsulfinyl)thiazol-2-ylcarbamoyl)phenyl acetate
2-hydroxy-5-methyl-N-(5-(methylsulfinyl)thiazol-2-yl)benzamide
4-(4-fluorobenzyloxy)-2-(5-(methylsulfinyl)thiazol-2-ylcarbamoyl)phenyl acetate
5-(4-fluorobenzyloxy)-2-hydroxy-N-(5-(methylsulfinyl)thiazol-2-yl)benzamide
2-(4-(methylsulfinyl)thiazol-2-ylcarbamoyl)phenyl acetate
2-hydroxy-N-(4-(methylsulfinyl)thiazol-2-yl)benzamide
sodium 2-(4-(methylsulfinyl)thiazol-2-ylcarbamoyl)phenolate
3-(4-(methylsulfinyl)thiazol-2-ylcarbamoyl)phenyl acetate
3-hydroxy-N-(4-(methylsulfinyl)thiazol-2-yl)benzamide
4-(4-(methylsulfinyl)thiazol-2-ylcarbamoyl)phenyl acetate
4-hydroxy-N-(4-(methylsulfinyl)thiazol-2-yl)benzamide
2-(4-(ethylsulfinyl)thiazol-2-ylcarbamoyl)phenyl acetate
N-(4-(ethylsulfinyl)thiazol-2-yl)-2-hydroxybenzamide
2-(4-(isopropylsulfinyl)thiazol-2-ylcarbamoyl)phenyl acetate
2-hydroxy-N-(4-(isopropylsulfinyl)thiazol-2-yl)benzamide
2-(4-(cyclohexylsulfinyl)thiazol-2-ylcarbamoyl)phenyl acetate
N-(4-(cyclohexylsulfinyl)thiazol-2-yl)-2-hydroxybenzamide
2-(4-(benzylsulfinyl)thiazol-2-ylcarbamoyl)phenyl acetate
N-(4-(benzylsulfinyl)thiazol-2-yl)-2-hydroxybenzamide
2-(4-(phenylsulfinyl)thiazol-2-ylcarbamoyl)phenyl acetate
2-hydroxy-N-(4-(phenylsulfinyl)thiazol-2-yl)benzamide
4-methyl-2-(4-(methylsulfinyl)thiazol-2-ylcarbamoyl)phenyl acetate
2-hydroxy-5-methyl-N-(4-(methylsulfinyl)thiazol-2-yl)benzamide
4-(4-fluorobenzyloxy)-2-(4-(methylsulfinyl)thiazol-2-ylcarbamoyl)phenyl acetate
5-(4-fluorobenzyloxy)-2-hydroxy-N-(4-(methylsulfinyl)thiazol-2-yl)benzamide The term "salts" is used in its broadest sense. For example, the term salts includes hydrogen salts and hydroxide salts with ions of the present compound. In some embodiments, the term salt may be a subclass referred to as pharmaceutically acceptable salts, which are salts of the present compounds having a pharmacological activity and which are neither biologically nor otherwise undesirable. In all embodiments, the salts can be formed with acids, such as, without limitation, hydrogen, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycero-phosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. In all embodiments, the salts can be formed with bases, such as, without limitation, hydroxide, ammonium salts, alkali metal salts such as lithium, sodium and potassium salts, alkaline earth metal salts such as calcium, magnesium salts, aluminum salts, salts with organic bases such as ammonia, methylamine, diethylamine, ethanolamine, dicyclohexylamine, N-methylmorpholine, N-methyl-D-glucamine, and salts with amino acids such as arginine and lysine. Basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The term "therapeutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethanesulfonate (isethionate), lactate, maleate, malonate, DL-mandelate, mesitylenesulfonate, methanesulfonate, naphthalenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reacting a carboxy, phenol or similar group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "solvates" is used in its broadest sense. For example, the term solvates includes hydrates formed when a compound of the present invention contains one or more bound water molecules.

As used in the present specification the following terms have the meanings indicated:

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. Examples of acyl groups include formyl, alkanoyl and aroyl radicals.

The term "acylamino" embraces an amino radical substituted with an acyl group. An example of an "acylamino" radical is acetylamino (CH$_3$C(O)NH—).

The term "alkenyl," as used herein, alone or in combination, refers to a straight-chain, branched-chain, and cyclic unsaturated hydrocarbon radical having one or more double bonds and containing from 2 to 20, preferably 2 to 6, carbon atoms. The term "alkenyl groups" is used in its broadest sense. Alkenylene refers to a carbon-carbon double bond system attached at two or more positions such as ethenylene [(—CH═CH—), (—C::C—)]. For example, (C$_2$-C$_8$) alkenyl groups embraces straight, branched, and cyclic hydrocarbon chains containing 2 to 8 carbon atoms having at least one double bond, Examples of suitable alkenyl radicals include ethenyl, propenyl, iso-propenyl, butenyl, iso-butenyl, sec-butenyl, tert-butenyl, n-pentenyl, n-hexenyl, and the like, unless otherwise indicated.

The term "alkenylsulfinyl," as used herein, alone or in combination, refers to a straight-chain, branched-chain, and cyclic unsaturated hydrocarbon radical having one or more double bonds and containing from 2 to 20, preferably 2 to 6, carbon atoms that are attached to the parent molecular moiety through a sulfinyl group (—S[O]—). The term "alkenylsulfinyl group" is used in its broadest sense. For example, (C$_2$-C$_8$) alkenylsulfinyl groups embrace straight, branched, and cyclic hydrocarbon chains containing 2 to 8 carbon atoms having at least one double bond and are attached to the parent molecular moiety through a sulfinyl group (—S[O]—). Examples of suitable alkenylsulfinyl radicals include ethenylsulfinyl, propenylsulfinyl, iso-propenyl sulfinyl, butenylsulfinyl, iso-butenylsulfinyl, sec-butenylsulfinyl, tert-butenylsulfinyl, n-pentenylsulfinyl, n-hexenylsulfinyl, and the like, unless otherwise indicated.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkoxyalkoxy," as used herein, alone or in combination, refers to one or more alkoxy groups attached to the parent molecular moiety through another alkoxy group. Examples include ethoxyethoxy, methoxypropoxyethoxy, ethoxypentoxyethoxyethoxy and the like.

The term "alkoxyalkyl," as used herein, alone or in combination, refers to an alkoxy group attached to the parent molecular moiety through an alkyl group. The term "alkoxyalkyl" also embraces alkoxyalkyl groups having one or more alkoxy groups attached to the alkyl group, that is, to form monoalkoxyalkyl and dialkoxyalkyl groups.

The term "alkoxycarbonyl," as used herein, alone or in combination, refers to an alkoxy group attached to the parent molecular moiety through a carbonyl group.

Examples of such "alkoxycarbonyl" groups include methoxycarbonyl, ethoxycarbonyl, propoxycarbonyl, butoxycarbonyl and hexyloxycarbonyl.

The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl.

The term "alkyl," as used herein, alone or in combination, refers to a straight-chain or branched-chain alkyl radical containing from 1 to and including 20, preferably 1 to 10, and more preferably 1 to 6, carbon atoms. The term "alkyl groups" is used in its broadest sense. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. For example, the O(C$_1$-C$_8$)-alkyl groups comprises the straight O(C$_1$-C$_8$)-alkyl groups as well as the branched O(C$_1$-C$_8$)-alkyl groups. For another example, the term comprises cycloalkyl groups, as for example, the (C$_1$-C$_8$)-alkyl groups comprises the (C$_3$-C$_8$)-cycloalkyl groups.

The term "alkylene," as used herein, alone or in combination, refers to a saturated aliphatic group derived from a straight or branched chain saturated hydrocarbon attached at two or more positions, such as methylene (—CH$_2$—).

The term "alkylamino," as used herein, alone or in combination, refers to an amino group attached to the parent molecular moiety through an alkyl group.

The term "alkylaminocarbonyl" as used herein, alone or in combination, refers to an alkylamino group attached to the parent molecular moiety through a carbonyl group. Examples of such radicals include N-methylaminocarbonyl and N,N-dimethylcarbonyl.

The term "alkylcarbonyl" and "alkanoyl," as used herein, alone or in combination, refers to an alkyl group attached to the parent molecular moiety through a carbonyl group. Examples of such groups include methylcarbonyl and ethylcarbonyl.

The term "alkylidene," as used herein, alone or in combination, refers to an alkenyl group in which one carbon atom of the carbon-carbon double bond belongs to the moiety to which the alkenyl group is attached.

The term "alkylsulfinyl," as used herein, alone or in combination, refers to an alkyl group attached to the parent molecular moiety through a sulfinyl group (RS[O]—). Examples of alkylsulfinyl groups include methylsulfinyl, ethylsulfinyl, butylsulfinyl and the like.

The term "alkylsulfinylalkyl," as used herein, alone or in combination, refers to an alkyl sulfinyl group (RS[O]—) attached to the parent molecular moiety through a alkyl group. Examples of alkylsulfinylalkyl groups include methylsulfinylmethyl, ethylsulfinylmethyl, 2-(butylsulfinyl)-ethyl and the like.

The term "alkylsulfonyl," as used herein, alone or in combination, refers to an alkyl group attached to the parent molecular moiety through a sulfonyl group ($RSO_2$—). Examples of alkylsulfonyl groups include methanesulfonyl, ethanesulfonyl, tert-butanesulfonyl, benzylsulfonyl and the like.

The term "alkylthio," as used herein, alone or in combination, refers to an alkyl thioether (R—S—) radical wherein the term alkyl is as defined above. Examples of suitable alkyl thioether radicals include methylthio, ethylthio, n-propylthio, isopropylthio, n-butylthio, iso-butylthio, sec-butylthio, tert-butylthio, ethoxyethylthio, methoxypropoxyethylthio, ethoxypentoxyethoxyethylthio and the like.

The term "alkylthioalkyl" embraces alkylthio radicals attached to an alkyl radical. Alkylthioalkyl radicals include "lower alkylthioalkyl" radicals having alkyl radicals of one to six carbon atoms and an alkylthio radical as described above. Examples of such radicals include methylthiomethyl.

The term "alkynyl," as used herein in its broadest sense, alone or in combination, refers to a straight-chain, branched chain hydrocarbon and cyclic unsaturated hydrocarbon radicals having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). For example, ($C_2$-$C_8$) alkynyl groups embraces straight, branched, and cyclic hydrocarbon chains containing 2 to 8 carbon atoms having at least one triple bond, and the term includes but is not limited to substituents such as ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl, and the like, unless otherwise indicated.

The term "alkynylsulfinyl," as used herein in its broadest sense, alone or in combination, refers to a straight-chain, branched chain hydrocarbon and cyclic unsaturated hydrocarbon radicals having one or more triple bonds and containing from 2 to 20, preferably from 2 to 6, more preferably from 2 to 4, carbon atoms that are attached to the parent molecular moiety through a sulfinyl group (RS[O]—). For example, ($C_2$-$C_8$) alkynylsulfinyl groups embraces straight, branched, and cyclic hydrocarbon chains containing 2 to 8 carbon atoms having at least one triple bond, and the term includes but is not limited to substituents such as ethynylsulfinyl, 2-propynylsulfinyl, 3-hydroxyl-1-propynylsulfinyl, 1-butynylsulfinyl, 3-butynylsulfinyl, 1-pentynylsulfinyl, 2-pentynylsulfinyl, 4-methoxy-2-pentynylsulfinyl, 3-methyl-1-butynylsulfinyl, 1-hexynylsulfinyl, 3,3-dimethyl-1-butynylsulfinyl, and the like, unless otherwise indicated.

The term "amido," as used herein, alone or in combination, refers to an amino group as described below attached to the parent molecular moiety through a carbonyl group. The term "C-amido" as used herein, alone or in combination, refers to a —C(=O)—$NR_2$ group with R as defined herein. The term "N-amido" as used herein, alone or in combination, refers to a RC(=O)NH— group, with R as defined herein. The term "amino," as used herein, alone or in combination, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl, heteroarylalkenyl, heteroarylalkyl, heterocycle, heterocycloalkenyl, and heterocycloalkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the heterocycloalkenyl and the heterocycloalkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxy-alkyl, nitro, and oxo.

The term "aminoalkyl," as used herein, alone or in combination, refers to an amino group attached to the parent molecular moiety through an alkyl group. Examples include aminomethyl, aminoethyl and aminobutyl. The term "alkylamino" denotes amino groups which have been substituted with one or two alkyl radicals. Suitable "alkylamino" groups may be mono- or dialkylated, forming groups such as, for example, N-methylamino, N-ethylamino, N,N-dimethylamino, N,N-diethylamino and the like.

The terms "aminocarbonyl" and "carbamoyl," as used herein, alone or in combination, refer to an amino-substituted carbonyl group, wherein the amino group can be a primary or secondary amino group containing substituents selected from alkyl, aryl, aralkyl, cycloalkyl, cycloalkylalkyl radicals and the like.

The term "aminocarbonylalkyl," as used herein, alone or in combination, refers to an aminocarbonyl radical attached to an alkyl radical, as described above. An example of such radicals is aminocarbonylmethyl. The term "amidino" denotes an —C(NH)$NH_2$ radical. The term "cyanoamidino" denotes an —C(N—CN)$NH_2$ radical.

The term "aralkenyl" or "arylalkenyl," as used herein, alone or in combination, refers to an aryl group attached to the parent molecular moiety through an alkenyl group.

The term "aralkenylsulfinyl" or "arylalkenylsulfinyl," as used herein, alone or in combination, refers to an aryl alkenyl group attached to the parent molecular moiety through a sulfinyl group (—S[O]—).

The term "aralkoxy" or "arylalkoxy," as used herein, alone or in combination, refers to an aryl group attached to the parent molecular moiety through an alkoxy group.

The term "aralkyl" or "arylalkyl," as used herein, alone or in combination, refers to an aryl group attached to the parent molecular moiety through an alkyl group.

The term "aralkylsulfinyl" or "arylalkylsulfinyl," as used herein, alone or in combination, refers to an arylalkyl group attached to the parent molecular moiety through a sulfinyl group (—S[O]—).

The term "aralkylamino" or "arylalkylamino," as used herein, alone or in combination, refers to an arylalkyl group attached to the parent molecular moiety through a nitrogen atom, wherein the nitrogen atom is substituted with hydrogen.

The term "aralkylidene" or "arylalkylidene," as used herein, alone or in combination, refers to an aryl group attached to the parent molecular moiety through an alkylidene group The term "aralkylthio" or "arylalkylthio," as used herein, alone or in combination, refers to an arylalkyl group attached to the parent molecular moiety through a sulfur atom.

The term "aralkynyl" or "arylalkynyl," as used herein, alone or in combination, refers to an aryl group attached to the parent molecular moiety through an alkynyl group.

The term "aralkoxycarbonyl," as used herein, alone or in combination, refers to a radical of the formula aralkyl-O—C(O)— in which the term "aralkyl," has the significance given above. Examples of an aralkoxycarbonyl radical are benzyloxycarbonyl (Z or Cbz) and 4-methoxyphenylmethoxycarbonyl (MOS).

The term "aralkanoyl," as used herein, alone or in combination, refers to an acyl radical derived from an aryl-substituted alkanecarboxylic acid such as benzoyl, phenylacetyl, 3-phenylpropionyl(hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" refers to an acyl radical derived from an arylcarboxylic acid, "aryl" having the meaning given below. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aryl," as used herein, alone or in combination, means a carbocyclic aromatic system containing one, two or three rings wherein such rings may be attached together in a pendent manner or may be fused. The term "aryl" embraces aromatic radicals such as phenyl, naphthyl, anthracenyl, phenanthryl, and biphenyl. The aryl groups of the present invention can be optionally substituted with one, two, three, four, or five substituents independently selected from the groups as defined herein.

The term "arylamino" as used herein, alone or in combination, refers to an aryl group attached to the parent moiety through an amino group, such as N-phenylamino, and the like.

The terms "arylcarbonyl" and "aroyl," as used herein, alone or in combination, refer to an aryl group attached to the parent molecular moiety through a carbonyl group.

The term "aryloxy," as used herein, alone or in combination, refers to an aryl group attached to the parent molecular moiety through an oxygen atom.

The term "arylsulfinyl," as used herein, alone or in combination, means a carbocyclic aromatic system containing one, two or three rings wherein such rings may be attached together in a pendent manner or may be fused, which is attached to the parent molecular moiety through a sulfinyl group (—S[O]—). The term "arylsulfinyl" embraces aromatic radicals such as phenylsulfinyl, naphthylsulfinyl, anthracenylsulfinyl, phenanthrylsulfinyl, and biphenylsulfinyl. The aryl groups of the present invention can be optionally substituted with one, two, three, four, or five substituents independently selected from the groups as defined herein.

The term "arylsulfonyl," as used herein, alone or in combination, refers to an aryl group attached to the parent molecular moiety through a sulfonyl group.

The term "arylthio," as used herein, alone or in combination, refers to an aryl group attached to the parent molecular moiety through a sulfur atom.

The terms "carboxy" or "carboxyl", whether used alone or with other terms, such as "carboxyalkyl", denotes —CO$_2$H.

The terms "benzo" and "benz," as used herein, alone or in combination, refer to the divalent radical C$_6$H$_4$=derived from benzene. Examples include benzothiophene and benzimidazole.

The term "carbamoyloxy," as used herein, alone or in combination, refers to an amino-substituted carbonyl group attached to the parent molecular moiety through a oxygen atom (e.g. RR'NC(=O)O—), wherein the amino group can be a primary or secondary amino group containing substituents selected from alkyl, aryl, aralkyl, cycloalkyl, cycloalkylalkyl radicals and the like.

The term "O-carbamyl" as used herein, alone or in combination, refers to a —OC(O)NR, group-with R as defined herein.

The term "C-linked" as used herein, alone or in combination, refers to any substituent that is attached to the parent molecular moiety through a carbon-carbon bond.

The term "N-carbamyl" as used herein, alone or in combination, refers to a ROC(O)NH— group, with R as defined herein.

The term "carbonate" as used herein, alone or in combination, refers to a —O—C(=O)OR group, with R as defined herein.

The term "carbonyl," as used herein, when alone includes formyl [—C(O)H] and in combination is a —C(O)— group.

The term "carboxy," as used herein, refers to —C(O)OH or the corresponding "carboxylate" such as a carboxylic acid salt derivative or ester derivative. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably three to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronapthalene, octahydronapthalene as well as the multicyclic (multi-centered) saturated or partially unsaturated type. The latter type of isomer is exemplified in general by bicyclo[2,2,2]octane, bicyclo[2,2,2]octane, bicyclo[1,1,1]pentane, camphor and bicyclo[3,2,1]octane.

The term "cycloalkylsulfinyl," as used herein, alone or in combination, refers to a saturated or partially saturated monocyclic, bicyclic or tricyclic alkyl radical wherein each cyclic moiety contains from 3 to 12, preferably three to seven, carbon atom ring members and which may optionally be a benzo fused ring system which is optionally substituted as defined herein that is attached to the parent molecular moiety through a sulfinyl group (—S[O]—). Examples of such cycloalkylsulfinyl radicals include cyclopropylsulfinyl, cyclobutylsulfinyl, cyclopentylsulfinyl, cyclohexylsulfinyl, cycloheptylsulfinyl, octahydronaphthylsulfinyl, 2,3-dihydro-1H-indenylsulfinyl, adamantylsulfinyl and the like. "Bicyclic" and "tricyclic" as used herein are intended to include both fused ring systems, such as decahydronapthalene, octahydronapthalene as well as the multicyclic (multicentered) saturated or partially unsaturated type. The latter type of isomer is exemplified in general by bicyclo[2,2,2]octane, bicyclo[2,2,2]octane, bicyclo[1,1,1]pentane, camphor and bicyclo[3,2,1]octane.

The term "cycloalkenyl," as used herein, alone or in combination, refers to a partially unsaturated monocyclic, bicyclic or tricyclic radical wherein each cyclic moiety contains from 3 to 12, preferably five to eight, carbon atom ring members and which may optionally be a benzo fused ring system which is optionally substituted as defined herein. Examples of such cycloalkenyl radicals include cyclopentenyl, cyclohexenyl, cyclohexadienyl, cycloheptenyl, cyclooctadienyl, -1H-indenyl and the like.

The term "cycloalkenylsulfinyl," as used herein, alone or in combination, refers to a partially unsaturated monocyclic, bicyclic or tricyclic radical wherein each cyclic moiety contains from 3 to 12, preferably five to eight, carbon atom ring members as defined herein that is attached to the parent molecular moiety through a sulfinyl group (—S[O]—). Examples of such cycloalkenylsulfinyl radicals include 1-cyclopentenylsulfinyl, 3-cyclopentenylsulfinyl, 4-cyclohexenylsulfinyl 1,4-cyclohexadienylsulfinyl, 3-cycloheptenylsulfinyl, 1,5-cyclooctadienylsulfinyl and the like.

The term "cycloalkylalkyl," as used herein, alone or in combination, refers to an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "cycloalkenylalkyl," as used herein, alone or in combination, refers to an alkyl radical as defined above which is substituted by a cycloalkenyl radical as defined above. Examples of such cycloalkenylalkyl radicals include 1-methylcyclohex-1-enyl-, 4-ethylcyclohex-1-enyl-, 1-butylcyclopent-1-enyl-, 3-methylcyclopent-1-enyl- and the like.

The term "ester," as used herein, alone or in combination, refers to a carbonyloxy —(C=O)O— group bridging two moieties linked at carbon atoms. Examples include ethyl benzoate, n-butyl cinnamate, phenyl acetate and the like.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, trichloroethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a halohydrocarbyl group attached at two or more positions. Examples include fluoromethylene (—CFH—), difluoromethylene (—CF$_2$—), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2-NH—OCH3.

The term "heteroaryl," as used herein, alone or in combination, refers to an aromatic five- or six-membered ring, where at least one atom is selected from the group consisting of N, O, and S, and the remaining ring atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes systems where a heteroaryl ring is fused to an aryl group, as defined herein, a heterocycle group, as defined herein, or an additional heteroaryl group. Heteroaryls are exemplified by benzothienyl, benzoxazolyl, benzofuranyl, benzimidazolyl, benzthiazolyl benzotriazolyl, cinnolinyl, furyl, imidazolyl, triazolyl [e.g., 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], indazolyl, indolyl, isoxazolyl, isoquinolinyl, isothiazolyl, naphthyridinyl, oxadiazolyl [e.g., 1,2,4-oxadiazolyl, 1,3,4-oxadiazolyl, 1,2,5-oxadiazolyl, etc.], oxazolyl, isoxazolyl, purinyl, thiazolyl, isothiazolyl, thienopyridinyl, thienyl, thiadiazolyl [e.g., 1,2,4-thiadiazolyl, 1,3,4-thiadiazolyl, 1,2,5-thiadiazolyl, etc.], pyridinyl, pyridazinyl, pyrimidinyl, pyrazinyl, pyrazolyl, pyrrolyl, pyrido[2,3-d]pyrimidinyl, pyrrolo[2,3-b]pyridinyl, quinazolinyl, quinolinyl, thieno[2,3-c]pyridinyl, tetrazolyl, triazinyl, and the like. The heteroaryl groups of the present invention can be optionally substituted with one, two, three, four, or five substituents independently selected from the groups as defined herein.

Examples of preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl.

The term "heteroaralkyl" or "heteroarylalkyl," as used herein, alone or in combination, refers to a heteroaryl group attached to the parent molecular moiety through an alkyl group.

The term "heteroaralkylsulfinyl" or "heteroarylalkylsulfinyl," as used herein, alone or in combination, refers to a heteroarylalkyl group attached to the parent molecular moiety through a sulfinyl group (—S[O]—).

The term "heteroaralkenyl" or "heteroarylalkenyl," as used herein, alone or in combination, refers to a heteroaryl group attached to the parent molecular moiety through an alkenyl group.

The term "heteroaralkenylsulfinyl" or "heteroarylalkenylsulfinyl," as used herein, alone or in combination, refers to a heteroarylalkenyl group attached to the parent molecular moiety through a sulfinyl group (—S[O]—).

The term "heteroaralkoxy" or "heteroarylalkoxy," as used herein, alone or in combination, refers to a heteroaryl group attached to the parent molecular moiety through an alkoxy group.

The term "heteroaralkylidene" or "heteroarylalkylidene," as used herein, alone or in combination, refers to a heteroaryl group attached to the parent molecular moiety through an alkylidene group.

The term "heteroaryloxy," as used herein, alone or in combination, refers to a heteroaryl group attached to the parent molecular moiety through an oxygen atom.

The term "heteroarylsulfinyl," as used herein, alone or in combination, refers to an aromatic five- or six-membered ring, where at least one atom is selected from the group consisting of N, O, and S, and the remaining ring atoms are carbon, that is attached to the parent molecular moiety through a sulfinyl group (—S[O]—). Heteroarylsulfinyl groups are exemplified by benzothienylsulfinyl, benzoxazolylsulfinyl, benzofuranylsulfinyl, benzimidazolylsulfinyl, benzthiazolyl sulfonyl, benzotriazolylsulfinyl, cinnolinyl-sulfinyl, furylsulfinyl, imidazolylsulfinyl, triazolylsulfinyl [e.g., 4H-1,2,4-triazolyl, 1H-1,2,3-triazolyl, 2H-1,2,3-triazolyl, etc.], tetrazolylsulfinyl [e.g. 1H-tetrazolyl, 2H-tetrazolyl, etc.], indazolylsulfinyl, indolylsulfinyl, isoxazolylsulfinyl, isoquinolinylsulfinyl, isothiazolylsulfinyl, naphthyridinylsulfinyl, oxadiazolylsulfinyl [e.g., 1,2,4-oxadiazolyl, 1,3,4-oxadiazolyl, 1,2,5-oxadiazolyl, etc.], oxazolylsulfinyl, isoxazolylsulfinyl, purinylsulfinyl, thiazolylsulfinyl, isothiazolylsulfinyl, thienopyridinylsulfinyl, thienylsulfinyl, thiadiazolylsulfinyl [e.g., 1,2,4-thiadiazolyl, 1,3,4-thiadiazolyl, 1,2,5-thiadiazolyl, etc.], pyridinylsulfinyl, pyridazinylsulfinyl, pyrimidinylsulfinyl, pyrazinylsulfinyl, pyrazolylsulfinyl, pyrrolylsulfinyl, pyrido[2,3-d]pyrimidinylsulfinyl, pyrrolo[2,3-b]pyridinylsulfinyl, quinazolinylsulfinyl, quinolinylsulfinyl, thieno[2,3-c]pyridinylsulfinyl, tetrazolylsulfinyl, triazinylsulfinyl, and the like. The heteroarylsulfinyl groups of the present invention can be optionally substituted with one, two, three, four, or five substituents independently selected from the groups as defined herein.

Examples of preferred heteroarylsulfinyl groups include, without limitation, thienylsulfinyl, benzothienylsulfinyl, furylsulfinyl, benzofurylsulfinyl, dibenzofurylsulfinyl, pyrrolylsulfinyl, imidazolylsulfinyl, pyrazolylsulfinyl, pyridylsulfinyl, pyrazinylsulfinyl, pyrimidinylsulfinyl, indolylsulfinyl, quinolylsulfinyl, isoquinolylsulfinyl, quinoxalinylsulfinyl, tetrazolylsulfinyl, oxazolylsulfinyl, thiazolylsulfinyl, triazolylsulfinyl, and isoxazolylsulfinyl.

The term "heteroarylsulfonyl," as used herein, alone or in combination, refers to a heteroaryl group attached to the parent molecular moiety through a sulfonyl group.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The terms "heterocycloalkylsulfinyl" and, interchangeably, "heterocyclic sulfinyl," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring, which is attached to the parent molecular moiety through a sulfinyl group (—S [O]—). Heterocycloalkylsulfinyl groups of the invention are exemplified by azetidinylsulfinyl, 1,3-benzodioxolylsulfinyl, dihydroisoindolylsulfinyl, dihydroisoquinolinylsulfinyl, dihydrocinnolinylsulfinyl, dihydrobenzodioxinylsulfinyl, dihydro[1,3]oxazolo[4,5-b]pyridinylsulfinyl, benzothiazolylsulfinyl, dihydroindolylsulfinyl, dihy-dropyridinylsulfinyl, 1,3-dioxanylsulfinyl, 1,4-dioxanylsulfinyl, 1,3-dioxolanylsulfinyl, isoindolinylsulfinyl, morpholinylsulfinyl, piperazinylsulfinyl, pyrrolidinylsulfinyl, tetrahydropyridinylsulfinyl, piperidinylsulfinyl, thiomorpholinylsulfinyl, and the like. The heterocycle groups may be optionally substituted unless specifically prohibited.

The term "heterocycloalkenyl," as used herein, alone or in combination, refers to a heterocycle group attached to the parent molecular moiety through an alkenyl group.

The term "heterocycloalkoxy," as used herein, alone or in combination, refers to a heterocycle group attached to the parent molecular group through an oxygen atom.

The term "heterocycloalkyl," as used herein, alone or in combination, refers to an alkyl radical as defined above in which at least one hydrogen atom is replaced by a heterocyclo radical as defined above, such as pyrrolidinylmethyl, tetrahydrothienylmethyl, pyridylmethyl and the like.

The term "heterocycloalkylidene," as used herein, alone or in combination, refers to a heterocycle group attached to the parent molecular moiety through an alkylidene group.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl" as used herein, alone or in combination, refers to a linear or branched alkyl group having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptoalkyl" as used herein, alone or in combination, refers to an R'SR— group, where R and R' are as defined herein.

The term "mercaptomercaptyl" as used herein, alone or in combination, refers to a RSR'S— group, where R is as defined herein.

The term "mercaptyl" as used herein, alone or in combination, refers to an RS— group, where R is as defined herein.

The term "null" refers to a lone electron pair.

The term "nitro," as used herein, alone or in combination, refers to —NO$_2$.

The term "optionally substituted" means the anteceding group may be substituted or unsubstituted. When substituted, the substituents of an "optionally substituted" group may include, without limitation, one or more substituents independently selected from the following groups or designated subsets thereof, alone or in combination: hydrogen, carbonyl, thiocarbonyl, carboxyl, lower alkyl carboxylate, lower alkyl carbonate, lower alkyl carbamate, halogen, hydroxy, amino, amido, cyano, hydrazinyl, hydrazinylcarbonyl, alkylhydrazinyl, dialkylhydrazinyl, arylhydrazinyl, heteroarylhydrazinyl, nitro, oxo, thiol, sulfonic acid, trisubstituted silyl, urea, acyl, lower aryloxy, lower acylamino, lower arylthio, lower alkyl, lower alkylamino, lower dialkylamino, lower alkoxy, lower alkoxyalkyl, lower alkylthio, lower alkylsulfinyl, lower alkylsulfonyl, lower alkenyl, lower alkenylamino, lower dialkenylamino, lower alkenyloxy, lower alkenylthio, lower alkenyl sulfonyl, lower alkenylsulfinyl, lower alkynyl, lower alkynylamino, lower dialkynylamino, lower alkynyloxy, lower alkynylthio, lower alkynylsulfonyl, lower alkynylsulfinyl, lower cycloalkyl, lower cycloalkyloxy, lower cycloalkylamino, lower cycloalkylthio, lower cycloalkylsulfonyl, lower cycloalkylsulfinyl, lower cycloalkylalkyl, lower cycloalkylalkyloxy, lower cycloalkylalkylamino, lower cycloalkylalkylthio, lower cycloalkylalkylsulfonyl, lower cycloalkylalkylsulfinyl, aryl, aryloxy, arylamino, arylthio, arylsulfonyl, arylsulfinyl, arylalkyl, arylalkyloxy, arylalkylamino, arylalkylthio, arylalkylsulfonyl, arylalkylsulfinyl, heteroaryl, heteroaryloxy, heteroarylamino, heteroarylthio, heteroarylsulfonyl, heteroarylsulfinyl, heteroarylalkyl, heteroarylalkyloxy, heteroarylalkylamino, heteroarylalkylthio, heteroarylalkylsulfonyl, heteroarylalkylsulfinyl, heterocycloalkyl, heterocycloalkyloxy, heterocycloalkylamino, heterocycloalkylthio, heterocycloalkylsulfonyl, heterocycloalkylsulfinyl, lower haloalkyl, lower haloalkenyl, lower haloalkynyl, lower perhaloalkyl, lower perhaloalkoxy and lower haloalkoxy. Two substituents may be joined together to form a fused four-, five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere inbetween fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. All pendant aryl, heteroaryl, and heterocyclo moieties can be further optionally substituted with one, two, three, four, or five substituents independently selected from the groups listed above.

The terms "oxy" or "oxa," as used herein, alone or in combination, refer to —O—.

The term "oxo" as used herein, alone or in combination, refers to a doubly bonded oxygen =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphonate" as used herein, alone or in combination, refers to the —P(=O)(OR)(OR1) group.

The term "phosphinate" as ues herein, alone or in combination, refers to the —P(=O)(R)(OR1) group.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S and —S—.

The term "sulfinyl," as used herein, alone or in combination, refers to —S(O)—.

The term "sulfonyl," as used herein, alone or in combination, refers to —SO$_2$—.

The term "N-sulfonamido" refers to a RS(=O)$_2$NH— group with R as defined herein.

The term "S-sulfonamido" refers to a —S(=O)$_2$NR$_2$, group, with R as defined herein.

The terms "thia" and "thio," as used herein, alone or in combination, refer to a —S— group or an thioether (R—S—R') wherein the oxygen atom is replaced with sulfur. The oxidized derivatives of the thio group, namely sulfinyl (—SO—) and sulfonyl (—SO$_2$—), are included in the definition of thia and thio.

The term "thioether," as used herein, alone or in combination, refers to a thio group bridging two moieties linked at carbon atoms.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NH— group, with R as defined herein.

The term "O-thiocarbamyl" refers to a —OC(S)NR, group with R as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

The term "urea," as used herein, alone or in combination, refers to —N(R)C(=O)N(R)(R), with R as defined herein.

In any embodiment of the compounds of formula (I), $R_1$ through $R_5$ may be the same, may be different, or some members of $R_1$ through $R_5$ may be the same while the others are different. Any combination is possible.

Examples of compounds of the present invention may include, but are not limited to the following compounds listed in Table 1 below:

TABLE 1

Alkylsulfinyl thiazolides with physical properties.

| No. | Structure | ChemName | Mol. Formula | Mol. Wt. | m.p. (° C.) |
|---|---|---|---|---|---|
| 1 | 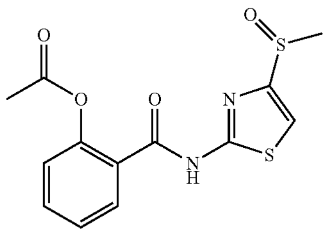 [SMILES: CC(=O)Oc1ccccc1C(=O)Nc1nc(S(C)=O)cs1] | 2-(4-(methylsulfinyl)thiazol-2-ylcarbamoyl)phenyl acetate | C13H12N2O4S2 | 324.38 | 167.3-169.3 |
| 2 | 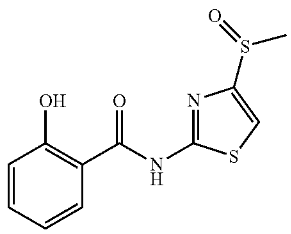 [SMILES: CS(=O)c1csc(NC(=O)c2ccccc2O)n1] | 2-hydroxy-N-(4-(methylsulfinyl)thiazol-2-yl)benzamide | C11H10N2O3S2 | 282.34 | 240 turning dark, then melts at 260-261 |
| 3 | 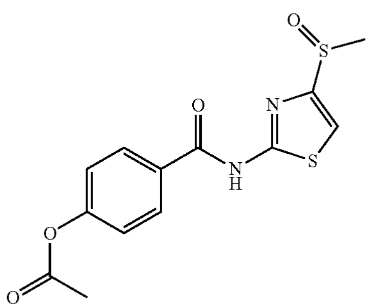 [SMILES: CC(=O)Oc1ccc(C(=O)Nc2nc(S(C)=O)cs2)cc1] | 4-(4-(methylsulfinyl)thiazol-2-ylcarbamoyl)phenyl acetate | C13H12N2O4S2 | 324.38 | |
| 4 | 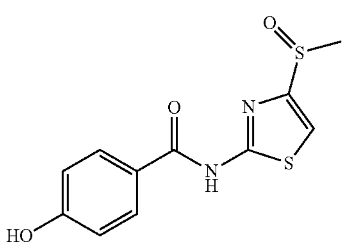 [SMILES: CS(=O)c1csc(NC(=O)c2ccc(O)cc2)n1] | 4-hydroxy-N-(4-(methylsulfinyl)thiazol-2-yl)benzamide | C11H10N2O3S2 | 282.34 | |
| 5 | 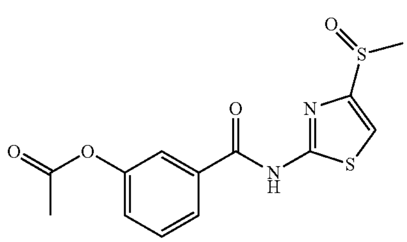 [SMILES: CC(=O)Oc1cccc(C(=O)Nc2nc(S(C)=O)cs2)c1] | 3-(4-(methylsulfinyl)thiazol-2-ylcarbamoyl)phenyl acetate | C13H12N2O4S2 | 324.38 | |
| 6 | 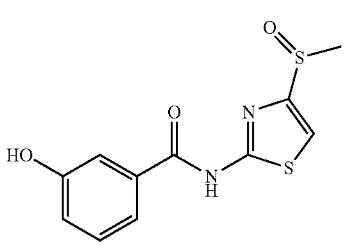 [SMILES: CS(=O)c1csc(NC(=O)c2cccc(O)c2)n1] | 3-hydroxy-N-(4-(methylsulfinyl)thiazol-2-yl)benzamide | C11H10N2O3S2 | 282.34 | |

TABLE 1-continued

Alkylsulfinyl thiazolides with physical properties.

| No. | Structure | ChemName | Mol. Formula | Mol. Wt. | m.p. (° C.) |
|---|---|---|---|---|---|
| 7 | 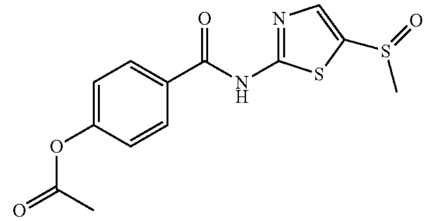 [SMILES: CC(=O)Oc1ccc(C(=O)Nc2ncc(S(C)=O)s2)cc1] | 4-(5-(methylsulfinyl)thiazol-2-ylcarbamoyl)phenyl acetate | C13H12N2O4S2 | 324.38 | |
| 8 | 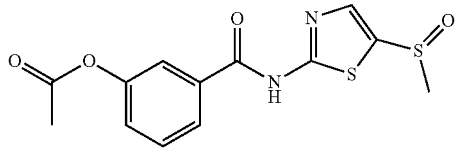 [SMILES: CC(=O)Oc1cccc(C(=O)Nc2ncc(S(C)=O)s2)c1] | 3-(5-(methylsulfinyl)thiazol-2-ylcarbamoyl)phenyl acetate | C13H12N2O4S2 | 324.38 | |
| 9 | 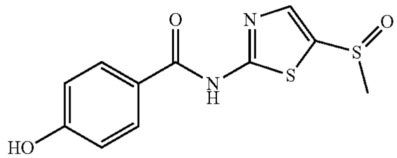 [SMILES: CS(=O)c1cnc(NC(=O)c2ccc(O)cc2)s1] | 4-hydroxy-N-(5-(methylsulfinyl)thiazol-2-yl)benzamide | C11H10N2O3S2 | 282.34 | |
| 10 | 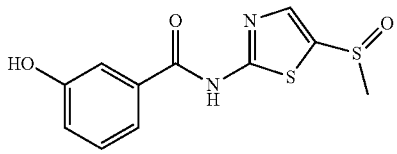 [SMILES: CS(=O)c1cnc(NC(=O)c2cccc(O)c2)s1] | 3-hydroxy-N-(5-(methylsulfinyl)thiazol-2-yl)benzamide | C11H10N2O3S2 | 282.34 | |
| 11 | 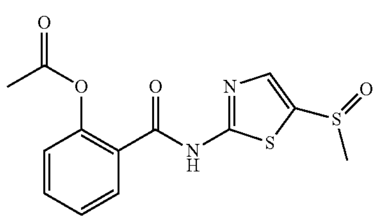 [SMILES: CC(=O)Oc1ccccc1C(=O)Nc1ncc(S(C)=O)s1] | 2-(5-(methylsulfinyl)thiazol-2-ylcarbamoyl)phenyl acetate | C13H12N2O4S2 | 324.38 | |
| 12 | 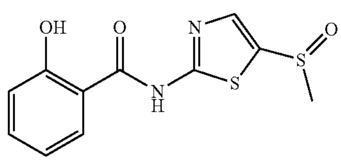 [SMILES: CS(=O)c1cnc(NC(=O)c2ccccc2O)s1] | 2-hydroxy-N-(5-(methylsulfinyl)thiazol-2-yl)benzamide | C11H10N2O3S2 | 282.34 | |

For the above compounds that have a methylsulfinyl (—S[=O]CH$_3$), it is also envisioned by the inventors that in place of the methylsulfinyl, a moiety selected from —S[=O]CH$_2$CH$_3$, —S[=O]CH(CH$_3$)$_2$, —CH$_2$—S[=O]CH$_3$, —CH$_2$—S[=O]C(CH$_3$)$_3$—, —S[=O]cyclopropyl, and —S[=O]CH$_2$Ph may be used.

A compound of the present invention, where R$_1$ through R$_7$ are defined above, may be made by reacting an acyl halide with an aminothiazole under suitable reaction conditions. In some embodiments, the reaction may be generically represented as follows:

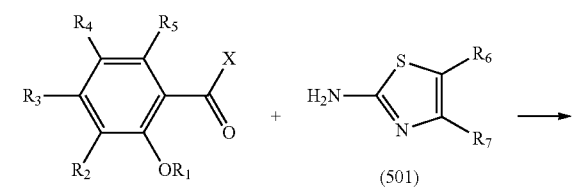

(500, X = OH, OMe, F, Cl, Br)

Compound of Formula (I)

The term carrier is used in its broadest sense. For example, the term carrier refers to any carriers, diluents, excipients, wetting agents, buffering agents, suspending agents, lubricating agents, adjuvants, vehicles, delivery systems, emulsifiers, disintegrants, absorbents, preservatives, surfactants, colorants, flavorants, and sweeteners. In some embodiments, the carrier may be a pharmaceutically acceptable carrier, a term narrower than carrier, because the term pharmaceutically acceptable carrier" means a non-toxic that would be suitable for use in a pharmaceutical composition.

The present invention also relates to a pharmaceutical composition comprising, in a pharmaceutically acceptable carrier, an effective amount of at least one compound of the invention.

The term effective amount is used in its broadest sense. The term, for example, refers to the amount required to produce a desired effect.

In some embodiments, the compound of the invention is present in a pharmaceutical composition in an effective amount for treating HCV infection (e.g., chronic HCV infection). "Treating HCV infection" may refers to: (i) preventing HCV infection from occurring in an animal that may be predisposed to HCV infection but has not yet been diagnosed as having it; (ii) inhibiting or slowing HCV infection, e.g. arresting its development; (iii) relieving chronic infection, e.g. causing its regression; (iv) improving a symptom in a subject having chronic infection; and/or (v) prolonging the survival of a subject having chronic infection.

The compositions of the present invention may be formulated as solid or liquid dosage forms, or as pastes or ointments, and may optionally contain further active ingredients.

A pharmaceutical composition of the present invention comprises a pharmaceutically acceptable carrier, which is not particularly limited, and includes a wide range of carriers known to those of ordinary skill in the art, and including wetting or dispersing agents (U.S. Pat. No. 5,578,621, which is incorporated herein by reference), starch derivatives (U.S. Pat. No. 5,578,621, which is incorporated herein by reference), excipients, and the like. Tablet embodiments may optionally comprise a coating of a substance that constitutes an enteric coating, i.e., a coating that substantially insoluble in gastric secretion but substantially soluble in intestinal fluids.

Pharmaceutical compositions comprising the compounds of the present invention are in some embodiments formulated for oral administration and are optionally in the form of a liquid, for example an emulsion or a solution or a suspension in water or oil such as arachis oil, or other liquid. Formulations of non-aqueous micellar solutions may be prepared according to the method disclosed in U.S. Pat. No. 5,169,846, which is incorporated herein by reference. Alternatively, tablets can be manufactured, for example, by performing the following steps: wet granulation; drying; and compression. Film coating may generally be performed with organic solvents.

The present invention is a method, comprising administering to a subject at least one compound of the present invention in an amount in an effective amount for treating HCV infection (e.g., chronic HCV infection). In some embodiments, the method, comprising administering to a subject at least one pharmaceutical composition which comprises at least one compound of the present invention in an amount in an effective amount for treating HCV infection (e.g., chronic HCV infection).

The present invention is a method, comprising administering to a subject at least one compound of the present invention in an amount in an effective amount for treating HBV infection (e.g., chronic HBV infection). In some embodiments, the method, comprising administering to a subject at least one pharmaceutical composition which comprises at least one compound of the present invention in an amount in an effective amount for treating HBV infection (e.g., chronic HBV infection).

In some embodiments, the subject is selected from animals. In some embodiments, the subject is selected from mammals. In some embodiments, the subject is selected from pets, such as mice, dogs, cats, etc. In some embodiments, the subject is selected from humans.

In some embodiments, the invention provides a method of treating a viral infection in a subject, comprising administering to the subject at least one dose of an effective amount of at least one compound of the present invention. In some embodiments, the invention provides a method of treating a viral infection in a subject, comprising administering to the subject at least one dose of an effective amount of at least one pharmaceutical composition comprising, in a pharmaceutically acceptable carrier, at least one compound of the present invention.

In some embodiments the antiviral treatment or prophylactic dosages of the compound of the present invention may depend upon the weight of the subject, and may be inferred by one of ordinary skill without undue experimentation by reference to the following examples, which are set forth for purposes of illustration and are not intended to be limiting.

The inventive compounds and compositions may be administered locally or systemically by any means known to an ordinarily skilled artisan. For example, the inventive compounds and compositions may be administered orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intraarterial, intramuscular, intraperitoneal, intrathecal, intraventricular, intrasternal, intracranial or intraosseous injection and infusion techniques. The exact administration protocol will vary depending upon various factors including the age, body weight, general health, sex and diet of the patient; the determination of specific administration procedures would be routine to an ordinarily skilled artisan.

Dose levels on the order of about 0.1 to about 100 mg/kg of the active ingredient compound are useful in the treatment of the above conditions (e.g., 0.1 mg/kg-day). In some embodiments, the amounts range from about 1 to about 10 mg/kg, and in other embodiments, the amounts range from about 2 to about 5 mg/kg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Any administration regimen for regulating the timing and sequence of drug delivery can be used and repeated as necessary to effect treatment. Such regimen may include multiple uses or preadministration and/or co-administration and/or postadministration with food, liquid, or water.

The present invention also relates to a kit, comprising, in a compartment, at least one pharmaceutical composition comprising, in a pharmaceutically acceptable carrier, an effective amount of at least one compound of the invention. In some embodiments, the kit further comprises written instructions for administering the pharmaceutical composition. In some embodiments, written instructions for administering concern indications noted elsewhere in this disclosure. In some embodiments, written instructions for administering concern an administration regimen noted elsewhere in this disclosure.

The kit could take any form. By way of example, a kit includes one or more containers for storing a pharmaceutical composition. In some embodiments, a container contains written instructions for administering the pharmaceutical composition. In some embodiments, a container contains is the substrate for the written instructions for administering the pharmaceutical composition. In some embodiments, the written instructions for administering the pharmaceutical composition are affixed to a container, for example, as in a container for filling a prescription sometimes has written instructions affixed on a surface.

In some embodiments, the compound of the present invention may exhibit selective antiviral activity. The term "selective antiviral" as used herein means that, at dosages effective for the prevention or treatment of a viral disease, the activity is more antiviral than antibacterial, antifungal, or antiparasite, and gut flora of the subject is not disrupted to levels expected with broad spectrum antibiotics. For example, the effective dosage for antiviral treatment (e.g., reducing viral load at least about 2 times) may not reduce bacterial, fungal, or parasite levels in the gut (e.g., more than about 2 times).

Other embodiments of the invention will be apparent to those skilled in the art from consideration of the specification and practice of the invention disclosed herein. It is intended that the specification and its examples be considered as exemplary only, with a true scope and spirit of the invention being indicated by what may eventually be claimed.

EXPERIMENTAL PROCEDURES

1. Materials and Methods
1.1 Materials.

All test compounds were provided by Romark Laboratories. Nitazoxanide and Tizoxanide were used as standards. All compounds were dissolved in dimethylsulfoxide (DMSO) stock solution and then diluted using standard serial dilution methods.

1.2. HBV Studies.
1.2.1. Antiviral Assays.

HBV antiviral assays were conducted as previously described [Korba, B. E. et al. Antiviral Res. 77, 56-63 (2008);]. Briefly, confluent cultures of 2.2.15 cells were maintained on 96-well flat-bottomed tissue culture plates (confluence in this culture system is required for active, high levels of HBV replication equivalent to that observed in chronically-infected individuals. Cultures were treated with nine consecutive daily doses of the test compounds. HBV DNA levels were assessed by quantitative blot hybridization 24 hr. after the last treatment. Cytotoxicity was assessed by uptake of neutral red dye 24 hr. following the last treatment.

1.2.3. Production of HBV Proteins.

Cultures of 2.2.15 cells were treated under standard procedures and semi-quantitative EIA-based analysis of HBV proteins was performed as previously described [Korba, B. E. et al. Antiviral Res. 77, 56-63 (2008)]. HBeAg was analyzed ETI-EBK Plus® (DiaSorin, Inc., Stillwater, Minn. USA). Samples were diluted (2 to 10-fold) to bring levels into the dynamic response ranges of the EIA's. HBsAg, and HBeAg were analyzed from culture medium samples and HBcAg was analyzed from intracellular lysates. Intracellular HBV RNA was assessed by quantitative northern blot hybridization.

1.3. HCV Studies.
1.3.1. Replicon Genotype 1b and 1a Cell Assays.

Antiviral activity of test compounds was assessed in a 3-day assay using the stably-expressing HCV replicon cell line, AVA5 (sub-genomic CON1, genotype 1b) [Korba, B. E. et al. Antiviral Res. 77, 56-63 (2008); Blight et al., Science 290, 1972-1974 (2000)] maintained as sub-confluent cultures on 96-well plates as previously described [Okuse et al., Antiviral Research 65, 23-34 (2005)]. Antiviral activity was determined by blot hybridization analysis of intracellular HCV RNA (normalized to the level of cellular B-actin RNA in each culture sample) and cytotoxicity was assessed by neutral red dye uptake after 3 days of treatment. Additional studies were performed using Huh7 cells containing another HCV replicon, H/FL-Neo, a genotype 1a full length construct [Blight et al., J. Virol. 77, 3181-3190 (2003)]. For studies involving human serum, standard culture medium (which contains 10% fetal bovine serum) and assay conditions were maintained.

1.3.2. Infectious Genotype 2a Cell Culture Assay.

Genotype 2a antiviral assays were conducted as previously described [Lindenbach, B. D.; Rice, C. M. et al. Science, 309, 623-626 (2005)]. In vitro, the Huh7.5/JFH-1 HCV continuous cell culture system was used to study the effects of serial concentrations of NTZ and alkylsulfinyl thiazolide analogs of the present invention on HCV replication. Cell viability was determined using the Calcein assay kit (Biotium, Inc. Hayward, Calif., USA). The alternate method for measuring cell cytotoxicity was via the Guava Technologies ViaCount assay (Millipore) The ViaCount Assay provides rapid and reliable determinations of viability and total cell count. It distinguishes viable and non-viable cells based on differential permeabilities of two DNA-binding dyes in the Guava ViaCount® Reagent. The nuclear dye stains only nucleated cells, while the viability dye brightly stains dying cells. This combination of dyes enables the Guava ViaCount Assay to distinguish viable, apoptotic, and dead cells. Debris is excluded from results based on negative staining with the nuclear dye.

HCV replication levels were determined by RT-PCR on RNA from cell culture supernatants. J6-infected Huh 7.5 cells were seeded in 12-well plates at a density of $2.0E^5$ cells/well in 1.5 mL of DMEM supplemented with 10% FBS and 1% Pen/Strep. After overnight incubation, the media was aspirated and replaced with fresh DMEM and NTZ, TIZ, and other thiazolides at concentrations of 1 uM and 10 uM per well to make up a final volume of 1 mL/well. A positive control of IFN-α at concentrations of 10 IU/mL and 50 IU/mL, negative control wells containing mock incubations of DMEM with 1 uL and 10 uL (the same volume of the molecular compounds at 1 uM and 10 uM, respectively) of DMSO was included to rule out nonspecific effects of DMSO on the cells, and J6-infected with only DMEM were used as negative controls. A final control group consisted of un-infected Huh 7.5 cells, plated at the same time and density as the J6-infected cells on a separate plate. 48 hours and 120 hours after incubation with thiazolides, the media was collected and frozen, cells were washed 2× with PBS, and lysed in 500 uL of lysis buffer per well. Following lysis, RNA was extracted from the cells using the RNAqueous-4PCR Kit from Ambion, and the RNA concentration determined using the NanoDrop® machine. Reverse-transcription reactions produced 1.5 µg of cDNA per sample, which was then used for rt-PCR to quantify the HCV viral load in each sample. Analysis of the rt-PCR results generated the fold increases and decreases of the HCV viral load in comparison to untreated J6 cells. The Huh 7.5 controls did not show any HCV virus, as expected.

NTZ and alkylsulfinyl thiazolide analog 2 described herein demonstrated efficacy with regards to HCV replication without being cytotoxic to Huh 7.5 cells.

1.4. Presentation of Results.

$EC_{50}$, $EC_{90}$ and $CC_{50}$ values (±standard deviations [S.D.]) were calculated by linear regression analysis using data combined from all treated cultures (Korba, B. E. et al. Antiviral Res. 77, 56-63 (2008)). $EC_{50}$ and $EC_{90}$ are drug concentrations at which a 2-fold, or a 10-fold depression of intracellular HBV DNA or HCV RNA (relative to the average levels in untreated cultures), respectively, was observed. $CC_{50}$ is the drug concentration at which a 2-fold lower level of neutral red dye uptake (relative to the average levels in untreated cultures) was observed. Selectivity index (S.I.) was calculated as $CC_{50}/EC_{90}$ for HBV assays and $CC_{50}/EC_{50}$ for HCV assays. $EC_{90}$ values were used for calculation of the S.I. in HBV assays since at least a 3-fold depression of HBV DNA levels is typically required to achieve statistical significance in this assay system [Korba, B. E. et al. Antiviral Res. 77, 56-63 (2008)].

1.5 Synthetic Procedures.

Compounds (I) of the present invention, where $R_1$ through $R_7$ are defined above, may be made by reacting an acyl halide, ester or carboxylic acid derivative with an aminothiazole under suitable reaction conditions. In some embodiments, the reaction may be generically represented as follows:

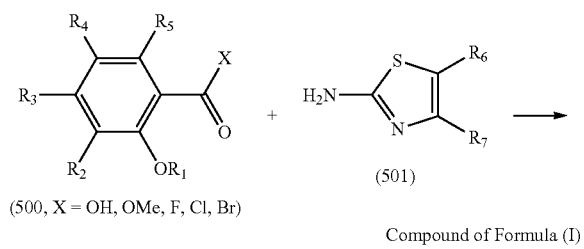

Compound of Formula (I)

In the first synthetic route compound (I) is prepared by reaction of the aroyl derivative (500), wherein X is hydroxy, chloro, fluoro, bromo, alkoxy and the like, with aminothiazole derivative (501), under suitable coupling conditions, preferably in the presence of a suitable solvent to provide (I). When X is hydroxy, standard coupling agents including DCC, EDC/HOBt, EDC/HOAt and related amide bond-forming reagents may be used to prepare (I). When X is chloro, fluoro, bromo, and alkoxy, tertiary amine bases may be added to prepare (I), including triethylamine, diisopropylethylamine, N-methylpiperidine, N-methylmorpholine, DBU, DBN, DABCO, 4-(dimethylamino)pyridine and the like. Alternatively, inorganic bases may be employed including sodium bicarbonate, sodium carbonate, potassium carbonate, cesium carbonate, sodium hydroxide, potassium hydroxide, sodium hydride, potassium hydride and the like. Suitable solvents for all reactions include diethyl ether, tetrahydrofuran, 1,4-dioxane, ethyl acetate, acetonitrile, dichloromethane, dichloroethane, benzene, toluene, pyridine, collidine, lutidine, N,N-dimethylformamide, N,N-dimethylacetamide, N-methyl-2-pyrrolidone, DMSO, water, combinations thereof and the like. Optimal temperature ranges may vary from −25° C. to 250° C. Reactions may optionally be conducted in a microwave reactor at ambient temperature to 250° C.

When $OR_1$ is acetoxy or lower acyloxy, hydrolysis of (I) with dilute hydrochoric acid, optionally in the presence of cosolvents like tetrahydrofuran, 1,4-dioxane or acetonitrile at a temperature, such as about ambient room temperature to about 50° C. yields the free phenolic compound where $OR_1$=OH.

In the second synthetic route, compound (I) is prepared by reaction of the aroyl derivative (I, $R_1$=OH) with QC(=O)$G_1$, wherein $G_1$ is as defined above and Q is $R_8$, $OR_8$, $NHR_8$, OR $NR_8R_9$, as defined herein, under suitable coupling conditions, referably in the presence of a suitable solvent.

Detailed experimental procedures are described below for compounds 1 to 12. By using analogous methods or slight modifications thereof, all remaining compounds of the present invention can be prepared.

Alternatively, compounds of the present invention can be prepared using the following reaction scheme:

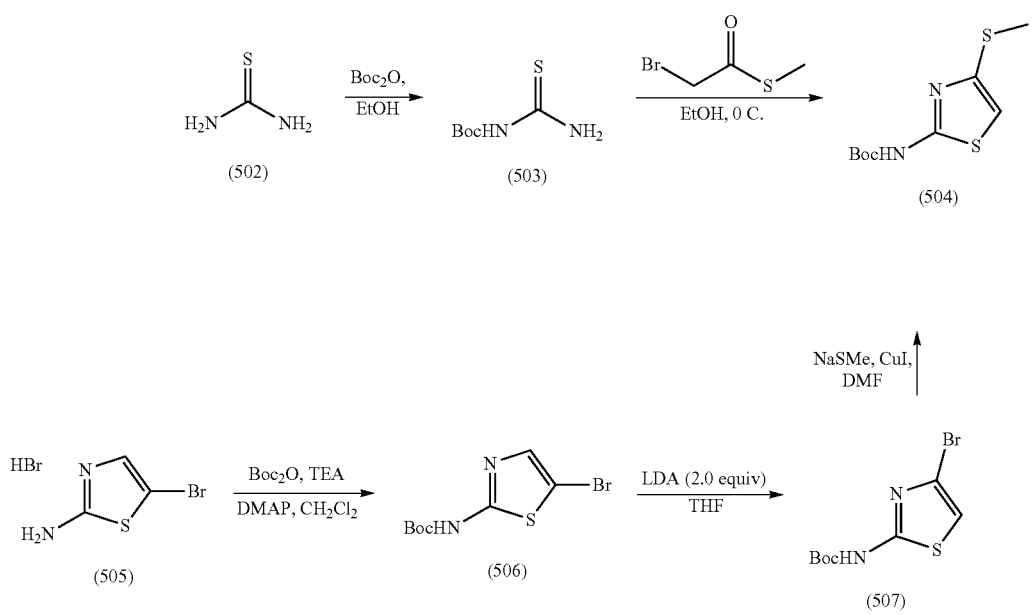

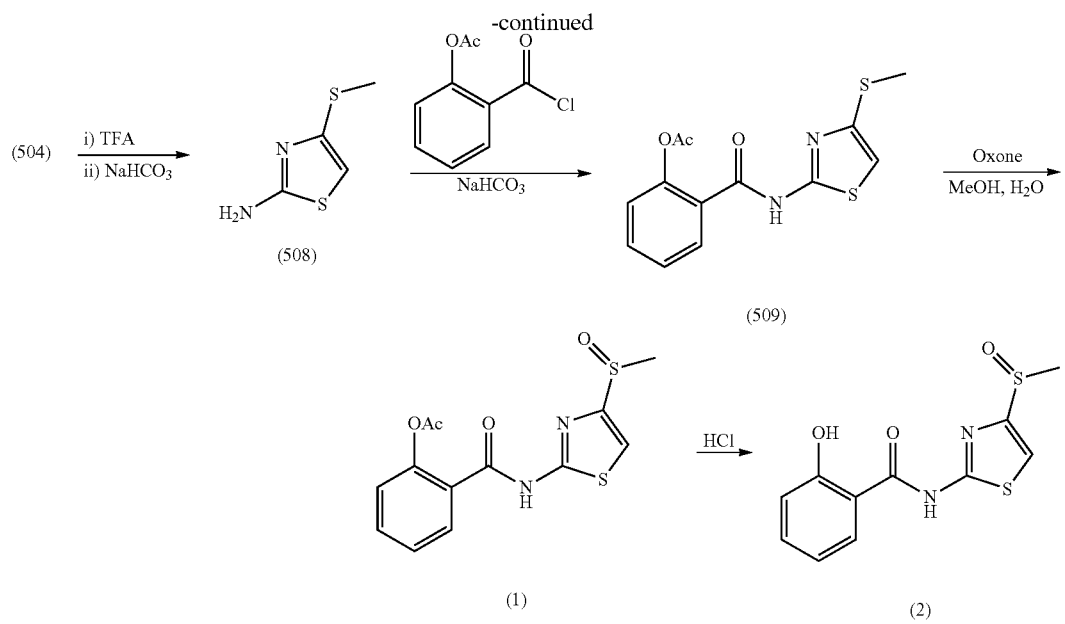

The compounds 2-{[4-(methylsulfinyl)-1,3-thiazol-2-yl]carbamoyl}phenyl acetate (1) and 2-hydroxy-N-[4-(methylsulfinyl)-1,3-thiazol-2-yl]benzamide (2) may be synthesized by the method described in Example 1.5.1.

Other compounds of the present invention may also be made in accordance with the following reaction scheme:

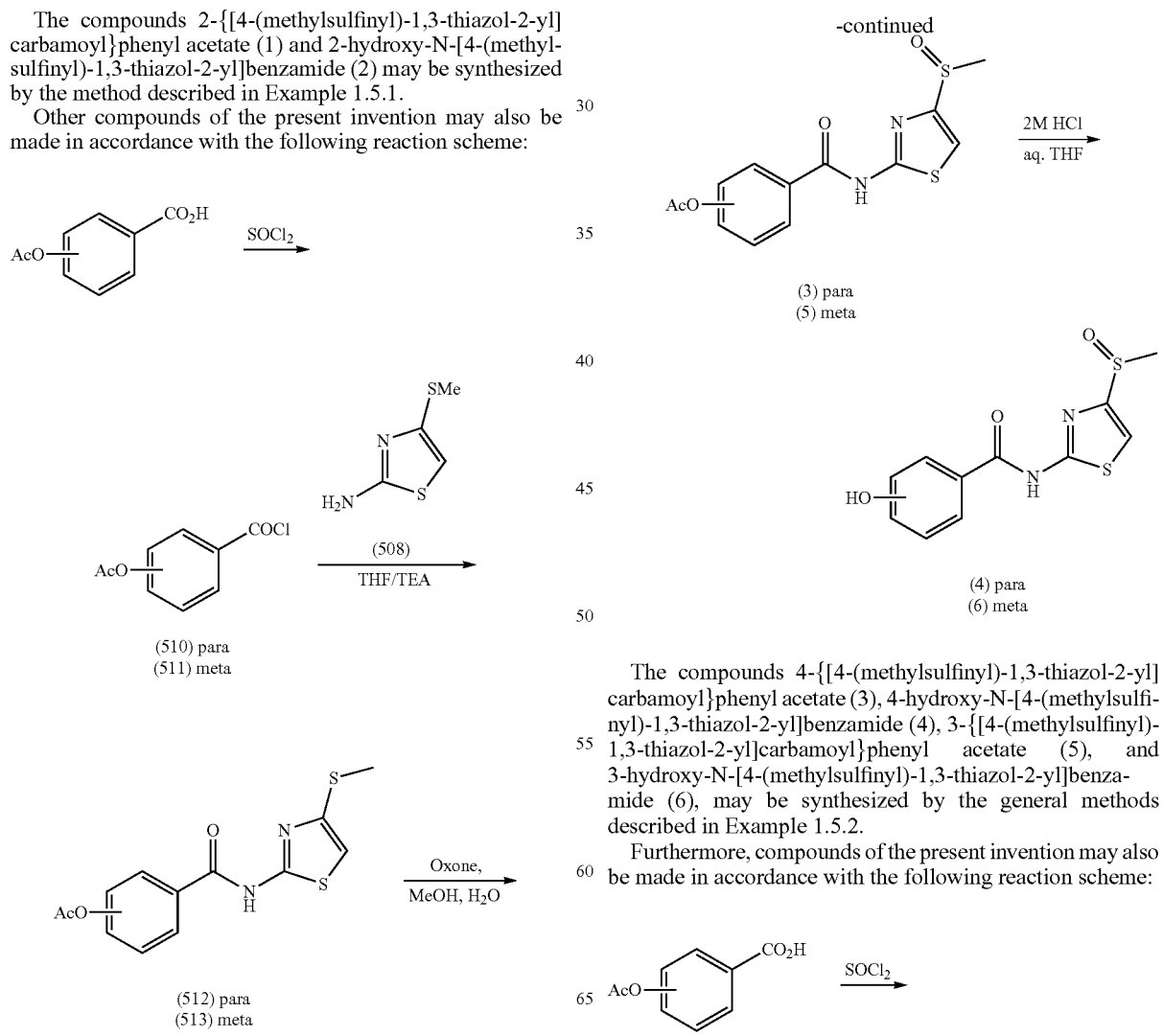

The compounds 4-{[4-(methylsulfinyl)-1,3-thiazol-2-yl]carbamoyl}phenyl acetate (3), 4-hydroxy-N-[4-(methylsulfinyl)-1,3-thiazol-2-yl]benzamide (4), 3-{[4-(methylsulfinyl)-1,3-thiazol-2-yl]carbamoyl}phenyl acetate (5), and 3-hydroxy-N-[4-(methylsulfinyl)-1,3-thiazol-2-yl]benzamide (6), may be synthesized by the general methods described in Example 1.5.2.

Furthermore, compounds of the present invention may also be made in accordance with the following reaction scheme:

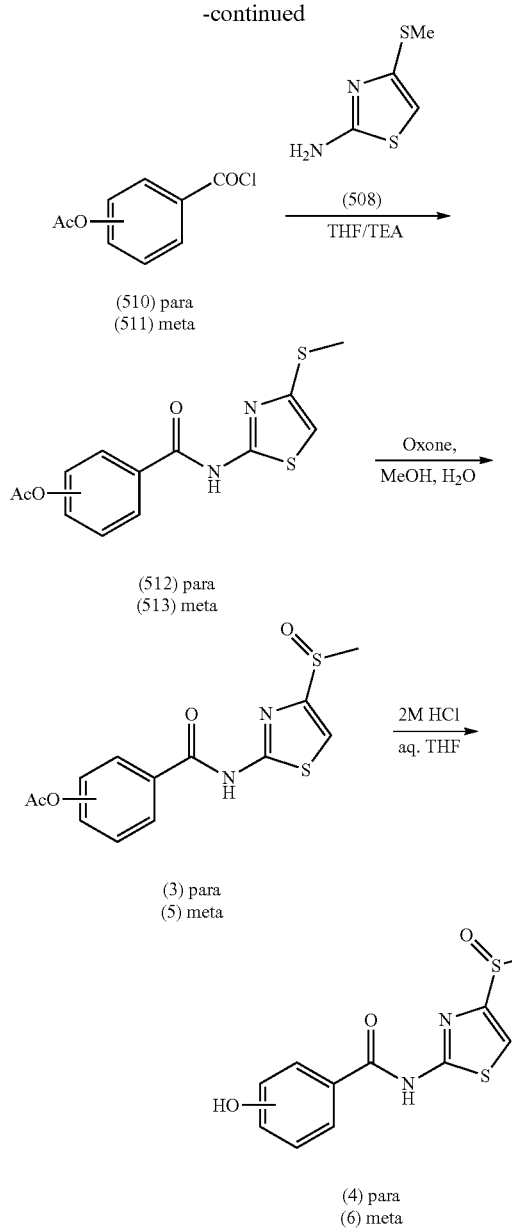

The compounds 4-{[5-(methylsulfinyl)-1,3-thiazol-2-yl]carbamoyl}phenyl acetate (7), 3-{[5-(methylsulfinyl)-1,3-thiazol-2-yl]carbamoyl}phenyl acetate (8), 4-hydroxy-N-[5-(methylsulfinyl)-1,3-thiazol-2-yl]benzamide (9) and 3-hydroxy-N-[5-(methylsulfinyl)-1,3-thiazol-2-yl]benzamide (10) may be synthesized by the general methods described in Example 1.5.3.

Other compounds of the present invention may also be made in accordance with the following reaction scheme:

The compounds 2-(5-(methylsulfinyl)thiazol-2-ylcarbamoyl)phenyl acetate (11) and 2-hydroxy-N-(5-(methylsulfinyl)thiazol-2-yl)benzamide (12), may be synthesized by the method described in Example 1.5.4.

In addition to the compounds listed in Table 1, further examples of compounds of the present invention may include, but are not limited to the following compounds listed in Table 3. This set of examples is not intended to limit the invention.

TABLE 3

| No. | Structure |
|-----|-----------|
| 13 | 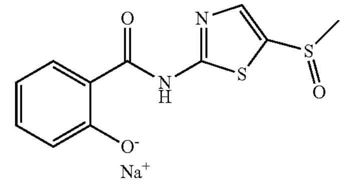 [SMILES: CS(=O)c1cnc(NC(=O)c2ccccc2[O-])s1 ; [Na+]] |
| 14 | 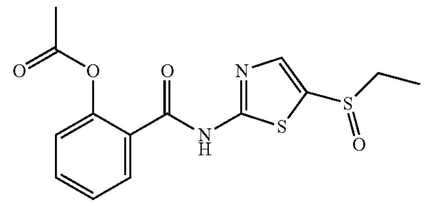 [SMILES: CCS(=O)c1cnc(NC(=O)c2ccccc2OC(C)=O)s1] |
| 15 | 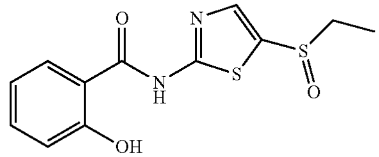 [SMILES: CCS(=O)c1cnc(NC(=O)c2ccccc2O)s1] |
| 16 | 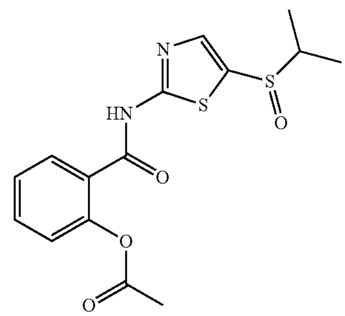 [SMILES: CC(=O)Oc1ccccc1C(=O)Nc1ncc(S(=O)C(C)C)s1] |
| 17 | 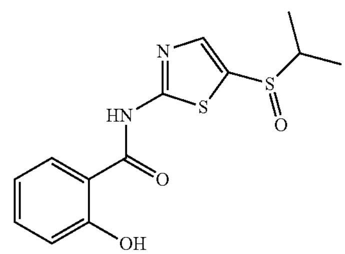 [SMILES: CC(C)S(=O)c1cnc(NC(=O)c2ccccc2O)s1] |
| 18 | 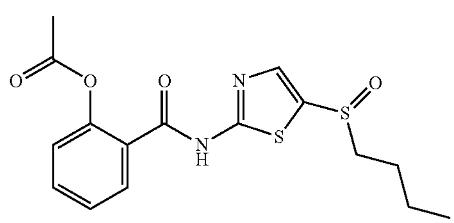 [SMILES: CCCCS(=O)c1cnc(NC(=O)c2ccccc2OC(C)=O)s1] |
| 19 | 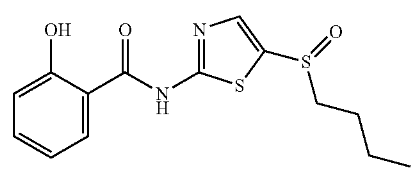 [SMILES: CCCCS(=O)c1cnc(NC(=O)c2ccccc2O)s1] |

TABLE 3-continued
| No. | Structure |
|---|---|
| 20 | 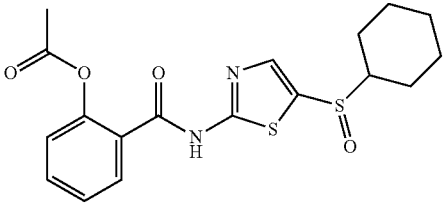 [SMILES: CC(=O)Oc1ccccc1C(=O)Nc1ncc(S(=O)C2CCCCC2)s1] |
| 21 | 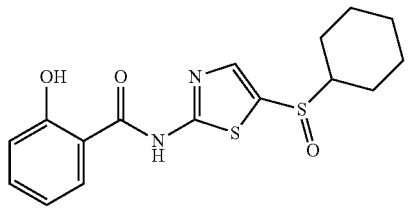 [SMILES: O=C(Nc1ncc(S(=O)C2CCCCC2)s1)c1ccccc1O] |
| 22 | 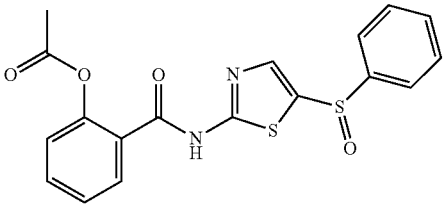 [SMILES: CC(=O)Oc1ccccc1C(=O)Nc1ncc(S(=O)c2ccccc2)s1] |
| 23 | 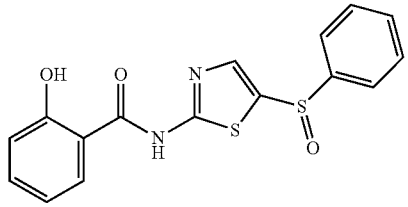 [SMILES: O=C(Nc1ncc(S(=O)c2ccccc2)s1)c1ccccc1O] |
| 24 | 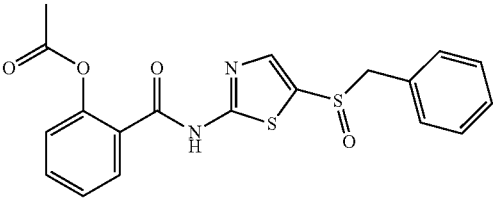 [SMILES: CC(=O)Oc1ccccc1C(=O)Nc1ncc(S(=O)Cc2ccccc2)s1] |
| 25 | 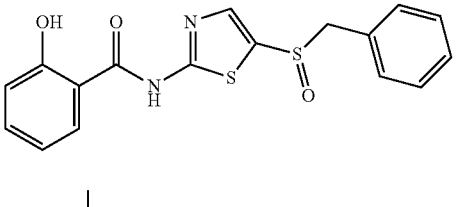 |
| 26 | 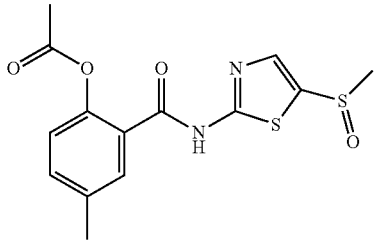 [SMILES: CC(=O)Oc1ccc(C)cc1C(=O)Nc1ncc(S(C)=O)s1] |
| 27 | 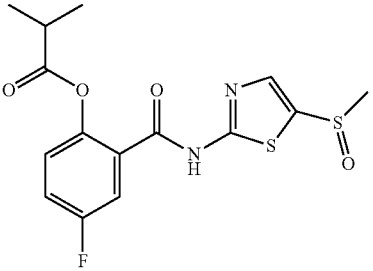 [SMILES: CC(C)C(=O)Oc1ccc(F)cc1C(=O)Nc1ncc(S(C)=O)s1] |
| 28 | 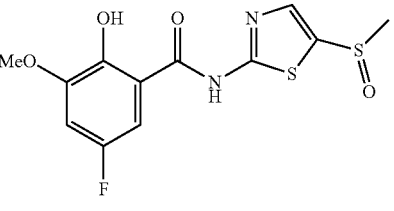 [SMILES: COc1cc(F)cc(C(=O)Nc2ncc(S(C)=O)s2)c1O] |
| 29 | 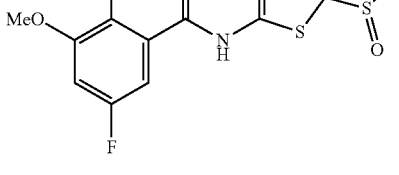 |
| 30 | 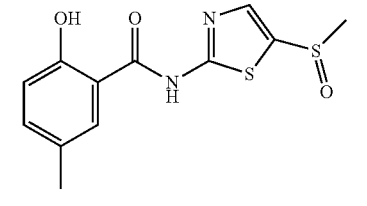 [SMILES: Cc1ccc(O)c(C(=O)Nc2ncc(S(C)=O)s2)c1] |
| 31 | 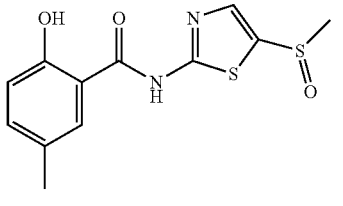 |

TABLE 3-continued

| No. | Structure |
|---|---|
| 32 | (structure) |
| 33 | (structure) |
| 34 | (structure) |
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) |
| 44 | (structure) |

TABLE 3-continued

| No. | Structure |
|---|---|
| 45 | |
| 46 | |
| 47 | |
| 48 | |
| 49 | |
| 50 | |
| 51 | 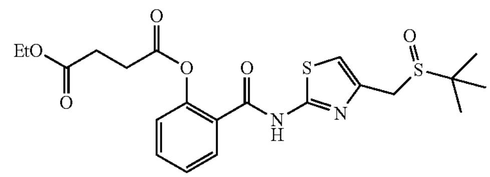 [SMILES: CCOC(=O)CCC(=O)Oc1ccccc1C(=O)Nc1nc(CS(=O)C(C)(C)C)cs1] |
| 52 | 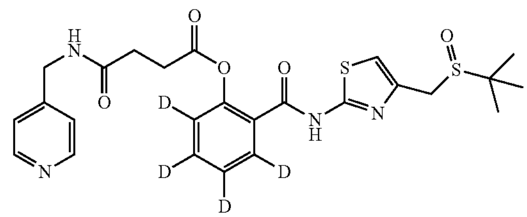 [SMILES: [2H]c1c([2H])c([2H])c(C(=O)Nc2nc(CS(=O)C(C)(C)C)cs2)c(OC(=O)CCC(=O)NCc2ccncc2)c1[2H]] |
| 53 | 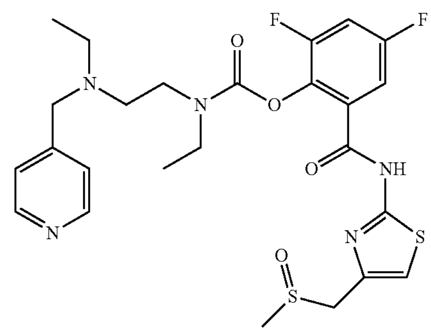 [SMILES: CCN(CCN(CC)C(=O)Oc1c(F)cc(F)cc1C(=O)Nc1nc(CS(C)=O)cs1)Cc1ccncc1] |
| 54 | 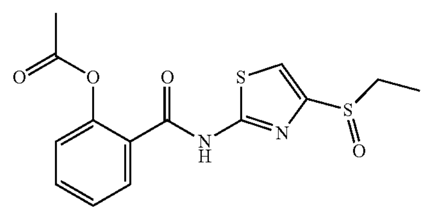 [SMILES: CCS(=O)c1csc(NC(=O)c2ccccc2OC(C)=O)n1] |
| 55 | 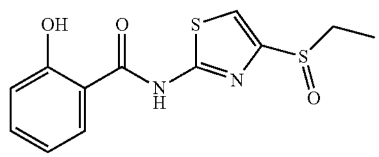 [SMILES: CCS(=O)c1csc(NC(=O)c2ccccc2O)n1] |
| 56 | 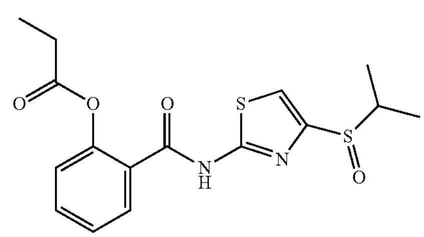 [SMILES: CCC(=O)Oc1ccccc1C(=O)Nc1nc(S(=O)C(C)C)cs1] |
| 57 | 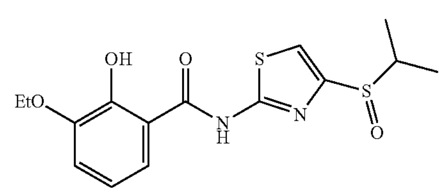 [SMILES: CCOc1cccc(C(=O)Nc2nc(S(=O)C(C)C)cs2)c1O] |

TABLE 3-continued

| No. | Structure |
|---|---|
| 58 | (chemical structure) |
| 59 | (chemical structure) |
| 60 | (chemical structure) |
| 61 | (chemical structure) |
| 62 | (chemical structure) |
| 63 | (chemical structure) |
| 64 | (chemical structure) |
| 65 | (chemical structure) |
| 66 | (chemical structure) |
| 67 | (chemical structure) |
| 68 | (chemical structure) |
| 69 | (chemical structure) |
| 70 | (chemical structure) |

TABLE 3-continued

| No. | Structure |
|---|---|
| 71 | (2-hydroxy-5-methylphenyl)-N-(4-(methylsulfinyl)thiazol-2-yl)benzamide |
| 72 | 2-acetoxy-5-((4-fluorobenzyl)oxy)-N-(4-(methylsulfinyl)thiazol-2-yl)benzamide |
| 73 | 5-((4-fluorobenzyl)oxy)-2-hydroxy-N-(4-(methylsulfinyl)thiazol-2-yl)benzamide |
| 74 | 5-(2-(4-cyano-2-(dimethylcarbamoyl)phenyl)ethyl)-2-hydroxy-N-(4-(methylsulfinyl)thiazol-2-yl)benzamide |
| 75 | 2-acetoxy-N-(5-oxo-5,6-dihydro-4H-thieno[2,3-d]thiazol-2-yl)benzamide |
| 76 | 2-hydroxy-N-(5-oxo-5,6-dihydro-4H-thieno[2,3-d]thiazol-2-yl)benzamide |
| 77 | 2-acetoxy-N-(6-methyl-5-oxo-5,6-dihydro-4H-thieno[2,3-d]thiazol-2-yl)benzamide |
| 78 | N-(6-ethyl-6-methyl-5-oxo-5,6-dihydro-4H-thieno[2,3-d]thiazol-2-yl)-2-hydroxybenzamide |
| 79 | 2-acetoxy-N-(5-oxo-5,6-dihydro-4H-thieno[3,2-d]thiazol-2-yl)benzamide |
| 80 | 2-hydroxy-N-(5-oxo-5,6-dihydro-4H-thieno[3,2-d]thiazol-2-yl)benzamide |
| 81 | 2-acetoxy-N-(5-(3-fluorophenyl)-5-oxo-5,6-dihydro-4H-thieno[2,3-d]thiazol-2-yl)benzamide |

TABLE 3-continued

| No. | Structure |
|-----|-----------|
| 82  | 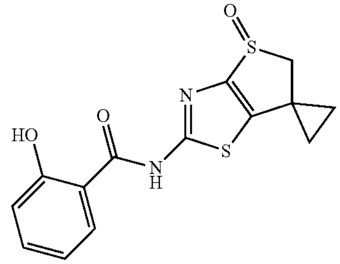 [SMILES: O=C(Nc1nc2c(s1)C1(CC1)CS2=O)c1ccccc1O]          |
| 83  | 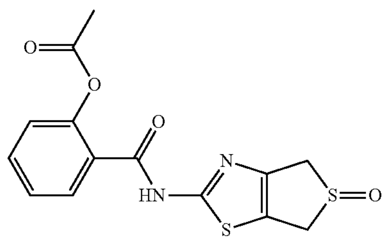 [SMILES: CC(=O)Oc1ccccc1C(=O)Nc1nc2c(s1)CS(=O)C2]          |
| 84  | 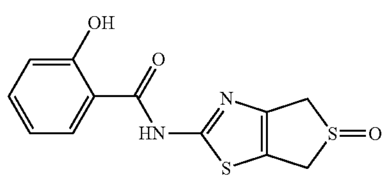 [SMILES: O=C(Nc1nc2c(s1)CS(=O)C2)c1ccccc1O]          |
| 85  | 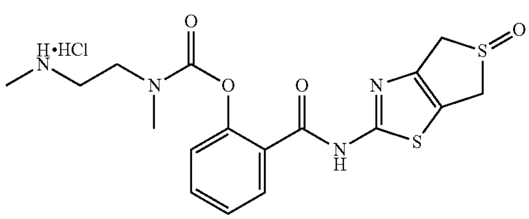 [SMILES: CNCCN(C)C(=O)Oc1ccccc1C(=O)Nc1nc2c(s1)CS(=O)C2 ; Cl]          |
| 86  | 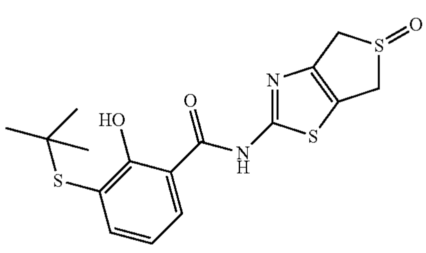 [SMILES: CC(C)(C)Sc1cccc(C(=O)Nc2nc3c(s2)CS(=O)C3)c1O]          |
| 87  | 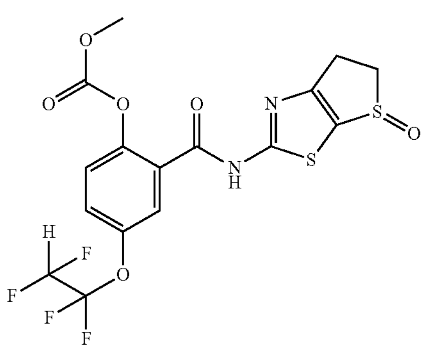 [SMILES: COC(=O)Oc1ccc(OC(F)(F)C(F)F)cc1C(=O)Nc1nc2c(s1)S(=O)CC2]          |
| 88  |           |

General Experimental Details:

$^1$H NMR spectra were recorded on a Bruker Avance Spectrometer at 400 MHz. $^{13}$C NMR spectra were recorded at 100 MHz. Melting points were recorded on a Stanford Research Systems MPA1100 OptiMelt; values are uncorrected.

HPLC data was collected on Agilent 1100 HPLC systems with the following columns and conditions:

A: Agilent Zorbax C8 75×4.6 mm 5 micron column (Part #993967-906) maintained at 30° C. Solvent A Water (0.1% TFA); Solvent B Acetonitrile (0.07% TFA), Gradient 5 min 95% A to 95% B; 2 min hold; then recycle; UV Detection @ 210 and 250 nm.

B: Agilent Zorbax Eclipse XDB-C18 50×4.6 mm 1.8 micron column (Part #927975-902) maintained at 30° C. Solvent A Water (0.1% TFA); Solvent B Acetonitrile (0.07% TFA), Gradient 5 min 95% A to 95% B; 1 min hold; 1 min recycle; 30 sec hold. UV Detection @ 210 and 254 nm with no reference.

C: Agilent Zorbax C8 150×4.6 mm 5 micron column maintained at 30° C. Solvent A Water (0.1% TFA); Solvent B Acetonitrile (0.07% TFA), Gradient 10 min 95% A to 95% B; 2 min hold; then recycle. UV Detection @ 210 and 254 nm with no reference.

Flash chromatography was performed with silica gel from Silacycle (40-63 μm, 60 Å) and Whatman (38-63 μm, 60 Å). LC-MS and mass spectra were recorded on a Waters Alliance HT separations module coupled to a Micromass ZMD mass spectrometer.

1.5.1 Synthesis of 2-hydroxy-N-(4-(methylsulfinyl)thiazol-2-yl)benzamide (2)

The compound, 2-hydroxy-N-[4-(methylsulfinyl)-1,3-thiazol-2-yl]benzamide (2), was prepared according to the following synthetic scheme:

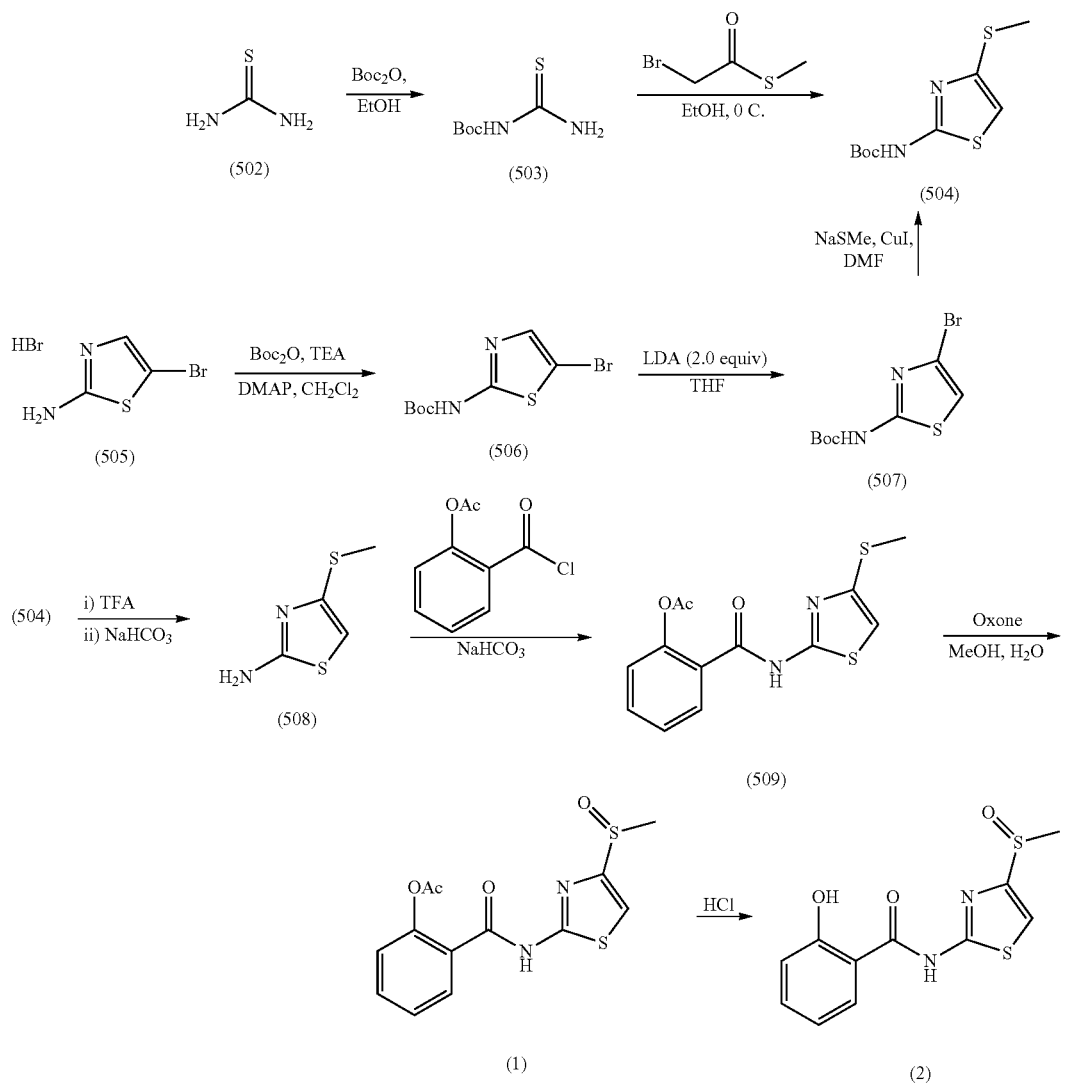

1.5.1.1 Synthesis of tert-butyl 4-(methylthio)thiazol-2-ylcarbamate (504)

N-tert-butoxycarbonylthiourea (503, 0.841 g, 4.77 mmol, prepared according to Schiavi, B.; Ahond, A.; Poupat, C.; Potier, P. Synth. Commun. 2002, 32, 1671) was suspended in ethanol (7.0 mL) and cooled in an ice bath. A solution of S-methyl bromoethanethioate (1.371 g, 5.0582 mmol, prepared according to Praveen Rao, P. N.; Amini, M.; Li, H.; Habeeb, A. G.; Knaus, E. E. J. Med. Chem. 2003, 46, 4872-82) in ethanol (7.0 mL) was added dropwise over 3 minutes. The suspension turned homogeneous at the end of the addition, the bath was removed, and the reaction was stirred at room temperature. The solvent was removed, and the crude material was partitioned between dichloromethane and water. The organics were washed with water and brine. The combined aqueous layers were back-extracted with dichloromethane, and the combined organics were dried with anhydrous $MgSO_4$, filtered, and concentrated in vacuo to an orange glass (stench). The crude material was adsorbed onto ca. 5 g silica gel with ethyl acetate, and flushed through a plug of silica gel with hexanes (discarded) followed by 9:1 hexanes:ethyl acetate. The eluent was evaporated in vacuo to yield 504 (589 mg, 50%) as a colorless solid.

Data for 504: $^1$H-NMR (400 MHz, $CDCl_3$) d 8.93 (br s, 1H), 6.40 (s, 1H), 2.45 (s, 3 H), and 1.47 (s, 9H) ppm; $^{13}$C-NMR (100 MHz, $CDCl_3$) d 160.3, 151.3, 145.4, 105.7, 82.8 (br), 28.2, and 16.2 ppm; MS (ESI+) m/z (rel. intensity): 191.1 (100, M-$(CH_3)_2C$=$CH_2^+$), 173.1 (20), 147.1 (70), 120.0 (10), and 105.0 (10) m/z. MS (ESI-) m/z (rel. intensity): 245.2 (15, M-H$^-$), 171.1 (25), 145.1 (100), 103.0 (20), and 97.0 (20) m/z.

1.5.1.2 Synthesis of tert-butyl (5-bromo-1,3-thiazol-2-yl)carbamate (506)

5-Bromo-1,3-thiazol-2-amine hydrobromide (505, 6.52 g, 25.1 mmol) and 4-dimethylaminopyridine (69.9 mg, 0.572 mmol) were combined under an atmosphere of dry $N_2$, and tetrahydrofuran (40 mL) and triethylamine (15 mL) were added to form a thick off-white suspension. A solution of di-tert-butyldicarbonate (6.06 g, 27.7 mmol) in tetrahydrofuran (24 mL) was added to the above suspension, and the resulting slurry was stirred at room temperature for 4 h. The reaction mixture was then poured onto water (100 mL), and the aqueous was extracted with ethyl acetate. The combined organics were washed with saturated $NaHCO_3$ solution, brine, dried over MgSO4, filtered, and the solvent was removed in vacuo. The crude product was adsorbed onto silica gel, and eluted through a plug of silica gel with 9:1 hexanes:ethyl acetate. The eluent was collected, and evaporated to give 506 (5.42 g, 78%) as a colorless crystalline solid.

Data for 506: $^1$H NMR (400 MHz, DMSO-d6) d 12.75 (br s, 1H), 7.44 (s, 1H), and 1.48 (s, 9H) ppm. $^{13}$C NMR (100 MHz, DMSO-d6) d 160.1, 152.9 (br), 139.0, 100.5, 81.7, and 27.8 ppm. MS (ESI+) m/z (rel. intensity): 225.1 (100, $M^{81}Br-(CH_3)_2C=CH_2^+$), 223.1 (100, $M^{79}Br-(CH_3)_2C=CH_2^+$).

1.5.1.3 Synthesis of tert-butyl (4-bromo-1,3-thiazol-2-yl)carbamate (507)

Tetrahydrofuran (160 mL) and N,N-diisopropylamine (14 mL, 97 mmol) were combined in a 3-neck 500 mL RBF equipped with a stirbar, septum, and an internal temperature probe. The resulting solution was cooled to 0.8° C., and n-butyllithium in hexanes (2.50 M, 38 mL, 95 mmol) was added slowly over ca. 5 min to produce a light yellow solution ($T_{int}$ max=10° C.), which was stirred and allowed to re-cool to near 0° C. A solution of tert-butyl (5-bromo-1,3-thiazol-2-yl) carbamate, 506 (8.74 g, 31.3 mmol) in tetrahydrofuran (30.0 mL) was added dropwise to the above solution over 16 min ($T_{int}$ varied from 0.9° C. to a maximum of 7° C.). The now deep brown reaction mixture was stirred for 15 min before being quenched with water (13 mL), and stirred for an additional 5 minutes. Aqueous saturated NH$_4$Cl (250 mL) and ethyl acetate (250 mL) were added, and the layers were separated. The aqueous was extracted with ethyl acetate, and the combined organics were washed with brine, dried with MgSO$_4$, filtered, and concentrated in vacuo. The crude material was adsorbed onto silica gel with ethyl acetate, and elute through a plug of silica gel with 2 liters of 9:1 hex:EtOAc The eluent was collected, and the solvents were removed to give 507 (8.41 g, 96%) as a colorless solid.

Data for 507: $^1$H NMR (400 MHz, DMSO-d6) d 12.75 (br s, 1H), 7.24 (s, 1H), and 1.48 (s, 9H) ppm. $^{13}$C NMR (400 MHz, CDCl$_3$) d 160.6, 152.7 (br), 119.8, 110.6, 81.7, and 27.9 ppm. MS (ESI+) m/z (rel. intensity): 225.1 (100, $M^{81}Br-(CH_3)_2C=CH_2^+$), 223.1 (100, $M^{79}Br-(CH_3)_2C=CH_2^+$).

1.5.1.4 Alternate Synthesis of tert-butyl (4-methylthio-1,3-thiazol-2-yl)carbamate (504)

tert-Butyl (4-bromo-1,3-thiazol-2-yl)carbamate (507, 3.9575 g, 14.177 mmol), copper(I) iodide (2.7718 g, 14.554 mmol), and sodium methylthiolate (5.0242 g, 71.682 mmol) were combined in a 100 mL flask equipped with a stirbar and a water-jacketed condenser with a septum. The headspace was exchanged for dry nitrogen, and N,N-dimethylformamide (26 mL) was added. The reaction turned canary yellow, and then faded to a dull grey-pink suspension, and was stirred at room temperature for ca. 1 min before lowering into a 136° C. oil bath set to 140° C., and stirred. Over the first 5-10 min of heating, the color faded to a light yellow, and the reaction became homogenous. Out gassing/boiling was observed when stirring was stopped. The reaction was cooled to room temperature after 15 h at 140° C., and HPLC analysis showed complete consumption of starting material. The reaction mixture was diluted with ethyl acetate (ca. 200 mL) and filtered through a pad of celite, eluting with ethyl acetate. The combined organics were washed with 1:1 1 M HCl/saturated NH$_4$Cl solution (250 mL), which resulted in a thick emulsion. The entire mixture was then filtered through amorphous cellulose, and the layers were separated. The organics were than washed with 0.5 M HCl, and saturated NaHCO$_3$ solution. Another very fine powder drops out of solution upon treatment with base. The suspension was again filtered through celite, and the resulting solution was washed with brine, dried with MgSO$_4$, filtered, and concentrated in vacuo to give a green oil (3.17 g). The crude product was adsorbed onto ca. 15 g silica with EtOAc, and dried in vacuo, and eluted through a pad of silica gel (ca. 80 g) with 500 mL hexanes (discarded) and 2 liters of 9:1 hexanes/ethyl acetate, which was concentrated in vacuo to give 504 (2.41 g, 69%) as an off-white solid.

Data for 504 is given above.

1.5.1.5 Synthesis of 4-(methylthio)-1,3-thiazol-2-amine (508)

tert-Butyl[4-(methylthio)-1,3-thiazol-2-yl]carbamate (504, 3.17 g, 12.9 mmol) was dissolved in methylene chloride (130 mL), and trifluoroacetic acid (54 mL) was added to produce a bright yellow solution. The solution was lightly capped and stirred at room temperature for 8 hours, at which point the reaction was complete. The solvents were removed in vacuo and the resultant thick oil was suspended in 0.1 M HCl (50 mL), and the solvent was removed. This was repeated once, and the resulting solids were suspended in ethyl acetate (20 mL) and evaporated to give a finely divided, free-flowing pink solid (2.0 g). The solids were re-suspended in ethyl acetate (20 mL), sonicated, and filtered on a medium frit, washing with ethyl acetate (ca. 30 mL). The lavender solids were partitioned solids between saturated NaHCO$_3$ solution (100 mL) and dichloromethane (100 mL). The layers were separated, and the aqueous layer was extracted once with dichloromethane. The combined organics were then washed with brine, dried with anhydrous MgSO$_4$, filtered, and concentrated in vacuo to give 508 (1.33 g, 71%) as a dark oil, which solidified to a crystalline solid upon point cooling with dry ice, and letting stand.

Data for 508: $^1$H-NMR (400 MHz, DMSO-d6) d 7.06 (br s, 2H), 6.11 (s, 1H), and 2.36 (s, 3H) ppm; $^{13}$C-NMR (100 MHz, DMSO-d6) d 168.5, 144.7, 97.37, and 14.7 ppm; MS (ESI+) m/z (rel. intensity): 147.1 (100, M+H$^+$), 132.0 (20), and 105.0 (40).

1.5.1.6 Synthesis of 2-{[4-(methylthio)-1,3-thiazol-2-yl]carbamoyl}phenyl acetate (509)

4-(Methylthio)-1,3-thiazol-2-amine (508, 672 mg, 4.60 mmol) was dissolved in tetrahydrofuran (10.0 mL) to give a watermelon colored solution, and cooled to zero ° C. A solution of acetylsalicyloyl chloride (0.9915 g) in tetrahydrofuran (1.4 mL) was added dropwise over 1 minute, the bath was removed, and the reaction was stirred while allowing the reaction to warm to room temperature over ca. 40 minutes. Triethylamine (0.670 mL, 4.81 mmol) was added dropwise over 3 minutes to produce a dark suspension that was stirred for 15 hours. The solids were removed from the slurry by filtering on a medium frit, the solids were washed with THF (ca. 20 mL), and the resulting solution was concentrated, dissolved in ethyl acetate, filtered through a plug of magnesol to remove polar colored impurities, and concentrated to give an orange crystalline solid (1.35 g). This crude material was adsorbed onto silica gel with ethyl acetate, and purified by MPLC (eluting 1 liter each 6:1, 4:1, 3:1, and 2:1 Hex:EtOAc). Fractions were pooled and evaporated to give 509 (660.8 mg, 47%) as a near colorless solid.

Data for 509: $^1$H-NMR (400 MHz, DMSO-d6) d 12.69 (br s, 1H), 7.77 (dd, J=7.8, 1.4 Hz, 1H), 7.62 (ddd, J=7.8, 7.8, 1.4 Hz, 1H), 7.40 (ddd, J=7.8, 7.8, 1.4 Hz, 1H), 7.27 (dd, J=8.0, 1.4 Hz, 1H), 6.87 (s, 1H), 2.48 (s, 3H), and 2.22 (s, 3H) ppm; $^{13}$C-NMR (100 MHz, DMSO-d6) d 168.8, 163.9, 158.3, 148.5, 145.2, 132.7, 129.5, 126.5, 125.8, 123.3, 105.4, 20.7, and 15.0 ppm.; MS (ESI+) m/z (rel. intensity): 331.2 (20, M+Na$^+$), 309.3 (25, M+H$^+$), 267.3 (70), 189.2 (30), 147.2 (100), 121.1 (40), 100.1 (20), and 83.1 (65) m/z. MS (ESI−) m/z (rel. intensity): 265.3 (80, M−H$^-$).

1.5.1.7 2-{[4-(Methylsulfinyl)-1,3-thiazol-2-yl]carbamoyl}phenyl acetate (1)

A solution of Oxone® (2.71 g, 4.44 mmol) dissolved in a minimum amount of water (15.0 mL) was added to a cold solution (0° C.) of 509 (0.514 g, 1.47 mmol) dissolved in a minimum amount of methanol (200 mL). On addition of the Oxone® solution a white solid precipitated. Additional methanol (100 mL) was added to the reaction. After stirring 25 min at 0° C., a saturated aqueous solution of $Na_2S_2O_3$ was added to the reaction. The reaction was concentrated to remove excess methanol. The aqueous residue was washed four times with dichloromethane. The combined dichloromethane layers were washed with brine, dried over sodium sulfate and concentrated in vacuo to give crude 1 (0.66 g, >100%) as a white foam. This residue was dissolved in ethyl acetate and loaded onto a 90 g silica gel column that had been pre-equilibrated with ethyl acetate. The column was eluted with ethyl acetate. Like fractions of pure product were combined and concentrated in vacuo. The residue was stirred with ether and evaporated in vacuo to give 1 (0.288 g, 60%) as a white solid. $^1$H-NMR showed clean desired product contaminated with traces of residual dichloromethane and ethyl acetate. HPLC analysis indicated the product to be 95% pure ($t_R$=5.01 min, Condition C) contaminated with 3% of 2 ($t_R$=5.33 min, Condition C).

Approximately one half of this material (0.150 g) of this material was carried on without further purification in the synthesis of 2. The remainder of the material was dissolved in a minimum amount of pyridine. To the reaction was added acetic anhydride (5 μL, 0.050 mmol). After stirring 2 h at room temperature, the reaction was concentrated in vacuo. The residue was stirred with toluene and concentrated in vacuo. This process was repeated several times. The residue was dissolved in dichloromethane. Silica gel was added to the colorless solution and the suspension was concentrated in vacuo. The residue was placed on top of a 40 g silica gel cartridge that had been pre-equilibrated with 10/0.25 dichloromethane/ethanol. The column was eluted with the same solvent system. Like fractions of pure product were combined and concentrated in vacuo. The residue was dissolved in dichloromethane, and concentrated in vacuo to a white solid. The residue was stirred with ether, concentrated in vacuo and dried at 80° C. overnight under vacuo to give 1 (0.105 g, 22%) as a white solid: mp=167.3-169.3° C. HPLC $t_R$=5.01 min (98%, Condition C). $^1$H NMR (400 MHz, DMSO-d6) δ 13.01 (s, 1H), 7.77-7.83 (m, 2H), 7.65 (td, J=2.8 Hz, 1H), 7.42 (td, J=1, 8 Hz, 1H), 7.29 (dd, J=1, 8 Hz, 1H), 2.86 (s, 3H), 2.23 (s, 3H). MS (ESI+) m/z 347.1 (M+Na)+, 325.1 (M+H)+. MS (ESI−) m/z 323.1 (M−H)−

1.5.1.8 2-Hydroxy-N-[4-(methylsulfinyl)-1,3-thiazol-2-yl]benzamide (2)

Into a solution of 1 (0.150 g, 0.425 mmol) and THF (11 mL) was added 2M HCl (16 mL). The reaction was warmed to reflux. After refluxing 2 h, the reaction was allowed to cool to room temperature. A solid formed on standing. The reaction was cooled in an ice bath. The cold suspension was filtered. The filter pad was washed with water. The filtrate was concentrated in vacuo. The residue was suspended in water and filtered and combined with the original filter pad. The combined solids were stirred with a mixture of warm methanol and THF, adding more THF until the mixture became homogeneous. The homogeneous solution was concentrated in vacuo. The white residue was suspended in methanol and concentrated in vacuo four more times. The white residue was stirred with ether, filtered and the filter pad dried under a stream of nitrogen to give to give 2 (0.095 g, 79%) as a white solid: mp=240° C. (dec., begins turning dark then melts 260-261° C.). HPLC $t_R$=5.33 min (100%, Condition C). $^1$H NMR (400 MHz, DMSO-d6) δ 12.18 (br. s., 1H), 11.69 (br. s., 1H), 7.98 (dd, J=2, 8 Hz, 1H), 7.81 (s, 1H), 7.46-7.54 (m, 1H), 6.97-7.10 (m, 2H), 2.86 (s, 3H). MS (ESI+) m/z 305.1 (M+Na)+, 283.1 (M+H)+, MS (ESI−) m/z 281.2 (M−H)−.

1.5.2 General Procedures for the Synthesis of 4-hydroxy-N-[4-(methylsulfinyl)-1,3-thiazol-2-yl]benzamide (4) and 3-hydroxy-N-[4-(methylsulfinyl)-1,3-thiazol-2-yl]benzamide (6)

The compounds 4-hydroxy-N-[4-(methylsulfinyl)-1,3-thiazol-2-yl]benzamide (4) and 3-hydroxy-N-[4-(methylsulfinyl)-1,3-thiazol-2-yl]benzamide (6), may be prepared according to the following general synthetic scheme:

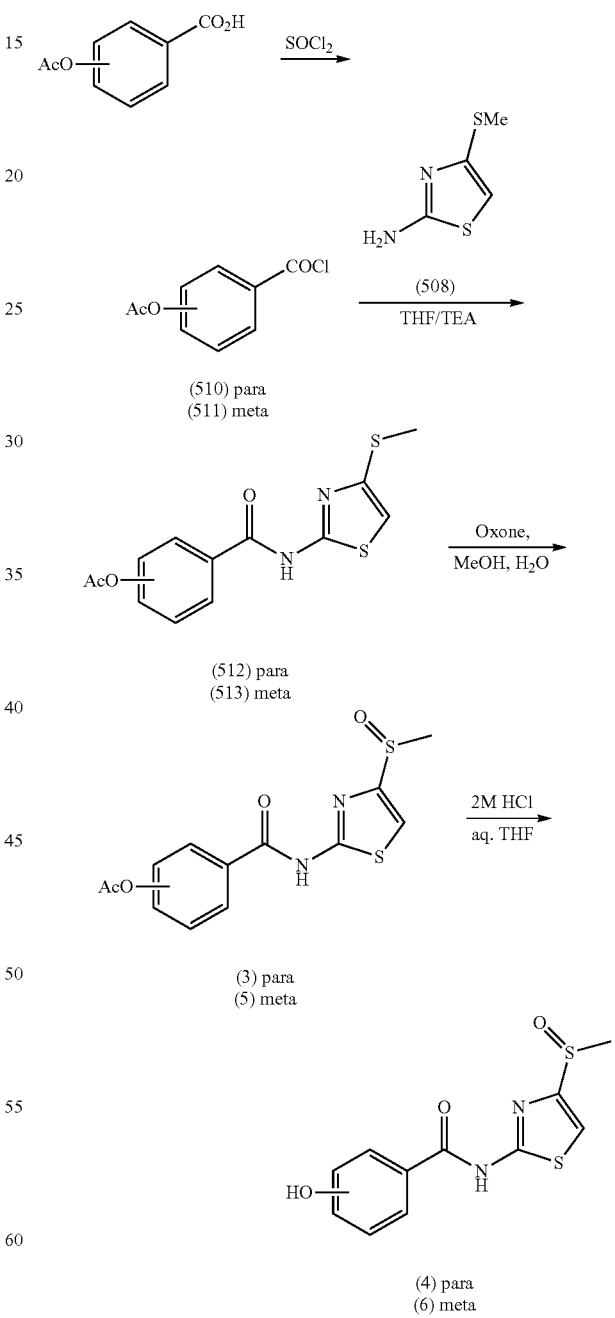

1.5.2.1 Synthesis of 4-(chlorocarbonyl)phenyl acetate (510)

Thionyl chloride (11.1 mL, 15.3 mmol) was added to 4-acetoxybenzoic acid (2.50 g, 13.9 mmol), and the reaction was warmed to reflux. The reaction was cooled after heating for 3.5 hours, and concentrated in vacuo to give a colorless oil. Toluene was added to the residue and the mixture was concentrated in vacuo to remove any residual thionyl chloride. This process was repeated twice more to give 510 (2.54 g, 92%) as a colorless oil. This material was used in the next step without additional purification.

Data for 510: $^1$H-NMR (400 MHz, CDCl$_3$) δ 8.18 (d, J=8.9 Hz, 2H), 7.29 (d, J=8.9 Hz, 2H), 2.36 (s, 3H) ppm.

1.5.2.2 Synthesis of 3-(chlorocarbonyl)phenyl acetate (511)

Using the above procedure, reaction of with thionyl chloride (11.1 mL, 15.3 mmol) and 3-acetoxybenzoic acid (2.50 g, 13.9 mmol) gave 511 (2.72 g, 99%) as a colorless oil. This material was used in the next step without additional purification.

Data for 511: $^1$H-NMR (400 MHz, CDCl$_3$) δ 8.03 (ddd, J=8, 2, 1 Hz, 1H), 7.87 (t, J=2 Hz, 1H), 7.52-7.60 (m, 1H), 7.46 (ddd, J=8, 2, 1 Hz, 1H), 2.37 (s, 3H) ppm.

1.5.2.3 Synthesis of 4-{[4-(methylthio)-1,3-thiazol-2-yl]carbamoyl}phenyl acetate (512)

Into a solution of 510 (0.815 g, 4.10 mmol) and dry THF (20.0 mL) was added a solution of triethylamine (0.572 mL, 4.10 mmol) and dry THF (5.00 mL), followed by a solution of 508 (0.500 g, 3.42 mmol) dissolved in dry THF (15.0 mL). The reaction was stirred at room temperature. After stirring overnight, the reaction was concentrated in vacuo. The residue was partitioned between a saturated aqueous sodium bicarbonate and dichloromethane. The dichloromethane layer was washed a second time with the saturated sodium bicarbonate solution and than twice with aq. 1 M HCl. The dichloromethane layer was dried over anhydrous magnesium sulfate and concentrated in vacuo to give crude 512 (1.15 g, >100%) as a brown solid. The crude product was suspended in diethyl ether, stirred and filtered. The filter pad was washed with ether several times, and dried in vacuo to give 512 (0.692 g, 63%) as a light brown solid.

Data for 512: mp=185.7-188.7° C.; $^1$H-NMR (400 MHz, DMSO-d$_6$) δ 12.8 (s, 1H), 8.14 (d, J=8.9 Hz, 2H), 7.32 (d, J=8.9 Hz, 2H), 6.89 (s, 1H), 2.50 (s, 3H), 2.31 (s, 3H) ppm; MS (ESI+) m/z (rel. intensity): 100.1 (37), 122.2 (98.3), 163.2 (49), 309.2 (100), 331.2 (29) m/z. MS (ESI−) m/z (rel. intensity): 111.0 (16), 203.2 (31), 307.2 (100).

1.5.2.4 Synthesis of 3-{[4-(methylthio)-1,3-thiazol-2-yl]carbamoyl}phenyl acetate (513)

Into a solution of 511 (0.815 g, 4.10 mmol) and dry THF (25.0 mL) was added triethylamine (0.572 mL, 4.10 mmol), followed by a solution of the 508 (0.500 g, 3.42 mmol) dissolved in dry THF (10.0 mL). The reaction was stirred at room temperature.

After stirring overnight, the reaction was concentrated in vacuo. The residue was dissolved in ethyl acetate and washed once with water, three times with saturated aqueous. sodium bicarbonate solution, and once with brine. The ethyl acetate solution was dried over anhydrous sodium sulfate and concentrated in vacuo to give crude 513 (1.28 g, >100%) as a red foam. The crude product was dissolved in dichloromethane. Silica gel was added to the dichloromethane solution and the suspension was concentrated in vacuo. The residue was loaded on top of a 90 g silica gel cartridge and eluted down the column using a solution of 20% ethyl acetate in hexane. Appropriate fractions of the major product were combined and concentrated in vacuo to give 513 (0.614 g, 58%) as a tan solid. This material was used in the next step without further purification.

Data for 513: $^1$H-NMR (400 MHz, DMSO-d$_6$) δ 12.8 (s, 1H), 8.01 (d, J=8 Hz, 1H), 7.87 (t, J=2 Hz, 1H), 7.60 (t, J=8 Hz, 1H), 7.42 (ddd, J=8, 2, 1 Hz, 1H), 6.90 (s, 1H), 2.50 (s, 3H), 2.32 (s, 3H) ppm.

1.5.2.5 Synthesis of 4-{[4-(methylsulfinyl)-1,3-thiazol-2-yl]carbamoyl}phenyl acetate (3)

Using the Oxone® procedure as described in section 1.5.1.7 for the synthesis of compound (I), a solution of Oxone® (3.68 g, 6.00 mmol) is dissolved in a minimum amount of water (30.0 mL) and is added to a cold solution (0° C.) of 512 (0.63 g, 2.0 mmol) dissolved in a minimum amount of methanol (200 mL). Workup and purification by flash chromatography affords 3 as an off-white solid.

1.5.2.6 Synthesis of 3-{[4-(methylsulfinyl)-1,3-thiazol-2-yl]carbamoyl}phenyl acetate (5)

Using the above procedure for compound (3), 513 (0.61 g, 2.0 mmol) gives crude 5 as a white solid. The crude product is stirred in diethyl ether (30 mL) for 30 minutes, filtered and air dried to give 5 as a white solid.

1.5.2.7 Synthesis of 4-hydroxy-N-[4-(methylsulfinyl)-1,3-thiazol-2-yl]benzamide (4)

2 M hydrochloric acid (3.0 mL) is added to a suspension of 3 (0.12 g, 0.33 mmol) in tetrahydrofuran (3.0 mL), and the resulting suspension is warmed to reflux. The reaction becomes homogeneous upon heating. After refluxing for 1.5 h, the reaction is allowed to cool to room temperature, and is then partitioned between diethyl ether and water. The ether layer is washed with water, saturated aqueous sodium bicarbonate, and brine. The ether layer is dried with anhydrous sodium sulfate and concentrated in vacuo. The residue is triturated with ethyl acetate, the solvent is removed under a stream of nitrogen, and the resulting solid is dried in vacuo at 55° C. to give 4 as a light yellow solid.

1.5.2.8 Synthesis of 3-hydroxy-N-[4-(methylsulfinyl)-1,3-thiazol-2-yl]benzamide (6)

Using the above procedure for example 4, compound 5 (0.34 g, 1.0 mmol) is dissolved in tetrahydrofuran (10 mL) and 2 M hydrochloric acid (10 mL) and gives 6 as a white solid after the ether layer was concentrated in vacuo.

1.5.3 General Procedures for the Synthesis of 4-hydroxy-N-[5-(methylsulfinyl)-1,3-thiazol-2-yl]benzamide (9) and 3-hydroxy-N-[5-(methylsulfinyl)-1,3-thiazol-2-yl]benzamide (10)

The compounds 4-hydroxy-N-[5-(methylsulfinyl)-1,3-thiazol-2-yl]benzamide (9) and 3-hydroxy-N-[5-(methylsulfinyl)-1,3-thiazol-2-yl]benzamide (10) may be prepared according to the following general synthetic scheme:

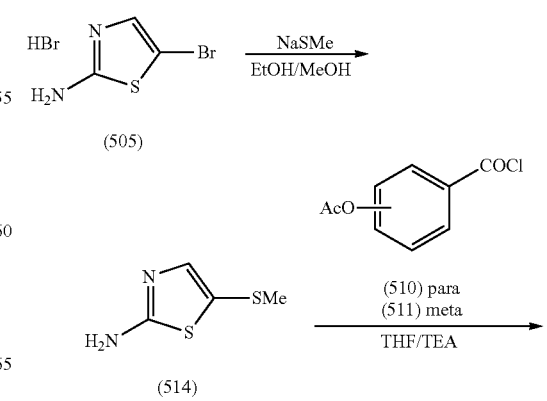

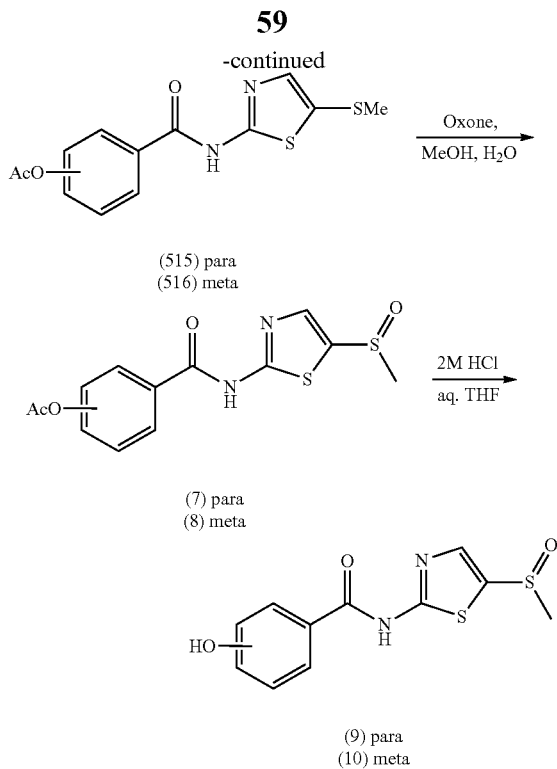

(515) para
(516) meta (7) para
(8) meta (9) para
(10) meta 1.5.3.1 Synthesis of 5-(methylthio)-1,3-thiazol-2-amine (514)

A solution of sodium thiomethoxide (1.09 g, 14.8 mmol) dissolved in methanol (18.0 mL) was added to a suspension of 2-amino-5-bromothiazole monohydrobromide 505 (2.50 g, 14.0 mmol) in anhydrous ethanol (18.0 mL) over 5 minutes. The reaction became homogeneous. A second solution of sodium thiomethoxide (1.09 g, 14.8 mmol) dissolved in methanol (12.0 mL) was added to the reaction. The reaction was warmed to 45° C. for 40 minutes then the heat was removed and the reaction was allowed to stir at room temperature overnight, when thin layer chromatography (1:1 EtOAc/Hexane) indicated most of the starting material consumed along with the formation of a new product. Additional sodium thiomethoxide (0.20 g, 2.85 mmol) was added to the reaction and the reaction was re-warmed to 50° C. After heating for 2 hours, the reaction was cooled to room temperature and concentrated in vacuo. The residue was dissolved in dichloromethane and washed three times with water, once with brine, dried over anhydrous sodium sulfate and concentrated in vacuo to give 514 (1.12 g, 55%) as an orange solid.

Data for 514: $^1$H-NMR (400 MHz, DMSO-$d_6$) δ 7.20 (s, 2H), 6.97 (s, 1H), 2.29 (s, 3 H) ppm.

1.5.3.2 Synthesis of 4-{[5-(methylsulfanyl)-1,3-thiazol-2-yl]carbamoyl}phenyl acetate (515)

Following the procedure for the synthesis of example 512, intermediate 510 (0.815 g, 4.10 mmol) dissolved in dry THF (25.0 mL), triethylamine (0.572 mL, 4.10 mmol), and 514 (0.500 g, 3.42 mmol) dissolved in dry THF (10.0 mL) gave 515 (0.887 g, 84%) as a tan solid.

Data for 514: m.p.=193.3-195.5° C.; $^1$H-NMR (400 MHz, DMSO-$d_6$) δ 12.8 (br. s., 1H), 8.13 (d, J=8.71 Hz, 2H), 7.58 (s, 1H), 7.32 (d, J=8.71 Hz, 2H), 2.46 (s, 3H), 2.31 (s, 3H) ppm; MS (ESI+) m/z (rel. intensity): 121.0 (100), 163.2 (48), 309.2 (34) m/z. MS (ESI−) m/z (rel. intensity): 292.2 (100), 307.3 (48).

1.5.3.3 Synthesis of 3-{[5-(methylsulfanyl)-1,3-thiazol-2-yl]carbamoyl}phenyl acetate (516)

Following the procedure for the synthesis of example 513, intermediate 511 (0.815 g, 4.10 mmol) dissolved in dry THF (25.0 mL), triethylamine (0.572 mL, 4.10 mmol), and 514 (0.500 g, 3.42 mmol) dissolved in dry THF (10.0 mL) gave 516 (0.681 g, 65%) as a tan solid.

Data for 516: m.p.=135.2-136.2° C.; $^1$H-NMR (400 MHz, DMSO-$d_6$) δ 12.8 (s, 1H), 7.96-8.03 (m, 1H), 7.86 (t, J=2 Hz, 1H), 7.57-7.63 (m, 2H), 7.43 (ddd, J=8, 2, 1 Hz, 1H), 2.47 (s, 3H), 2.32 (s, 3H) ppm; MS (ESI+) m/z (rel. intensity): 121.0 (40), 163.2 (100), 309.2 (85), 331.2 (11) m/z; MS (ESI−) m/z (rel. intensity): 292.3 (100), 307.3 (49).

1.5.3.4 Synthesis of 4-{[5-(methylsulfinyl)-1,3-thiazol-2-yl]carbamoyl}phenyl acetate (7)

Using the Oxone® procedure as described in section 1.5.1.7 for the synthesis of compound (I), 515 (0.841 g, 2.73 mmol) gives crude 7. The crude product is stirred with chloroform (50 mL) and the suspension is filtered. The pad is washed once with chloroform and air dried to give pure 7 (0.35 g) as a white solid.

1.5.3.5 Synthesis of 3-{[5-(methylsulfinyl)-1,3-thiazol-2-yl]carbamoyl}phenyl acetate (8)

A solution of m-chloroperbenzoic acid (0.458 g, 2.04 mmol, maximum 77%) is dissolved in dichloromethane (8.0 mL) and added dropwise over 15 minutes to a solution of 516 (0.630 g, 2.04 mmol) dissolved in dichloromethane (25.0 mL). The reaction is stirred at room temperature for 6 hours. The reaction is then partitioned between dichloromethane and saturated aqueous sodium thiosulfate. The organic layer is washed again with a saturated aqueous sodium thiosulfate, twice with saturated aqueous sodium bicarbonate and once with brine. The dichloromethane layer is dried over magnesium sulfate and concentrated in vacuo to give crude 8 (0.704 g, >100%), which is contaminated with traces of residual 3-chlorobenzoic acid. The crude product is re-dissolved in ethyl acetate and washed three times with a saturated aq. sodium bicarbonate, dried using magnesium sulfate and concentrated in vacuo to give a tan solid. The residue is dissolved in THF, and the light brown solution was filtered through a plug of Magnesol. The filter pad is washed well with THF, and the colorless filtrate is concentrated in vacuo to give 8 as a white solid.

1.5.3.6 Synthesis of 4-hydroxy-N-[5-(methylsulfinyl)-1,3-thiazol-2-yl]benzamide (9)

2 M hydrochloric acid (45.0 mL) is added to a suspension of 7 (0.439 g, 1.32 mmol) in tetrahydrofuran (20.0 mL), and the suspension is warmed to reflux. The reaction became homogeneous upon heating. After refluxing for 4 hours, the reaction is allowed to cool to room temperature, and stood at room temperature overnight before the reaction is filtered. The filter pad is washed with water then dried in vacuo at 70° C. to give 9 as a white crystalline solid.

1.5.3.7 Synthesis of 3-hydroxy-N-[5-(methylsulfinyl)-1,3-thiazol-2-yl]benzamide (10)

2 M hydrochloric acid (40.0 mL) is added to a suspension of 8 (0.370 g, 1.13 mmol) in tetrahydrofuran (17.0 mL), and the reaction is warmed to reflux. The reaction becomes homogeneous upon heating. After refluxing for 4 hours, the reaction is allowed to cool to room temperature, and is concentrated in vacuo. The residue is suspended in water and filtered. The filter pad is washed with water, air dried, and then re-dissolved in a minimum amount of warm THF. Water is added to the warm THF solution until the solution turns turbid, and the resulting mixture is allowed to cool to room temperature. Additional water is added, and a white solid forms on standing. The crystalline product is filtered, and the filter pad is washed with water, and dried in vacuo at 70° C. and gives 10 as a white crystalline solid.

1.5.4 Synthesis of 2-hydroxy-N-(5-(methylsulfinyl)thiazol-2-yl)benzamide (12)

The compound, 2-hydroxy-N-(5-(methylsulfinyl)thiazol-2-yl)benzamide (12), may be prepared according to the following synthetic scheme:

1.5.4.2 Synthesis of 2-(5-(methylthio)thiazol-2-ylcarbamoyl)phenyl acetate (518)

Under nitrogen a solution of acetylsalicyloyl chloride (1.24 g, 6.20 mmol, 1.3 eq) in THF (40 mL) was added to a stirred solution of 5-(methylthio)thiazol-2-amine 514 (700.0 mg, 4.79 mmol, 1.0 eq) in dry THF (5 mL). This was followed by the addition of triethylamine (0.67 mL, 4.79 mmol, 1.0 eq). The reaction mixture was stirred at room temperature and

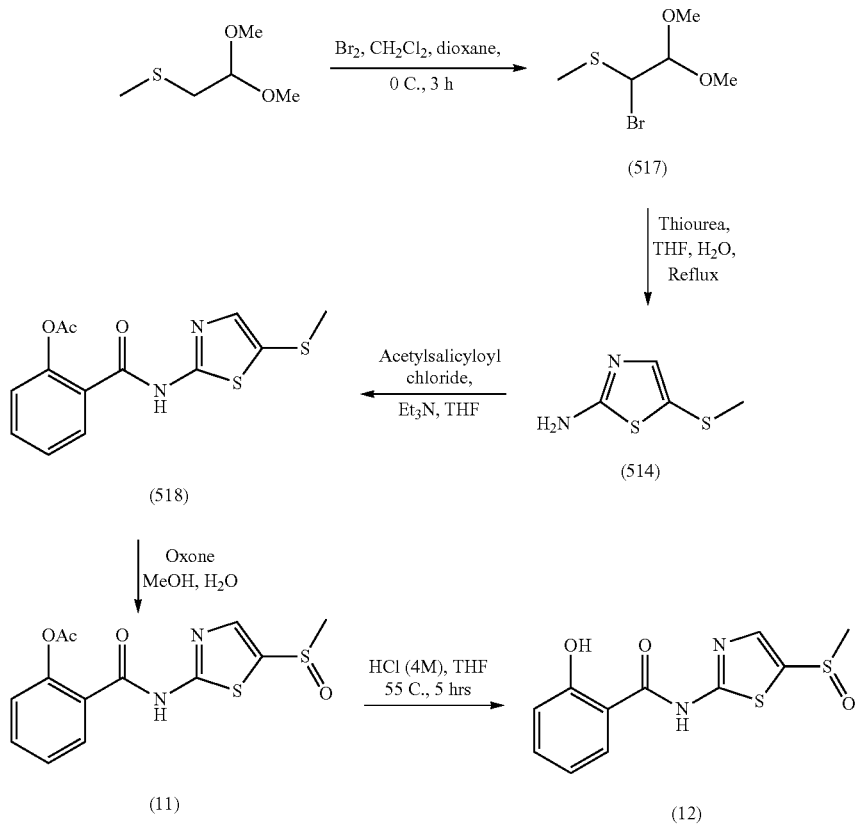

1.5.4.1 Alternate Synthesis of 5-(methylthio)thiazol-2-amine (514)

A solution of bromine (1.9 mL, 37.1 mmol, 1.01 eq.) and dioxane (0.1 cm$^3$, 0.3 eq.) in DCM (20 mL) was added dropwise to a stirred solution of (methylthio)acetaldehyde dimethyl acetal (5.00 g, 36.7 mmol, 1.0 eq.) in DCM (80 mL) at 0° C. over three hours. This mixture was allowed to warm to room temperature and stirred at this temperature for 30 minutes until NMR analysis revealed the disappearance of starting material. DCM was removed under vacuo. Crude bromide 517 was dissolved in THF (50 mL), which was followed by the addition of solution of thiourea (5.58 g, 2.0 eq) in THF (100 mL) and water (20 mL). The solution was refluxed overnight. Solvent was removed under vacuo and the crude product was extracted with EtOAc (50 mL) three times. The combined organic layers were washed with brine solution and dried over anhydrous MgSO$_4$. Product purification through flash column chromatography gave the required product, 2-amino-5-methylthiothiazole 514 (1.35 g, 25.2% yield), as a brown solid.

Data for 514: TLC (silica gel) $R_f$=0.2 (1:1, Hex:EtOAc); $^1$H-NMR (CDCl$_3$, 200 MHz), 2.35 (3H, s, CH$_3$), 5.46 (2H, s, NH$_2$), 7.06 (1H, s, CH); $^1$H (DMSO-d, 400 MHz), 2.29 (3H, s, CH$_3$), 6.96 (1H, s, CH), 7.16 (2H, s, NH$_2$); $^{13}$C-NMR (100 MHz, DMSO-d), 22.6, 115.8, 144.9, 171.8; m/z (CI+H)$^+$ 147; HRMS. found, m/z 147.00540, C$_4$H$_7$N$_2$S$_2$ (MH$^+$) requires m/z, 147.00507 (+2.4 ppm).

monitored by TLC. After two hours, reaction was filtered through sintered funnel and solvent removed in vacuo. The crude product was dissolved in EtOAc (150 mL) and washed twice each with 1M HCl and saturated aq. sodium hydrogen carbonate solutions. The organic fraction was dried over MgSO$_4$ followed the removal of solvent. Flash column chromatography yielded the pure product 518 (1.450 g, 98%) as a solid.

Data for 518: m.p.=145-147° C.; TLC (silica gel) $R_f$=0.36 (Hex:EtOAc, 1:1);

$^1$H-NMR (DMSO-d, 400 MHz), 2.23 (3H, s, CH$_3$), 2.47 (3H, s, CH$_3$), 7.28 (1H, dd, J=1.0, 8.0 Hz, ArH), 7.41 (1H, td, J=1.0, 7.6 Hz, ArH), 7.56 (1H, s, CH), 7.63 (1H, td, J=1.7, 8.0 Hz, ArH), 7.78 (1H, dd, J=1.7, 7.6 Hz, ArH), 12.70 (1H, s, NH); $^{13}$C-NMR (DMSO-d, 100 MHz), 21.1, 22.0, 123.7, 124.6, 126.2, 126.9, 130.0, 133.1, 141.6, 148.9, 160.0, 164.5, 169.2; m/z (CI) 309 (MH$^+$); HRMS. found 309.03654, C$_{13}$H$_{13}$N$_2$O$_3$S$_2$ requires 309.03677, (−0.8 ppm).

1.5.4.3 Synthesis of 2-(5-(methylsulfinyl)thiazol-2-ylcarbamoyl)phenyl acetate (11)

Using the Oxone® procedure as described in section 1.5.1.7 for the synthesis of compound (1), 518 (1.1 g, 3.57 mmol), affords 11 as a white solid.

1.5.4.4 Synthesis of 2-hydroxy-N-(5-(methylsulfinyl)thia-zol-2-yl)benzamide (12)

A solution of 11 (1.0 g, 3.1 mmol) is dissolved in THF (20 mL) and is added under stirring to 2M HCl (100 mL). The reaction is refluxed for one hour and is allowed to cool under stirring over one hour. The product is filtered using a sintered glass funnel, washed with distilled water and THF and dried in high vacuum and affords 12 as a colorless solid.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

2. Antiviral Test Results

Against genotype G2a, NTZ, used as a reference inhibitor, and compound 2 were shown to inhibit J6/JFH-1HCV replication at a 1 µM test concentration. At 1 µM, the relative activity of compound 2 was estimated to be 95% of NTZ, while the relative potency of compound 2 at 0.1 µM was estimated to be 88% of NTZ. Neither of these compounds showed a cytotoxic effect when tested as described herein in Huh 7.5 cells. Based on the G1b and G1a replcon cell assay data (Table 2), the observed potency of compound 2 in the infectious G2a assay was quite unexpected and suggests it is nearly equipotent to NTZ at the given test concentrations.

Table 2 presents data from the primary and secondary HCV replicon cell assays using the six reference compounds NTZ, TIZ, RM5014, RM5015, RM4863, and RM4864 vs. the new methylsulfinyl thiazolides 1 and 2.

wherein $R_1$ is selected from the group consisting of hydrogen and Q-C(=O)—, any of which may be optionally substituted;

$R_2$ to $R_5$ are independently selected from the group consisting of hydrogen, D, hydroxy, F, Cl, Br, CN, $NO_2$, $(C_1-C_6)$-alkyl, $(C_3-C_8)$-cycloalkyl, $(C_1-C_6)$-alkoxy, carboxy, $(C_1-C_6)$-alkoxycarbonyl, amino, $(C_1-C_6)$-acylamino, amido, $(C_1-C_6)$-alkylamido, $(C_1-C_6)$-dialkylamido, $(C_1-C_6)$-alkylsulfonylamino, $(C_1-C_6)$-haloalkyl, $(C_1-C_6)$-perhaloalkyl, $(C_1-C_6)$-perhaloalkoxy, $(C_1-C_6)$-alkyithio, $(C_1-C_6)$-alkylthioalkyl, $(C_1-C_6)$-alkylsulfonyl, $(C_3-C_8)$-cycloalkylsulfonyl, arylsulfonyl, arylalkylsulfonyl, heteroarylsulfonyl, heteroarylalkylsulfonyl, $(C_1-C_6)$-alkylsulfonamido, N,N'-$(C_1-C_6)$-dialkylsulfonamido, aryl, aryloxy, arylthio, arylalkylthio, heteroaryl, heteroaryloxy, heteroarylalkoxy, heteroarylthio, heteroarylalkylthio, heterocycloalkyl, heterocycloalkoxy, and Q-C(=O)—, any of which may be optionally substituted; or any two contiguous $R_1$, $R_2$ or $R_3$ moieties may be combined together with the atoms to which they are attached and joined to form an optionally substituted 5-to 8-membered heterocycloalkyl ring;

wherein when one of $R_6$ or $R_7$ is hydrogen, the other is independently selected from the group consisting of $(C_1-C_6)$-alkylsulfinyl, $(C_1-C_6)$alkylsulfinyalkyl, $(C_2-C_6)$-alkenylsulfinyl, $(C_2-C_6)$-alkynylsulfinyl, $(C_3-C_8)$-cycloalkylsulfinyl, $(C_5-C_8)$-cycloalkenylsulfinyl, arylsulfinyl, arylalkylsulfinyl, arylalkenylsulfinyl, heteroarylsulfinyl, heteroarylalkylsulfinyl, heteroarylalkenylsulfinyl, and heterocycloalkylsulfinyl, any of which may be optionally substituted; or the $R_6$ and $R_7$

TABLE 2

Antiviral activity of Alkylsulfinyl thiazolides against HCV Genotypes 1b and 1a in cell culture.

| DRUG NAME | PRIMARY ASSAY | | | | SECONDARY ASSAY, GENOTYPE 1B | | | | SECONDARY ASSAY, GENOTYPE 1A | | | |
|---|---|---|---|---|---|---|---|---|---|---|---|---|
| | CC50 (uM) | EC50 (uM) | EC90 (uM) | SI | CC50 (uM) | EC50 (uM) | EC90 (uM) | SI | CC50 (uM) | EC50 (uM) | EC90 (uM) | SI |
| NTZ | 31.0 | 0.21 | 0.98 | 148.0 | 35.0 | 0.25 | 0.95 | 143.0 | 49.0 | 0.33 | 1.10 | 149.0 |
| TIZ | 15.0 | 0.15 | 0.81 | 100.0 | 28.0 | 0.19 | 0.92 | 142.0 | 27.0 | 0.23 | 1.00 | 119.0 |
| RM5014 | >100.0 | >10.0 | >10.0 | | | | | | | | | |
| RM5015 | 2.8 | 0.038 | 0.59 | 74.0 | | | | | | | | |
| RM5015 | 74.0 | 0.93 | 2.80 | 79.0 | | | | | | | | |
| RM4864 | 20.0 | >10.0 | >10.0 | | | | | | | | | |
| RM4863 | 43.0 | 1.50 | 5.2 | 29.0 | >10.0 | 0.9 | 8.8 | >11.1 | >10.0 | 0.80 | 3.40 | >12.3 |
| RM5010 | >100.0 | >10.0 | >10.0 | | | | | | | | | |
| RM5011 | 63.0 | 2.00 | 4.60 | 32.0 | >100.0 | 2.20 | 6.1 | >45.5 | >100.0 | 2.80 | >5.0 | >35.7 |

The invention claimed is:

1. A compound of structural Formula (1):

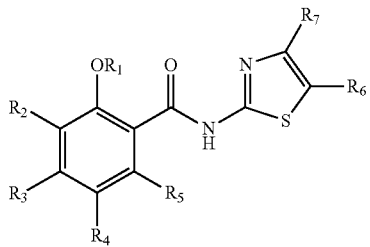

(I)

and pharmaceutically acceptable salts thereof, moieties may be combined together with the atoms to which they are attached and joined to form an optionally substituted 5-to 8-membered ring that incorporates a sulfinyl (—S[O]—) moiety; and wherein Q is $R_8$, $OR_8$, $NHR_8$, or $NR_8R_9$; $R_8$ and $R_9$ are independently selected from the group consisting of hydrogen, $(C_1-C_{12})$-alkyl, $(C2-C_{12})$-alkenyl, $(C_2-C_{12})$-alkynyl, $(C_3-C_8)$-cycloalkyl, aryl, arylalkyl, arylalkenyl, heterocycloalkyl, heteroaryl, heteroarylalkyl, and heteroarylalkenyl, any of which may be optionally substituted; or $R_8$ and $R_9$, together with the atoms to which they are attached, may be joined to form an optionally substituted 5-to 8-membered heterocycloalkyl ring; any of which may be optionally substituted.

2. The compound according to claim 1, $R_2$ to $R_5$ are independently selected from the group consisting of hydrogen, D, hydroxy, F, Cl, Br, CN, $NO_2$, ($C_1$-$C_6$)-alkyl, ($C_3$-$C_6$)-cycloalkyl, ($C_1$-$C_6$)-alkoxy, ($C_1$-$C_6$)-alkoxycarbonyl, ($C_1$-$C_6$)dialkylamido, ($C_1$-$C_3$)-haloalkyl, ($C_1$-$C_4$)-perhaloalkyl, ($C_1$-$C_4$)-perhaloalkoxy, ($C_1$-$C_6$)-alkylthio, ($C_1$-$C_6$)-alkylsulfonyl, ($C_3$-$C_6$)-cycloalkylsulfonyl, arylsulfonyl, arylalkylsulfonyl, heteroarylsulfonyl, heteroarylalkylsulfonyl, aryl, aryloxy, arylthio, heteroaryl, heteroaryloxy, heterocycloalkyl, and heterocycloalkoxy, any of which may be optionally substituted;

wherein when one of $R_6$ or $R_7$ is hydrogen, the other is independently selected from the group consisting of ($C_1$-$C_6$)-alkylsulfinyl, ($C_1$-$C_6$)-alkylsulfinylalkyl, ($C_3$-$C_8$)-cycloalkylsulfinyl, ($C_5$-$C_8$)-cycloalkenylsulfinyl, arylsulfinyl, arylalkylsulfinyl, heteroarylsulfinyl, heteroarylalkylsulfinyl, and heterocycloalkylsulfinyl, any of which may be optionally substituted; or the $R_6$ and $R_7$ moieties may be combined together with the atoms to which they are attached and joined to form an optionally substituted 5- to 7-membered ring that incorporates a sulfinyl (—S[O]—) moiety; and wherein Q is $R_8$, $OR_8$, $NHR_8$, or $NR_8R_9$; $R_8$ and $R_9$ are independently selected from the group consisting of hydrogen, ($C_1$-$C_{12}$)-alkyl, ($C_2$-$C_{12}$)-alkenyl, ($C_3$-$C_8$)-cycloalkyl, aryl, arylalkyl, arylalkenyl, heterocycloalkyl, heteroaryl, heteroarylalkyl, and heteroarylalkenyl, any of which may be optionally substituted; or $R_8$ and $R_9$, together with the atoms to which they are attached, may be joined to form an optionally substituted 5-to 7-membered heterocycloalkyl ring; any of which may be optionally substituted.

3. The compound according to claim 2,
wherein $R_2$ to $R_5$ are independently selected from the group consisting of hydrogen, D, F, Cl, Br, CN, ($C_1$-$C_6$)-alkyl ($C_3$-$C_6$)-cycloalkyl, ($C_1$-$C_6$)-alkoxy, ($C_1$-$C_3$)-haloalkyl, ($C_1$-$C_4$)-perhaloalkyl, ($C_1$-$C_4$)-perhaloalkoxy, ($C_1$-$C_6$)-alkyithio, aryl, aryloxy, heteroaryl, heteroaryloxy, heterocycloalkyl, and heterocycloalkoxy, any of which may be optionally substituted: and
wherein $R_7$ is hydrogen and $R_6$ is independently selected from the group consisting of ($C_1$-$C_6$)-alkylsulfinyl, ($C_1$-$C_6$)-alkylsulfinylalkyl, ($C_3$-$C_6$)-cycloalkylsulfinyl, arylsulfinyl, arylalkylsulfinyl, heteroarylsulfinyl, heteroarylalkylsulfinyl, and heterocycloalkylsulfinyl, any of which may be optionally substituted; or the $R_6$ and $R_7$ moieties may be combined together with the atoms to which they are attached and joined to form an optionally substituted 5- to 7-membered ring that incorporates a sulfinyl (—S[O]—) moiety.

4. The compound according to claim 3,
wherein $R_2$ to $R_5$ are independently selected from the group consisting of hydrogen, D, F. Cl, Br, CN, ($C_1$-$C_6$)-alkyl, ($C_3$-$C_6$)-cycloalkyl, ($C_1$-$C_6$)-alkoxy, ($C_1$-$C_3$)-haloalkyl, ($C_1$-$C_4$)-perhaloalkyl, ($C_1$-$C_4$)-perhaloalkoxy, and ($C_1$-$C_6$)-alkylthio, any of which may be optionally substituted.

5. The compound according to claim 4,
wherein $R_1$ is selected from the group consisting of hydrogen, and Q is selected from hydrogen, methyl, ethyl, n-propyl, isopropyl, n-butyl, 2-methyl-1-propyl, sec-butyl, tert-butyl, 2,3-dimethylbutan-2-yl, cyclohexyl, 2,6-dimethylcyclohexyl, 1-methylcyclohexyl, phenyl, 4-pyridyl, benzyl, 4-pyridylmethyl, phenylethyl, (S)-1-hydroxy-(phenylethyl), 2-pyrazinyl, phenyethenyl, (E)-2-(4-pyridazinyl)-1-ethenyl, (E)-4-(2-)-1H-imidazolyl-1-ethenyl, 3-acetoxyl-1-propyl, ethoxycarbonylethyl, methoxylcarbonylpropyl, N-methylaminocarbonylethyl, N-ethylaminocarbonylpropyl, 3-(N-ethylaminocarbonyl)-2,2-dimethyl-1-propyl, N-(morpholinoethyl)aminocarbonylethyl, 3-pyridylmethylaminocarbonylethyl, 4-pyridylmethylaminocarbonylethyl, 4-pyridylmethylaminocarbonylpropyl, carboxyethyl, carboxypropyl, 2-piperidinyl,3-piperidinyl, 4-piperidinyl, 2-piperazinyl, (S)-1-aminoethyl, (R)-1-aminoethyl, (S)-1-aminoisobutyl, 1-aminocyclopropyl, methoxy, ethoxy, isopropoxy, isobutoxy, neopentyloxy, cyclohexyloxy, 4-piperdinyloxy,3-acetoxy-2methyl-1-propoxy, tert-pentyloxy, 4-acetoxybenzyloxy, 3-(4-acetoxyphenyl)-2-propenyloxy, (E)-2-methyl-4-(2-oxo-2,3-dihydrobenzofuran-5-yl)but-3-en-2-yloxy, pivaloyloxymethoxy, pivaloyloxy-1-ethoxy, isopropoxycarbonyloxymethoxy, isopropoxycarbonyloxy-1-ethoxy, amino, N-methylamino, N-ethylamino N,N-dimethylamino, N-propylamino, N-isopropylamino, N-butylamino, N-piperidinyl, N-piperazinyl, N-4methylpiperazinyl, N-cyclohexylamino, N-benzylamino, N-(2,4-dimethoxy)benzylamino, 2-(N-methylcarboxamido)phenylamino, N-methyl-2-hydroxyethylamino, $N^1,N^2$-dimethyl-1,2-ethanediamin-1yl, $N^1$, $N^2$-diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl.

6. The compound according to claim 5,
wherein $R_2$ to $R_5$ are independently selected from the group consisting of hydrogen, D, F, Cl, CN, methyl, ethyl, n-propyl, isopropyl, n-hexyl, cyclopropyl, methoxy, ethoxy, isopropoxy, trifluoromethyl, tetrafluroethoxy, methylthio, and t-butylthio, any of which may be optionally substituted; and
wherein $R_6$ is selected from the group consisting of methylsulfinyl, ethylsulfinyl, isopropylsulfinyl, methylsulfinylmethyl, 2-(ethylsulfinyl)ethyl, t-butylsulfinylmethyl, cyclopropylsulfinyl, cyclopentylsulfinyl, phenylsulfinyl, benzylsulfinyl, phenethylsulfinyl, 2-pyridylsulfinyl, 2-pyrazinylsulfinyl, 4-thiazolylsulfinyl, 4-pyridylmethylsulfinyl, 3-thienylmethylsulfinyl, 4-piperidinylsulfinyl, tetrahydro-2H-pyranylsulfinyl, any of which may be optionally substituted.

7. The compound according to claim 6,
wherein $R_1$ is selected from the group consisting of hydrogen and $R_8$ and $R_9$in Q-C(=O)— is selected from the group consisting of methyl, ethyl, ethoxy, isopropoxy, isobutoxy, phenyl, phenylethenyl, 4-piperidinyl, N-piperazinyl, N-(2,4-dimethoxy)benzylamino, 2-(N-methylcarboxamido)-phenylamino, $N^1$, $N^2$-dimethyl-1,2-ethanediamin-1-yl, $N^1,N^2$-dimethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl;
wherein $R_2$ to $R_5$ are independently selected from the group consisting of hydrogen, F, Cl, methyl, ethyl, cyclopropyl, methoxy, ethoxy, trifluoromethyl and methylthio, any of which may be optionally substituted; and
wherein $R_6$ is selected from the group consisting of methylsulfinyl, ethylsulfinyl, isopropylsulfinyl, methylsulfinylmethyl, t-butylsulfinylmethyl, cyclopropylsulfinyl, and benzylsulfinyl.

8. The compound according to claim 7,
wherein $R_1$ is selected from the group consisting of hydrogen and Q-C(=O)—, where $R_8$ is methyl;
wherein $R_2$ through $R_5$ are hydrogen; and
wherein $R_6$ is methylsulfinyl.

9. The compound according to claim 2, wherein to $R_2$ to $R_5$ are independently selected from the group consisting of hydrogen, D, F, Cl, Br, CN, $(C_1-C_6)$-alkyl, $(C_3-C_6)$-cycloalkyl, $(C_1-C_6)$-alkoxy, $(C_1-C_3)$-haloalkyl, $(C_1-C_4)$-perhaloalkyl, $(C_1-C_4)$-perhaloalkoxy, $(C_1-C_6)$-alkylthio, aryl, aryloxy, heteroaryl, heteroaryloxy, heterocycloalkyl, and heterocycloalkoxy, any of which may be optionally substituted; and wherein $R_6$ is hydrogen and is independently selected from the group consisting of $(C_1-C_6)$alkysulfinyl, $(C_1-C_6)$-alkysulfinylalkyl, $(C_3-_6)$-cycloalkylsulfinyl, arylsulfinyl, arylalkylsulfinyl, heteroarylsulfinyl, heteroarylalkylsulfinyl, and heterocycloalkylsulfinyl, any of which may be optionally substituted; or the $R_6$ and $R_7$ moieties may be combined together with the atoms to which they are attached and joined to firm an optionally substituted 5- to 7-membered ring that incorporates a sultinyl (—S[O]—) moiety.

10. The compound according to claim 9, wherein $R_2$ to $R_5$ are independently selected from the group consisting of hydrogen, D, F, Cl, Br, CN, $(C_1-C_6)$-alkyl, $(C_3-C_6)$cycloalkyl, $(C_1-C_6)$-alkoxy, $(C_1-C_3)$-haloalkyl, $(C_7-C_4)$-perhaloalkyl, $(C_1-C_4)$-perhaloalkoxy, and $(C_1-C_6)$-alkylthio, any of which may be optionally substituted.

11. The compound according to claim 10, wherein $R_1$ is selected from the group consisting of hydrogen, and Q is selected from hydrogen, methyl, ethyl, n-propyl, isopropyl, n-butyl, 2-methyl-1-propyl, sec-butyl, tert-butyl, 2,3-dimethylbutan-2-yl, cyclohexyl, 2,6-dimethylcyclohexyl, 1-methylcyclohexyl, phenyl, 4-pyridyl, benzyl, 4-pyridylmethyl, phenylethyl, (S)-1-hydroxy-(phenylethyl), 2-pyrazinyl, phenylethenyl, (E)-2-(4-pyridazinyl)-1-ethenyl, (E)-4-(2-)-1 H imidazolyl-1-ethenyl, 3-acetoxyl-1-propyl, ethoxycarbonylethyl, methoxylcarbonylpropyl, N-methylaminocarbonylethyl, N-ethylaminocarbonylpropyl, 3-(N-ethylaminocarbonyl)-2,2-dimethyl-1-propyl, N-(morpholinoethyl)aminocarbonylethyl, 3-pyridylmethylaminocarbonylethyl, 4-pyridylmethylaminocarbonylethyl, 4-pyridylmethylarninocarbonylpropyl, carboxyethyl, carboxypropyl, 2-piperidinyl, 3-piperidinyl, 4-piperidinyl, 2-piperazinyl, (S)-1-aminoethyl, (R)-1-aminoethyl, (S)-1-aminoisobutyl, 1-aminocyclopropyl, methoxy, ethoxy, isopropoxy, isobutoxy, neopentyloxy, cyclohexyloxy, 4-piperidinyloxy, 3-acetoxy-2-methyl-1-propoxy, tert-pentyloxy, 4-acetoxybenzyloxy, 3-(4-acetoxyphenyl)-2-propenyloxy, (E)-2-methyl-4-(2-oxo-2,3-dihydrobenzofuran-5-yl)but-3-en-2-yloxy, pivaloyloxymethoxy, pivaloyloxy-1-ethoxy, isopropoxycarbonyloxymethoxy, isopropoxycarbonyloxy-1-ethoxy, amino, N-methylamino, N-ethylamino, N,N-dimethylamino, N-propylamino, N-isopropylamino, N-butylamino, N-piperidinyl, N-piperazinyl, N-4-methylpiperazinyl, N-cyclohexylamino, N-benzylamino, N-(2,4-dimethoxy)benzylamino, 2-(N-methylcarboxamido)phenylamino, N-methyl-2-hydroxyethylamino, $N^1,N^2$-dimethyl-1,2-ethanediamin-1-yl, $N^1,N^2$diethyl-1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl.

12. The compound according to claim 11, wherein $R_2$ to $R_5$ are independently selected from the group consisting of hydrogen, D, F, Cl, CN, methyl, ethyl, n-propyl, isopropyl, n-hexyl, cyclopropyl, merhoxy, ethoxy, isopropoxy, trifluoromethyl, tetrafluoroethoxy, methylthio, and t-butylthio, any of which may be optionally substituted; and wherein $R_7$ is selected from the group consisting of methylsulfinyl, ethylsulfinyl, isopropylsulfinyl, methylsulfinylmethyl, 2-(ethylsulfinyl)ethyl, t-butylsulfinylmethyl, cyclopropylsulfinyl, cyclopentylsulfinyl, phenylsulfinyl, benzylsulfinyl, phenethylsulfinyl, 2-pyridylsulfinyl, 2-pyrazinylsulfinyl, 4-thiazolylsulfinyl, 4-pyridylmethylsulfinyl, 3-thienylmethylsulfinyl, 4-piperidinylsulfinyl, and tetrahydro-2H-pyranylsulfinyl, any of which may be optionally substituted.

13. The compound according claim 12, wherein $R_1$ is selected from the group consisting of hydrogen and $R_8$ and $R_9$ in Q-C(=O)— is selected from the group consisting of methyl, ethyl, ethoxy, isopropoxy, isobutoxy, phenyl, phenylethenyl, 4-piperidinyl, N-piperazinyl, N-(2,4-dimethoxy)benzylamino, 2-(N-methylcarboxamido)-phenylamino, $N^1,N^2$-dimethyl-1,2-ethanediamin-1-yl, $N^1,N^2$-diethyl-,1,2-ethanediamin-1-yl, $N^1,N^2$-dimethyl-1,3-propanediamin-1-yl, and $N^1$-methyl-$N^2$-(2-morpholinoethyl)-1,2-ethanediamin-1-yl;

wherein $R_2$ to $R_5$ are independently selected from the group consisting of hydrogen, F, Cl, methyl, ethyl, cyclopropyl, methoxy, ethoxy, trifluoromethyl and methylthio, any of which may be optionally substituted; and wherein $R_7$ is selected from the group consisting of methylsulfinyl, ethylsulfinyl, isopropylsulfinyl, methylsulfinylmethyl, t-butylsulfinylmethyl, cyclopropylsulfinyl, and benzylsulfinyl.

14. The compound according to claim 13, wherein $R_1$ is selected from the group consisting of hydrogen and Q-C(=O)—, where $R_8$ is methyl;

wherein $R_2$ through $R_5$ are hydrogen; and wherein $R_7$ is methylsulfinyl.

15. A compound selected from the group consisting of:

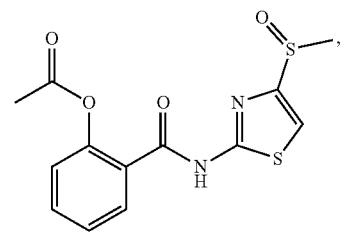

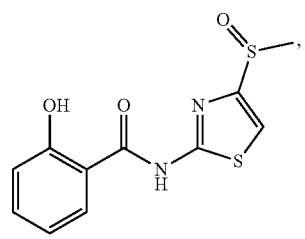

-continued
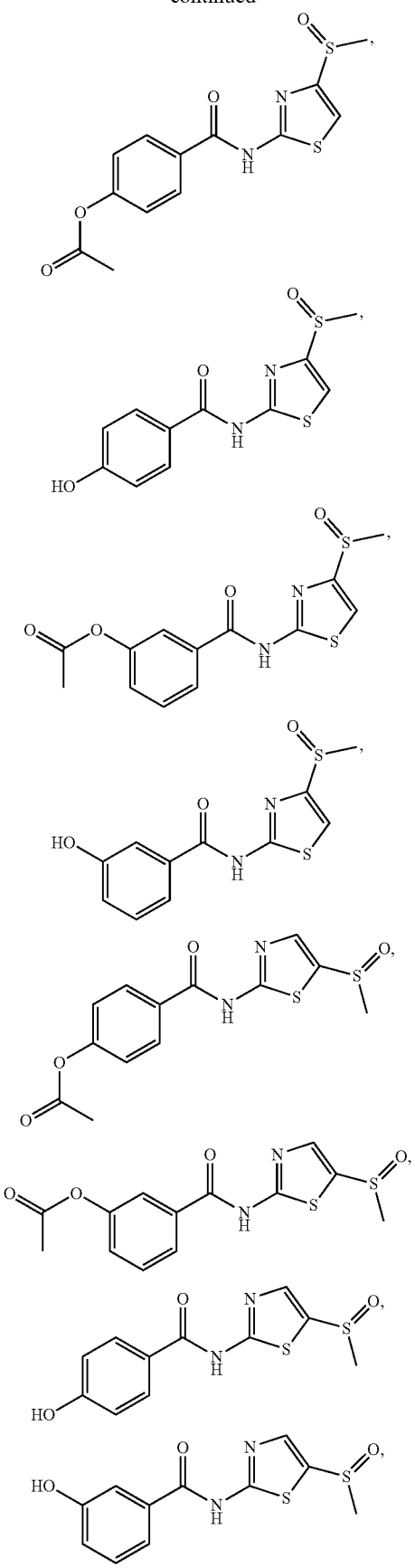
-continued
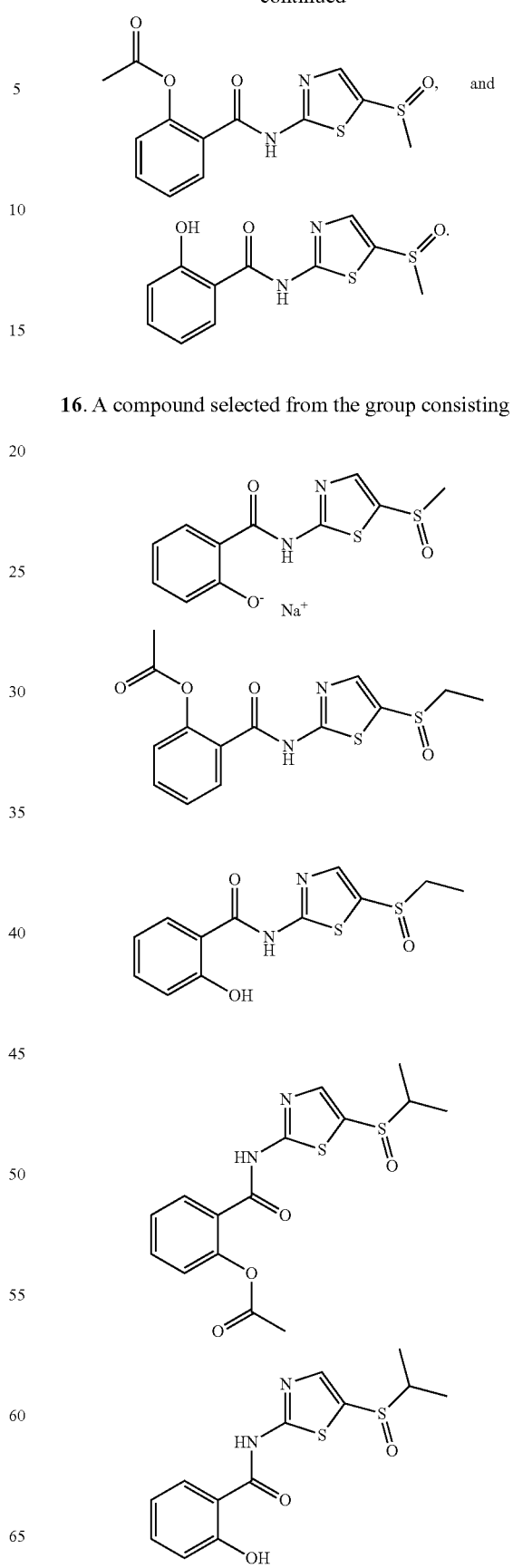
16. A compound selected from the group consisting of:

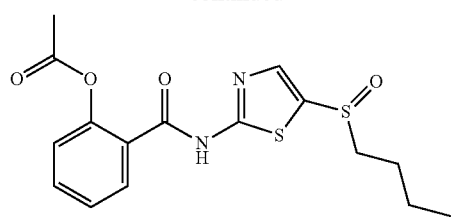
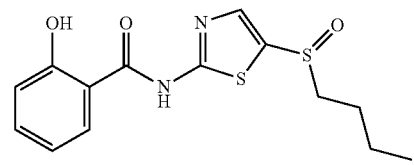
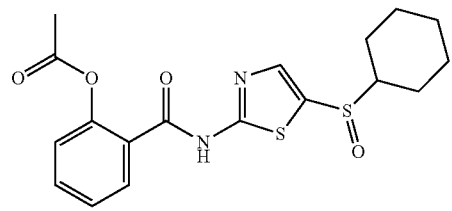
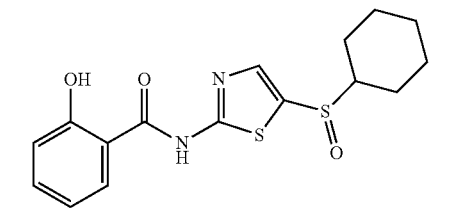
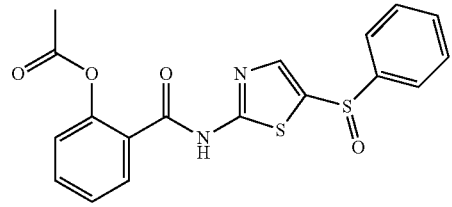
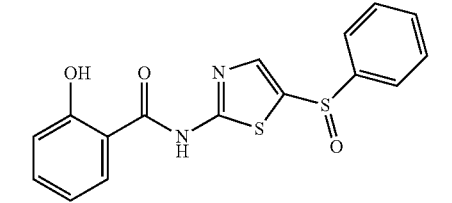
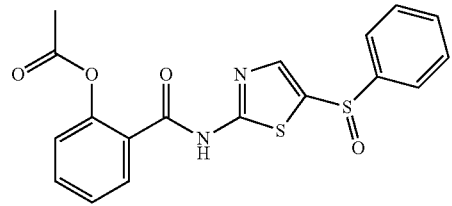
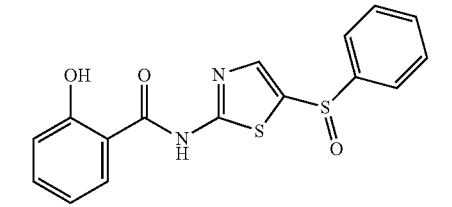
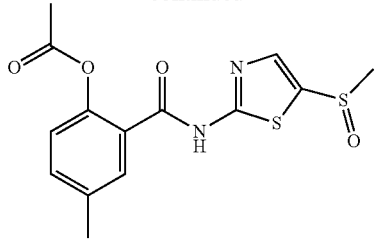
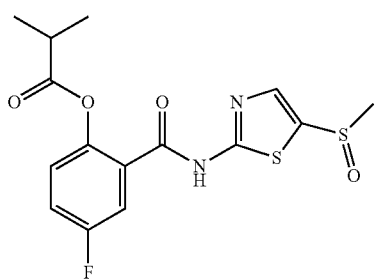
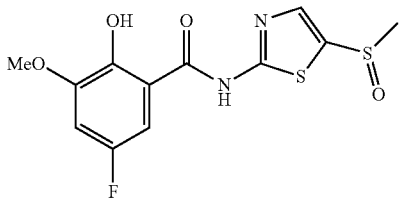
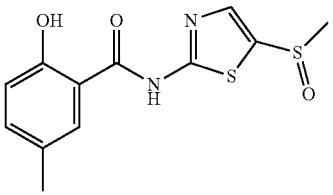
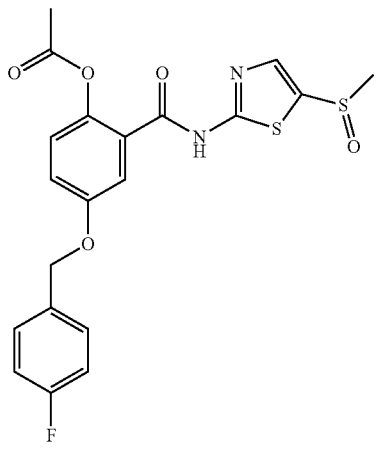

73
-continued
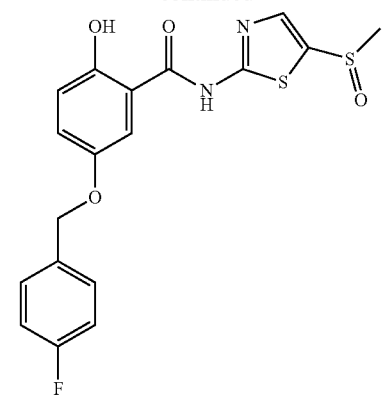
74
-continued
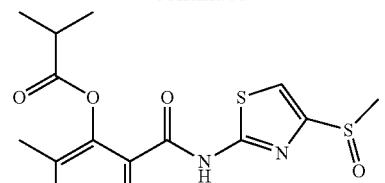
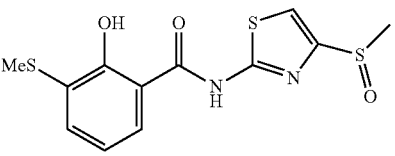
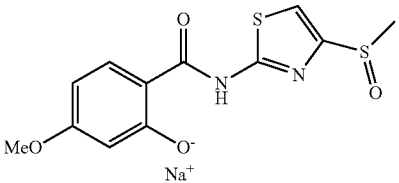
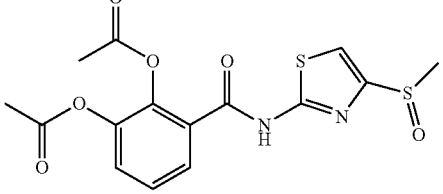
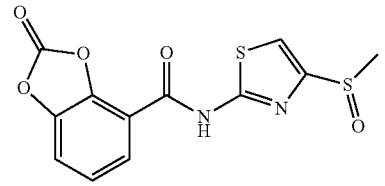
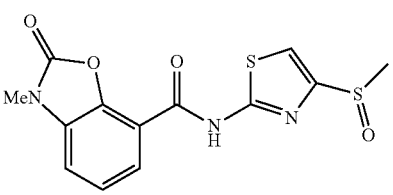
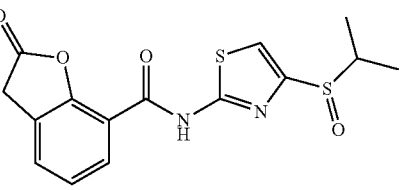
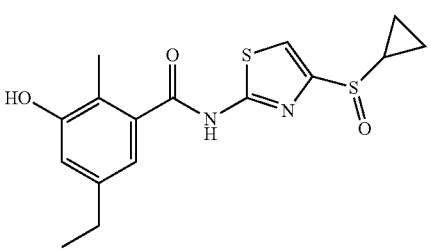

75
-continued
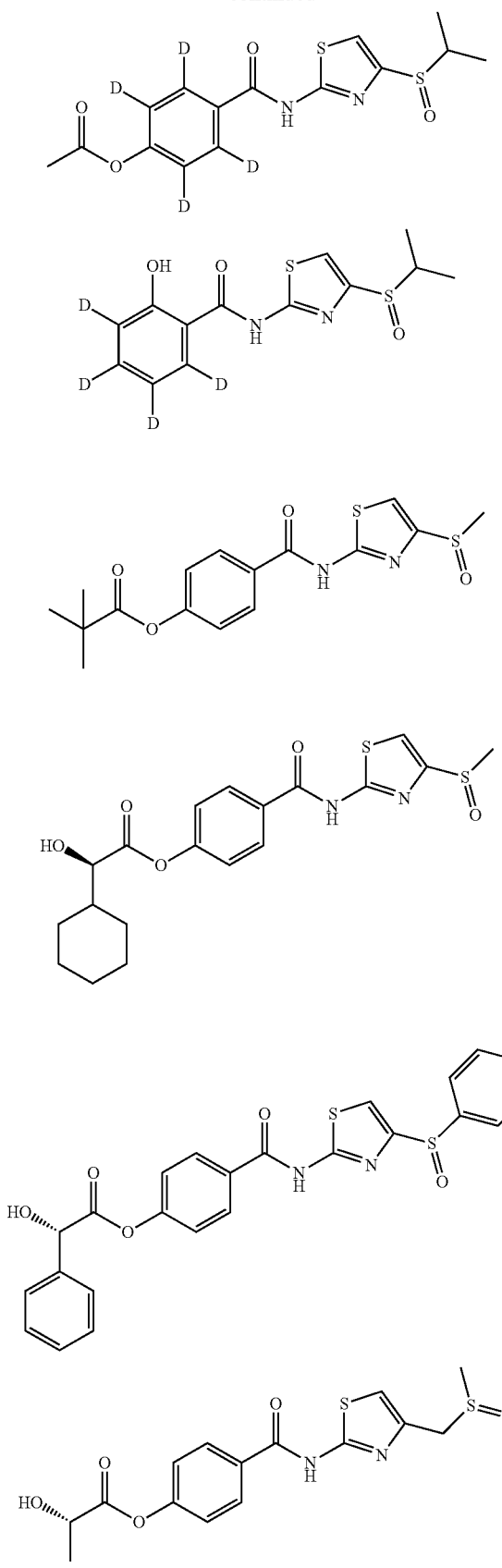
76
-continued
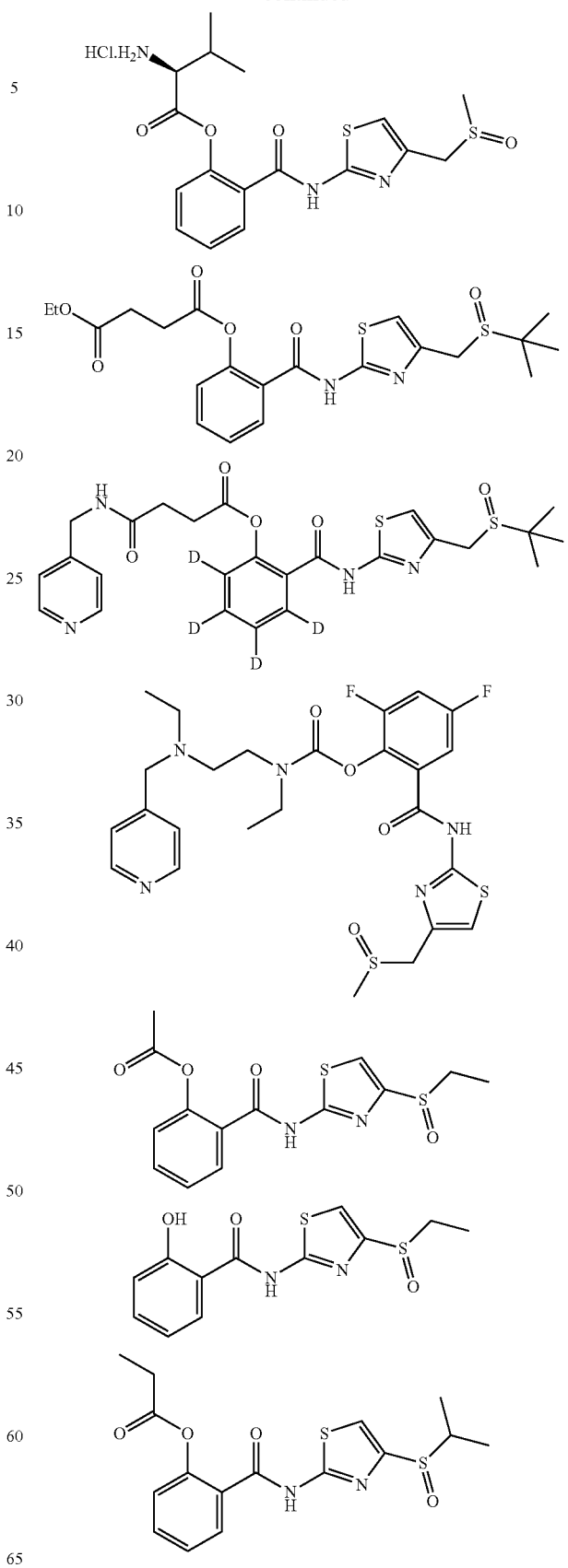

-continued
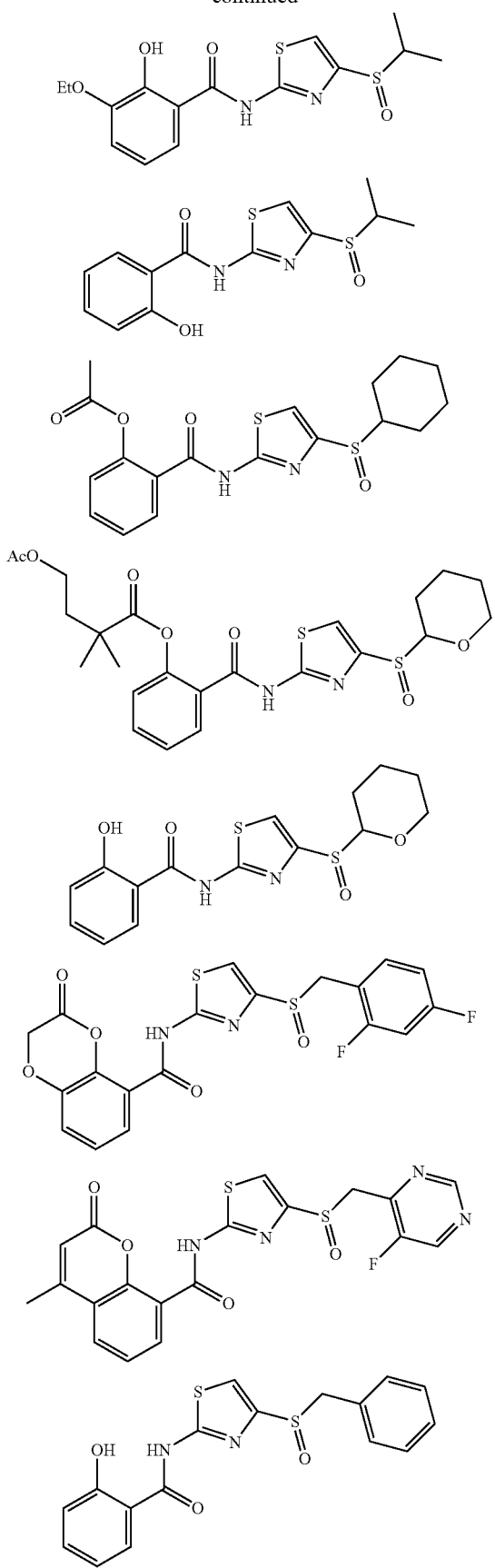
-continued
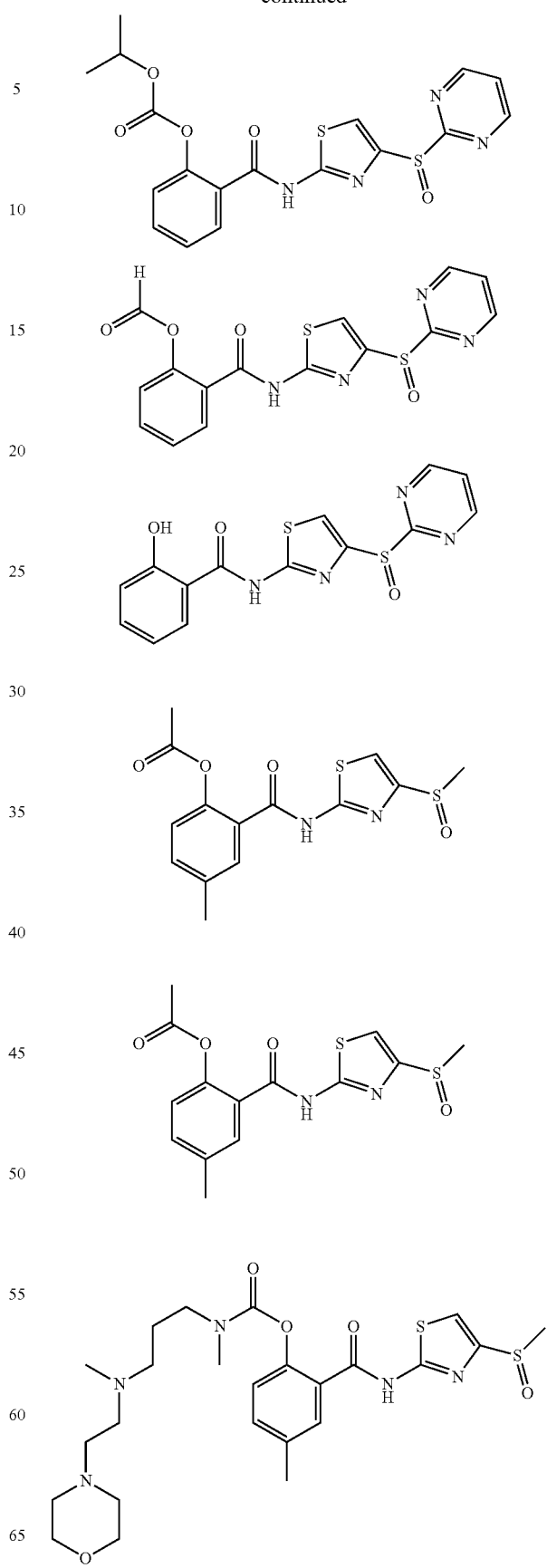

79
-continued
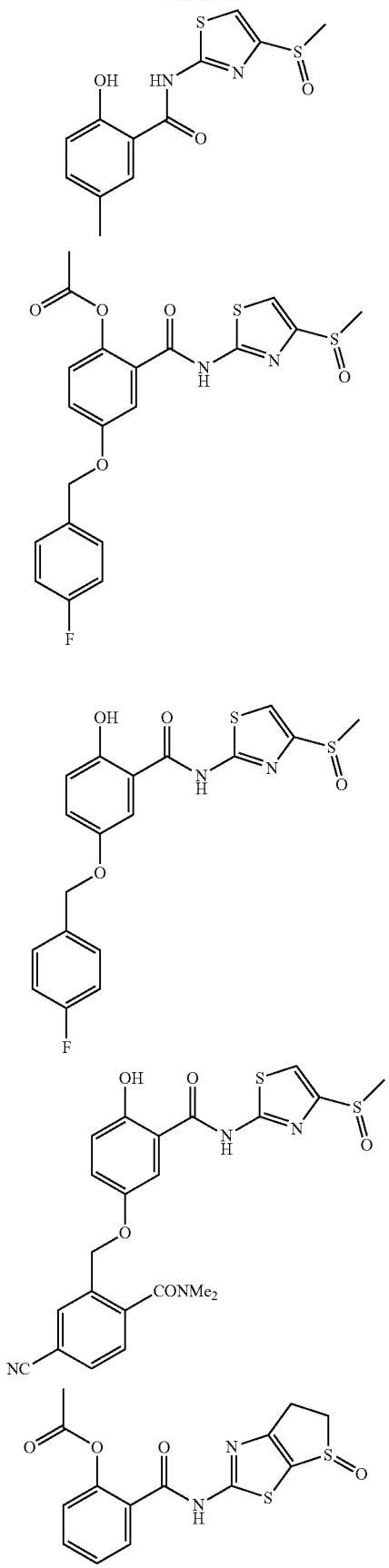
80
-continued
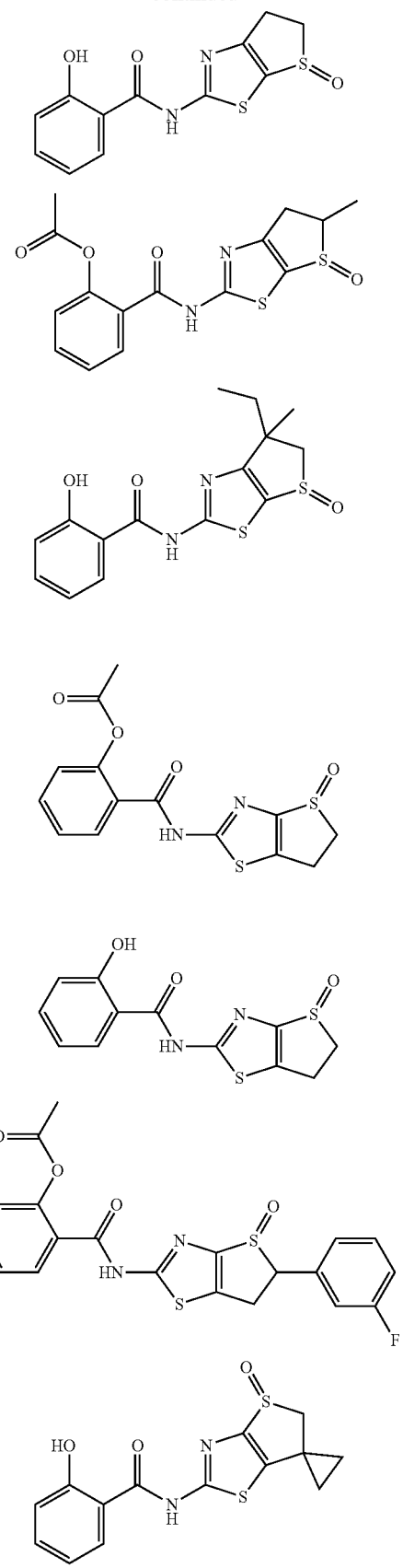

-continued

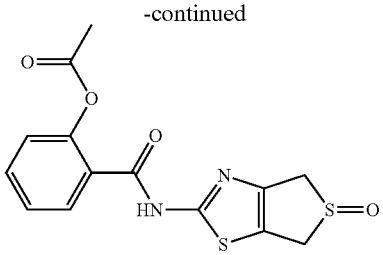
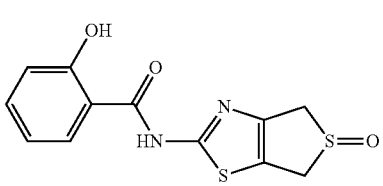
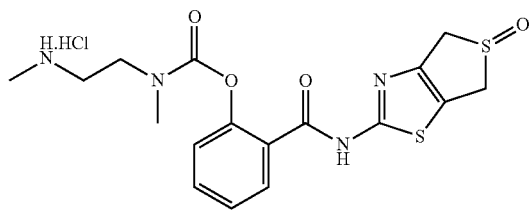
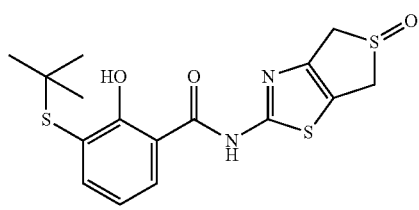

-continued

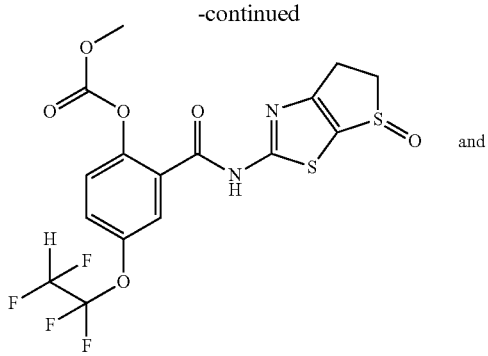
and
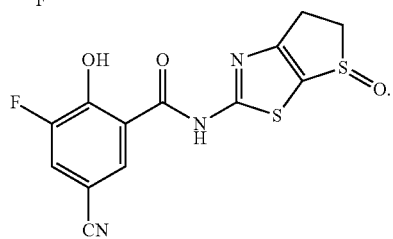

17. The compound according to claim 1, wherein the salt is selected from the group consisting of acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethane-sulfonate, lactate, malate, maleate, methanesulfonate, 2-naphthalenesulfonate, nicotinate, oxalate, thiocyanate, tosylate, undecanoate, lithium, sodium, calcium, potassium, aluminum, ammonium, tetraethylammonium, methylammonium, dimethylammonium, N-methylmorpholinium and ethanolammonium.

\* \* \* \* \*